(12) United States Patent
Ofran et al.

(10) Patent No.: US 11,468,969 B2
(45) Date of Patent: Oct. 11, 2022

(54) COMPUTER ASSISTED ANTIBODY RE-EPITOPING

(71) Applicant: Biolojic Design Ltd., Rehovot (IL)

(72) Inventors: Yanay Ofran, Tel Aviv (IL); Guy Nimrod, Tel Aviv (IL); Sharon Fischman, Modiein (IL); Asael Her residue position selected in b; such that a library containing a plurality of variants of said template is generated.

6 Claims, 24 Drawing Sheets

(51) Int. Cl.
| | |
|---|---|
| G16B 15/00 | (2019.01) |
| G16B 35/00 | (2019.01) |
| G16C 20/60 | (2019.01) |
| C40B 10/00 | (2006.01) |
| G01N 33/68 | (2006.01) |
| G16B 15/30 | (2019.01) |
| G16B 35/20 | (2019.01) |
| G16B 20/50 | (2019.01) |

(52) U.S. Cl.
CPC ............. *G16B 15/00* (2019.02); *G16B 15/30* (2019.02); *G16B 20/00* (2019.02); *G16B 35/00* (2019.02); *G16B 35/20* (2019.02); *G16C 20/60* (2019.02); *C07K 2317/565* (2013.01); *G16B 20/50* (2019.02)

(58) Field of Classification Search
CPC ............ C07K 2317/70; C07K 2299/00; C07K 2317/20; C07K 2318/20; C07K 16/005; C07K 2317/30; C07K 2317/50; C07K 2317/567; C07K 2317/569; C07K 2317/66; C07K 2317/64; C07K 2317/94; C07K 2318/10; C07K 2317/00; C12Q 2600/136; C12Q 2600/156; G01N 33/68; G01N 33/6854; G01N 2333/47; G01N 2500/00; G01N 2500/04; G01N 2570/00; G01N 2333/70596; G01N 33/6857; C40B 40/10; C40B 40/08; C40B 30/04; C40B 50/18; C40B 40/06; C40B 30/00; G16B 20/20; G16B 30/10; G16B 40/20; G16B 35/00; G16B 15/00; G16B 20/00; G16B 30/00; G16B 30/20; G16B 50/30; G16B 5/00; G16B 15/30; G16B 40/00; G16B 20/30; G16B 20/50; G16B 35/20; G16B 15/20; G16B 45/00; G16B 50/00; G16B 40/30; G16B 35/10; G16B 40/10; B01D 15/3809; G06T 19/00; A61K 38/1774; A61K 2039/505; A61K 39/395; G16C 10/00; G16C 20/60; G16C 20/30; G16C 20/64; G16C 20/70; G16C 20/90; G16C 20/20; G16C 20/62; G16H 50/70; G06K 9/00201; C12P 21/00; C12P 21/02

See application file for complete search history.

(56) References Cited

U.S. PATENT DOCUMENTS

| | | | |
|---|---|---|---|
| 2013/0079243 A1* | 3/2013 | Diem | ............... C40B 40/08 506/9 |
| 2020/0124615 A1* | 4/2020 | Ofran | ............... C12N 15/1058 |

FOREIGN PATENT DOCUMENTS

| | | | | |
|---|---|---|---|---|
| WO | WO2013177214 | | 11/2013 | |
| WO | WO-2020008412 A1 * | 1/2020 | ........... | A23L 33/125 |

OTHER PUBLICATIONS

Tinberg, C. et al. Computational design of ligand-binding proteins with high affinity and selectivity. Nature (2013) vol. 501 pp. 212-218.*

Tinberg et al. Nature 2013 Supplemental Material.*
Kuroda et al. Computer-aided antibody design. Protein Engineering Design and Selection (2012) vol. 25 No. 10 pp. 507-521.*
Abhinandan et al. "Analysis and improvements to Kabat and structurally correct numbering of antibody variable domains" Molecular immunology. Aug. 1, 2008;45(14):3832-9.
Almagro JC. "Identification of differences in the specificity-determining residues of antibodies that recognize antigens of different size: implications for the rational design of antibody repertoires" Journal of Molecular Recognition. Mar. 2004;17(2):132-43.
Birtalan et al. "The functional capacity of the natural amino acids for molecular recognition" Molecular bioSystems. 2010;6(7):1186-94.
Breiman L. "Random forests. Machine learning" Oct. 1, 2001;45(1):5-32.
Brooks et al. "CHARMM: the biomolecuiar simulation program" Journal of computational chemistry. Jul. 30, 2009;30(10):1545-614.
Chothia C. "The nature of the accessible and buried surfaces in proteins" Journal of molecular biology. Jul. 25, 1976;105(1):1-2.
Co et al. "Humanized antibodies for therapy" Nature. Jun. 1991;351(6326):501-2.
Collis et al. "Analysis of the antigen combining site: correlations between length and sequence composition of the hypervariable loops and the nature of the antigen" Journal of molecular biology. Jan. 10, 2003;325(2):337-54.
Crameri et al. "Construction and evolution of antibody-phage libraries by DMA shuffling" Nature medicine. Jan. 1, 1996;2(1):100-2.
Dörner et al. "Analysis of the frequency and pattern of somatic mutations within nonproductively rearranged human variable heavy chain genes" The Journal of Immunology. Mar. 15, 1997;158(6):2779-89.
Feig et al. "Performance comparison of generalized born and Poisson methods in the calculation of electrostatic solvation energies for protein structures" Journal of computational chemistry. Jan. 30, 2004;25(2):265-84.
Fellouse et al. "High-throughput generation of synthetic antibodies from highly functional minimalist phage-displayed libraries" Journal of molecular biology. Nov. 2, 2007;373(4):924-40.
Figini et al. "In vitro assembly of repertoires of antibody chains on the surface of phage by renaturation" Journal of molecular biology. May 26, 1994;239(1):68-78.
Goldsmith-Fischman et al. "The SufE sulfur-acceptor protein contains a conserved core structure that mediates interdomain interactions in a variety of redox protein complexes" Journal of molecular biology. Nov. 19, 2004;344(2):549-65.
Guerois et al. "Predicting changes in the stability of proteins and protein complexes: a study of more than 1000 mutations" Journal of molecular biology. Jul. 5, 2002;320(2):369-87.
Haidar et al. "A universal combinatorial design of antibody framework to graft distinct CDR sequences: A bioinformatics approach" Proteins: Structure, Function, and Bioinformatics. Mar. 2012;80(3):896-912.
Hanf et al. "Antibody humanization by redesign of complementarity-determining region residues proximate to the acceptor framework" Methods. Jan. 1, 2014;65(1):68-76.
Hawkins et al. "Selection of phage antibodies by binding affinity: mimicking affinity maturation" Journal of molecular biology. Aug. 5, 1992;226(3):889-96.
Hemminki et al. "Fine tuning of an anti-testosterone antibody binding site by stepwise optimisation of the CDRs" Immunotechnology. Jun. 1, 1998;4(1):59-69.
Hess et al. "GROMACS 4: algorithms for highly efficient, load-balanced, and scalable molecular simulation" Journal of chemical theory and computation. Mar. 11, 2008;4(3):435-47.
Huang SY. "Search strategies and evaluation in protein-protein docking: principles, advances and challenges" Drug discovery today. Aug. 1, 2014;19(8):1081-96.
Janin J. "Protein-protein docking tested in blind predictions: the CAPRI experiment" Molecular BioSystems. 2010;6(12):2351-62.
Karplus et al. "Molecular dynamics simulations of biomolecules" Nature structural biology. Sep. 2002;9(9):646-52.

(56) References Cited

OTHER PUBLICATIONS

Kinoshita et al. "Linking class-switch recombination with somatic hypermutation" Nature reviews Molecular cell biology. Jul. 2001;2(7):493-503.
Kulkarni-Kale et al. "Antigen-antibody interaction database (AgAbDb): a compendium of antigen-antibody Interactions" In Immunoinformatics 2014 (pp. 149-164). Humana Press, New York, NY.
Kunik et al. "Structural consensus among antibodies defines the antigen binding site" PLoS Comput Biol. Feb. 23, 2012;8(2):e1002388.
Kuroda et al. "Structural classification of CDR-H3 revisited: a lesson in antibody modeling" Proteins: Structure, Function, and Bioinformatics. Nov. 15, 2008;73(3):608-20.
Laskowski et al. "PDBsum: a Web-based database of summaries and analyses of all PDB structures" Trends in biochemical sciences. Dec. 1, 1997;22(12):488-90.
Liang et al. "Function blocking antibodies to neuropilin-1 generated from a designed human synthetic antibody phage library" Journal of molecular biology. Feb. 23, 2007;366(3):815-29.
Lin J. "Divergence measures based on the Shannon entropy" IEEE Transactions on Information theory. Jan. 1991;37(1):145-51.
Lou et al. "Affinity maturation by chain shuffling and site directed mutagenesis" In Antibody Engineering 2010 (pp. 377-396). Springer, Berlin, Heidelberg.
MacCallum et al. "Antibody-antigen interactions: contact analysis and binding site topography" Journal of molecular biology. Oct. 11, 1996;262(5):732-45.
Mahon et al. "Comprehensive interrogation of a minimalist synthetic CDR-H3 library and its ability to generate antibodies with therapeutic potential" Journal of molecular biology. May 27, 2013;425(10):1712-30.
Marks et al. "By-Passing Immunization: Building High Affinity Human Antibodies by Chain Shuffling" Bio/technology. Jul. 1992;10(7):779-83.
McDonald et al. "Satisfying hydrogen bonding potential in proteins" Journal of molecular biology. May 19, 1994;238(5):777-93.
Mirick et al. "A review of human anti-globulin antibody (HAGA, HAMA, HACA, HAHA) responses to monoclonal antibodies. Not four letter words" The quarterly journal of nuclear medicine and molecular imaging. Dec. 1, 2004;48(4):251.
Moal et al. "Scoring functions for protein-protein interactions" Current opinion in structural biology. Dec. 1, 2013;23(6):862-7.
Morea et al. "Antibody modeling: implications for engineering and design" Methods. Mar. 1, 2000;20(3):267-79.
North et al. "A new clustering of antibody CDR loop conformations" Journal of molecular biology. Feb. 18, 2011;406(2):228-56.
Ohlin et al. "Light chain shuffling of a high affinity antibody results in a drift in epitope recognition" Molecular immunology. Jan. 1, 1996;33(1):47-56.
Persson et al. "Molecular evolution of specific human antibody against MUC1 mucin results in improved recognition of the antigen on tumor cells" Tumor Biology. 2009;30(4):221-31.
Pham et al. "Processive AID-catalysed cytosine deamination on single-stranded DNA simulates somatic hypermutation" Nature. Jul. 2003;424(6944):103-7.
Raghunathan et al. "Antigen-binding site anatomy and somatic mutations in antibodies that recognize different types of antigens" Journal of Molecular Recognition. Mar. 2012;25(3):103-13.
Rajewsky K. "Clonal selection and learning in the antibody system" Nature. Jun. 1996;381(6585):751-8.
Ramirez-Benitez et al. "Analysis of antibodies of known structure suggests a lack of correspondence between the residues in contact with the antigen and those modified by somatic hypermutation" Proteins: Structure, Function, and Bioinformatics. Nov. 15, 2001;45(3):199-206.
Rothe et al. "The human combinatorial antibody library HuCAL GOLD combines diversification of all six CDRs according to the natural immune system with a novel display method for efficient selection of high-affinity antibodies" Journal of molecular biology. Feb. 29, 2008;376(4):1182-200.
Šali et al. "Comparative protein modelling by satisfaction of spatial restraints" Journal of molecular biology. Dec. 5, 1993;234(3):779-815.
Scheid et al. "Broad diversity of neutralizing antibodies isolated from memory B cells in HIV-infected individuals" Nature. Apr. 2009;458(7238):636-40.
Schmidt et al. "Preconfiguration of the antigen-binding site during affinity maturation of a broadly neutralizing influenza virus antibody" Proceedings of the National Academy of Sciences. Jan. 2, 2013;110(1):264-9.
Sela-Culang et al. "Antibody specific epitope prediction—emergence of a new paradigm" Current opinion in virology. Apr. 1, 2015;11:98-102.
Söderlind et al. "Complementarity-determining region (CDR) implantation: a theme of recombination" Immunotechnology: an international journal of immunological engineering. Mar. 1999;4(3-4):279.
Tramontano et al. "Framework residue 71 is a major determinant of the position and conformation of the second hypervariable region in the VH domains of immunoglobulins" Journal of molecular biology. Sep. 5, 1990;215(1):175-82.
Wong et al. "Effects of somatic mutations on CDR loop flexibility during affinity maturation" Proteins: Structure, Function, and Bioinformatics. Mar. 2011;79(3):821-9.
Wu et al. "Rational design of envelope identifies broadly neutralizing human monoclonal antibodies to HIV-1" Science. Aug. 13, 2010;329(5993):856-61.
Xu et al. "Structural basis of preexisting immunity to the 2009 H1N1 pandemic influenza virus" Science. Apr. 16, 2010;328(5976):357-60.
Ye et al. "IgBLAST: an immunoglobulin variable domain sequence analysis tool" Nucleic acids research. Jul. 1, 2013;41(W1):W34-40.
Zacharias M. "Accounting for conformational changes during protein-protein docking" Current opinion in structural biology. Apr. 1, 2010;20(2):180-6.
Zhai et al. "Synthetic antibodies designed on natural sequence landscapes" Journal of molecular biology. Sep. 9, 2011;412(1):55-71.
Zhang et al. "Structure-based prediction of protein-protein interactions on a genome-wide scale" Nature. Oct. 2012;490(7421):556-60.
Zhao et al. "A germline knowledge based computational approach for determining antibody complementarity determining regions" Molecular immunology. Jan. 1, 2010;47(4):694-700.
Abhinandan, K. R., & Martin, A. C. (2007). Analyzing the "degree of humanness" of antibody sequences. Journal of molecular biology, 369(3), 852-862.
Acierno, J. P., Braden, B. C., Klinke, S., Goldbaum, F. A., & Cauerhff, A. (2007). Affinity maturation increases the stability and plasticity of the Fv domain of anti-protein antibodies. Journal of molecular biology, 374(1), 130-146.
Beck, A., Wurch, T., Bailly, C., & Corvaia, N. (2010). Strategies and challenges for the next generation of therapeutic antibodies. Nature reviews immunology, 10(5), 345-352.
Berman, H. M., Battistuz, T., Bhat, T. N., Bluhm, W. F., Bourne, P. E., Burkhardt, K., . . . & Fagan, P. (2002). The protein data bank. Acta Crystallographica Section D: Biological Crystallography, 58(6), 899-907.
Berman, H. M., Westbrook, J., Feng, Z., Gilliland, G., Bhat, T. N., Weissig, H., . . . & Bourne, P. E. (2000). The protein data bank. Nucleic acids research, 28(1), 235-242.
Bostrom, J., Yu, S. F., Kan, D., Appleton, B. A., Lee, C. V., Billeci, K., . . . & Fuh, G. (2009). Variants of the antibody herceptin that interact with HER2 and VEGF at the antigen binding site. Science, 323(5921), 1610-1614.
Bowers, P. M., Horlick, R. A., Neben, T. Y., Toobian, R. M., Tomlinson, G. L., Dalton, J. L., . . . & Macomber, J. L. (2011). Coupling mammalian cell surface display with somatic hypermutation for the discovery and maturation of human antibodies. Proceedings of the National Academy of Sciences, 108(51), 20455-20460.
Braunagel, M., & Little, M. (1997). Construction of a semisynthetic antibody library using trinucleotide oligos. Nucleic acids research, 25(22), 4690-4691.

(56) References Cited

OTHER PUBLICATIONS

Burkovitz, A., & Ofran, Y. (Feb. 2016). Understanding differences between synthetic and natural antibodies can help improve antibody engineering. MAbs (vol. 8, No. 2, pp. 278-287).

Burkovitz, A., Leiderman, O., Sela-Culang, I., Byk, G., & Ofran, Y. (2013). Computational identification of antigen-binding antibody fragments. The Journal of Immunology, 190(5), 2327-2334.

Burkovitz, A., Sela-Culang, I., & Ofran, Y. (2014). Large-scale analysis of somatic hypermutations in antibodies reveals which structural regions, positions and amino acids are modified to improve affinity. The FEBS journal, 281(1), 306-319.

Capra, J. D., & Kehoe, J. M. (1974). Variable region sequences of five human immunoglobulin heavy chains of the VHIII subgroup: definitive identification of four heavy chain hypervariable regions. Proceedings of the National Academy of Sciences, 71(3), 845-848.

Chailyan, A., Marcatili, P., & Tramontano, A. (2011). The association of heavy and light chain variable domains in antibodies: implications for antigen specificity. The FEBS journal, 278(16), 2858-2866.

Chen, R., Li, L., & Weng, Z. (2003). ZDOCK: an initial-stage protein-docking algorithm. Proteins: Structure, Function, and Bioinformatics, 52(1), 80-87.

Chong, L. T., Duan, Y., Wang, L., Massova, I., & Kollman, P. A. (1999). Molecular dynamics and free-energy calculations applied to affinity maturation in antibody 48G7. Proceedings of the National Academy of Sciences, 96(25), 14330-14335.

Chothia, C., & Lesk, A. M. (1987). Canonical structures for the hypervariable regions of immunoglobulins. Journal of molecular biology, 196(4), 901-917.

Chothia, C., Lesk, A. M., Tramontano, A., Levitt, M., Smith-Gill, S. J., Air, G., . . . & Colman, P. M. (1989). Conformations of immunoglobulin hypervariable regions. Nature, 342(6252), 877-883.

Chowdhury, P. S., & Pastan, I. (1999). Improving antibody affinity by mimicking somatic hypermutation in vitro. Nature biotechnology, 17(6), 568-572.

Clark, L. A., Ganesan, S., Papp, S., & van Vlijmen, H. W. (2006). Trends in antibody sequence changes during the somatic hypermutation process. The Journal of Immunology, 177(1), 333-340.

Comeau, S. R., Gatchell, D. W., Vajda, S., & Camacho, C. J. (2004). ClusPro: a fully automated algorithm for protein-protein docking. Nucleic acids research, 32(suppl_2), W96-W99.

Cortes, C., & Vapnik, V. (1995). Support-vector networks. Machine learning, 20(3), 273-297.

Dayhoff, M., Schwartz, R., & Orcutt, B. (1978). 22 a model of evolutionary change in proteins. In Atlas of protein sequence and structure (vol. 5, pp. 345-352). MD: National Biomedical Research Foundation Silver Spring.

Der Maur, A. A., Zahnd, C., Fischer, F., Spinelli, S., Honegger, A., Cambillau, C., . . . & Barberis, A. (2002). Direct in vivo screening of intrabody libraries constructed on a highly stable single-chain framework. Journal of Biological Chemistry, 277(47), 45075-45085.

Dey, F., Cliff Zhang, Q., Petrey, D., & Honig, B. (2013). Toward a "structural BLAST": Using structural relationships to infer function. Protein Science, 22(4), 359-366.

Di Noia, J. M., & Neuberger, M. S. (2007). Molecular mechanisms of antibody somatic hypermutation. Annu. Rev. Biochem., 76, 1-22.

Dominguez, C., Boelens, R., & Bonvin, A. M. (2003). HADDOCK: a protein- protein docking approach based on biochemical or biophysical information. Journal of the American Chemical Society, 125(7), 1731-1737.

Dörner, T., Foster, S. J., Farner, N. L., & Lipsky, P. E. (1998). Somatic hypermutation of human immunoglobulin heavy chain genes: targeting of RGYW motifs on both DNA strands. European journal of immunology, 28(10), 3384-3396.

Dunbar, J., Fuchs, A., Shi, J., & Deane, C. M. (2013). ABangle: characterising the VH-VL orientation in antibodies. Protein Engineering, Design & Selection, 26(10), 611-620.

Dunbar, J., Krawczyk, K., Leem, J., Baker, T., Fuchs, A., Georges, G., . . . & Deane, C. M. (2014). SAbDab: the structural antibody database. Nucleic acids research, 42(D1), D1140-D1146.

Ehrenmann, F., Kaas, Q., & Lefranc, M. P. (2010). IMGT/3Dstructure-DB and IMGT/DomainGapAlign: a database and a tool for immunoglobulins or antibodies, T cell receptors, MHC, IgSF and MhcSF. Nucleic acids research, 38(suppl_1), D301-D307.

Farady, C. J., Egea, P. F., Schneider, E. L., Darragh, M. R., & Craik, C. S. (2008), Structure of an Fab-protease complex reveals a highly specific non-canonical mechanism of inhibition. Journal of molecular biology, 380(2), 351-360.

Fellouse, F. A., Li, B., Compaan, D. M., Peden, A. A., Hymowitz, S. G., & Sidhu, S. S. (2005). Molecular recognition by a binary code. Journal of molecular biology, 348(5), 1153-1162.

Fiser, A., & Do, R. K. G. (2000). Modeling of loops in protein structures. Protein science, 9(9), 1753-1773.

Fleishman, S. J., Whitehead, T. A., Ekiert, D. C., Dreyfus, C., Corn, J. E., Strauch, E. M., . . . & Baker, D. (2011). Computational design of proteins targeting the conserved stem region of influenza hemagglutinin. Science, 332(6031), 816-821.

Gao, M., & Skolnick, J. (2010). iAlign: a method for the structural comparison of protein-protein interfaces. Bioinformatics, 26(18), 2259-2265.

Giudicelli, V., Chaume, D., & Lefranc, M. P. (2005). IMGT/GENE-DB: a comprehensive database for human and mouse immunoglobulin and T cell receptor genes. Nucleic acids research, 33(suppl_1), D256-D261.

Glanville, J., Zhai, W., Berka, J., Telman, D., Huerta, G., Mehta, G. R., . . . & Cox, D. (2009). Precise determination of the diversity of a combinatorial antibody library gives insight into the human immunoglobulin repertoire. Proceedings of the National Academy of Sciences, 106(48), 20216-20221.

Goldsmith-Fischman, S., & Honig, B. (2003). Structural genomics: computational methods for structure analysis. Protein Science, 12(9), 1813-1821.

Gonzales, N. R., Padlan, E. A., De Pascalis, R., Schuck, P., Schlom, J., & Kashmiri, S. V. (2004). SDR grafting of a murine antibody using multiple human germline templates to minimize its immunogenicity. Molecular immunology, 41(9), 863-872.

Gray, J. J., Moughon, S., Wang, C., Schueler-Furman, O., Kuhlman, B., Rohl, C. A., & Baker, D. (2003). Protein-protein docking with simultaneous optimization of rigid-body displacement and side-chain conformations. Journal of molecular biology, 331(1), 281-299.

Hess, B., Kutzner, C., Van Der Spoel, D., & Lindahl, E. (2008). GROMACS 4: algorithms for highly efficient, load-balanced, and scalable molecular simulation. Journal of chemical theory and computation, 4(3), 435-447.

Hoet, R. M., Cohen, E. H., Kent, R. B., Rookey, K., Schoonbroodt, S., Hogan, S., . . . & van Hegelsom, R. (2005). Generation of high-affinity human antibodies by combining donor-derived and synthetic complementarity-determining-region diversity. Nature biotechnology, 23(3), 344-348.

Honegger, A., & PluÈckthun, A. (2001). Yet another numbering scheme for immunoglobulin variable domains: an automatic modeling and analysis tool. Journal of molecular biology, 309(3), 657-670.

Hu, D., Hu, S., Wan, W., Xu, M., Du, R., Zhao, W., . . . & Hong, J. (2015). Effective optimization of antibody affinity by phage display integrated with high-throughput DNA synthesis and sequencing technologies. PLoS One, 10(6).

Hudson, P. J., & Souriau, C. (2003). Engineered antibodies. Nature medicine, 9(1), 129-134.

Jones, P. T., Dear, P. H., Foote, J., Neuberger, M. S., & Winter, G. (1986). Replacing the complementarity-determining regions in a human antibody with those from a mouse. Nature, 321(6069), 522.

International Search Report From PCT PCT/US2015/062768 dated Feb. 22, 2016.

Kaas, Q., Ruiz, M., & Lefranc, M. P. (2004). IMGT/3Dstructure-DB and IMGT/StructuralQuery, a database and a tool for immunoglobulin, T cell receptor and MHC structural data. Nucleic acids research, 32(suppl_1), D208-D210.

(56) References Cited

OTHER PUBLICATIONS

Kabsch, W., & Sander, C. (1983). Dictionary of protein secondary structure: pattern recognition of hydrogen-bonded and geometrical features. Biopolymers: Original Research on Biomolecules, 22(12), 2577-2637.
Klein, F., Diskin, R., Scheid, J. F., Gaebler, C., Mouquet, H., Georgiev, I. S., . . . & Gnanapragasam, P. N. (2013). Somatic mutations of the immunoglobulin framework are generally required for broad and potent HIV-1 neutralization. Cell, 153(1), 126-138.
Knappik, A., Ge, L., Honegger, A., Pack, P., Fischer, M., Wellnhofer, G., . . . & Virnekäs, B. (2000). Fully synthetic human combinatorial antibody libraries (HuCAL) based on modular consensus frameworks and CDRs randomized with trinucleotides. Journal of molecular biology, 296(1), 57-86.
Krawczyk, K., Baker, T., Shi, J., & Deane, C. M. (2013). Antibody i-Patch prediction of the antibody binding site improves rigid local antibody-antigen docking. Protein Engineering, Design & Selection, 26(10), 621-629.
Krawczyk, K., Liu, X., Baker, T., Shi, J., & Deane, C. M. (2014). Improving B-cell epitope prediction and its application to global antibody-antigen docking. Bioinformatics, 30(16), 2288-2294.
Kuhlman, B., Dantas, G., Ireton, G. C., Varani, G., Stoddard, B. L., & Baker, D. (2003). Design of a novel globular protein fold with atomic-level accuracy. science, 302(5649), 1364-1368.
Kunik, V., & Ofran, Y. (2013). The indistinguishability of epitopes from protein surface is explained by the distinct binding preferences of each of the six antigen-binding loops. Protein Engineering, Design & Selection, 26(10), 599-609.
Kunik, V., Ashkenazi, S., & Ofran, Y. (2012). Paratome: an online tool for systematic identification of antigen-binding regions in antibodies based on sequence or structure. Nucleic acids research, 40(W1), W521-W524.
Kunik, V., Peters, B., & Ofran, Y. (2012). Structural consensus among antibodies defines the antigen binding site. PLoS computational biology, 8(2).
Kwong, P. D., & Mascola, J. R. (2012). Human antibodies that neutralize HIV-1: identification, structures, and B cell ontogenies. Immunity, 37(3), 412-425.
Lee, C. V., Liang, W. C., Dennis, M. S., Eigenbrot, C., Sidhu, S. S., & Fuh, G. (2004). High-affinity human antibodies from phage-displayed synthetic Fab libraries with a single framework scaffold. Journal of molecular biology, 340(5), 1073-1093.
Lee, C. V., Sidhu, S. S., & Fuh, G. (2004). Bivalent antibody phage display mimics natural immunoglobulin. Journal of immunological methods, 284(1-2), 119-132.
Lefranc, M. P., Pommié, C., Ruiz, M., Giudicelli, V., Foulquier, E., Truong, L., . . . & Lefranc, G. (2003). IMGT unique numbering for immunoglobulin and T cell receptor variable domains and Ig superfamily V-like domains. Developmental & Comparative Immunology, 27(1), 55-77.
Li, B., Zhao, L., Wang, C., Guo, H., Wu, L., Zhang, X., . . . & Guo, Y. (2010). The protein-protein interface evolution acts in a similar way to antibody affinity maturation. Journal of Biological Chemistry, 285(6), 3865-3871.
Li, Y., Li, H., Yang, F., Smith-Gill, S. J., & Mariuzza, R. A. (2003). X-ray snapshots of the maturation of an antibody response to a protein antigen. Nature Structural & Molecular Biology, 10(6), 482-488.
Li, Z., Woo, C. J., Iglesias-Ussel, M. D., Ronai, D., & Scharff, M. D. (2004). The generation of antibody diversity through somatic hypermutation and class switch recombination. Genes & development, 18(1), 1-11.
Lippow, S. M., Wittrup, K. D., & Tidor, B. (2007). Computational design of antibody-affinity improvement beyond in vivo maturation. Nature biotechnology, 25(10), 1171-1176.
Liu, Y., & Kuhlman, B. (2006). RosettaDesign server for protein design. Nucleic acids research, 34(suppl_2), W235-W238.
MacCarthy, T., Roa, S., Scharff, M. D., & Bergman, A. (2009). SHMTool: a webserver for comparative analysis of somatic hypermutation datasets. DNA repair, 8(1), 137-141.

Maizels, N. (2005). Immunoglobulin gene diversification. Annu. Rev. Genet., 39, 23-46.
Martí-Renom, M. A., Stuart, A. C., Fiser, A., Sánchez, R., Melo, F., & Šali, A. (2000). Comparative protein structure modeling of genes and genomes. Annual review of biophysics and biomolecular structure, 29(1), 291-325.
Maul, R. W., & Gearhart, P. J. (2010). AID and somatic hypermutation. In Advances in immunology (vol. 105, pp. 159-191). Academic Press.
Maynard, J., & Georgiou, G. (2000). Antibody engineering. Annual review of biomedical engineering, 2(1), 339-376.
McGaughey, G. B., Gagné, M., & Rappé, A. K. (1998). π-Stacking interactions alive and well in proteins. Journal of Biological Chemistry, 273(25), 15458-15463.
Mian, I. S., Bradwell, A. R., & Olson, A. J. (1991). Structure, function and properties of antibody binding sites. Journal of molecular biology, 217(1), 133-151.
Midelfort, K. S., Hernandez, H. H., Lippow, S. M., Tidor, B., Drennan, C. L., & Wittrup, K. D. (2004). Substantial energetic improvement with minimal structural perturbation in a high affinity mutant antibody. Journal of molecular biology, 343(3), 685-701.
Muramatsu, M., Sankaranand, V. S., Anant, S., Sugai, M., Kinoshita, K., Davidson, N. O., & Honjo, T. (1999). Specific expression of activation-induced cytidine deaminase (AID), a novel member of the RNA-editing deaminase family in germinal center B cells. Journal of Biological Chemistry, 274(26), 18470-18476.
Norel, R., Sheinerman, F., Petrey, D., & Honig, B. (2001). Electrostatic contributions to protein-protein interactions: fast energetic filters for docking and their physical basis. Protein Science, 10(11), 2147-2161.
Novotný, J., Handschumacher, M., Haber, E., Bruccoleri, R. E., Carlson, W. B., Fanning, D. W., . . . & Rose, G. D. (1986). Antigenic determinants in proteins coincide with surface regions accessible to large probes (antibody domains). Proceedings of the National Academy of Sciences, 83(2), 226-230.
Ofran, Y. (2009). Prediction of protein interaction sites. Computational Protein-Protein Interactions, 167-184.
Ofran, Y., Schlessinger, A., & Rost, B. (2008). Automated identification of complementarity determining regions (CDRs) reveals peculiar characteristics of CDRs and B cell epitopes. The Journal of Immunology, 181(9), 6230-6235.
Ohue, M., Matsuzaki, Y., Uchikoga, N., Ishida, T., & Akiyama, Y. (2014). MEGADOCK: an all-to-all protein-protein interaction prediction system using tertiary structure data. Protein and peptide letters, 21(8), 766-778.
Olimpieri, P. P., Chailyan, A., Tramontane, A., & Marcatili, P. (2013). Prediction of site-specific interactions in antibody-antigen complexes: the proABC method and server. Bioinformatics, 29(18), 2285-2291.
Padlan, E. A., Abergel, C., & Tipper, J. P. (1995). Identification of specificity-determining residues in antibodies. The FASEB journal, 9(1), 133-139.
Pandit, S. B., & Skolnick, J. (2008). Fr-TM-align: a new protein structural alignment method based on fragment alignments and the TM-score. BMC bioinformatics, 9(1), 531.
Peled, J. U., Kuang, F. L., Iglesias-Ussel, M. D., Roa, S., Kalis, S. L., Goodman, M. F., & Scharff, M. D. (2008). The biochemistry of somatic hypermutation. Annu. Rev. Immunol., 26, 481-511.
Persson, H., Ye, W., Wernimont, A., Adams, J. J., Koide, A., Koide, S., . . . & Sidhu, S. S. (2013). CDR-H3 diversity is not required for antigen recognition by synthetic antibodies. Journal of molecular biology, 425(4), 803-811.
Petrey, D., & Honig, B. (2005). Protein structure prediction: inroads to biology. Molecular cell, 20(6), 811-819.
Pierce, B., & Weng, Z. (2007). ZRANK: reranking protein docking predictions with an optimized energy function. Proteins: Structure, Function, and Bioinformatics, 67(4), 1078-1086.
Potapov, V., Cohen, M., & Schreiber, G. (2009). Assessing computational methods for predicting protein stability upon mutation: good on average but not in the details. Protein engineering, design & selection, 22(9), 553-560.
Queen, C., Schneider, W. P., Selick, H. E., Payne, P. W., Landolfi, N. F., Duncan, J. F., . . . & Waldmann, T. A. (1989). A humanized

(56) References Cited

OTHER PUBLICATIONS antibody that binds to the interleukin 2 receptor. Proceedings of the National Academy of Sciences, 86(24), 10029-10033.

Retter, I., Althaus, H. H., Munch, R., & Müller, W. (2005). VBASE2, an integrative V gene database. Nucleic acids research, 33(suppl_1), D671-D674.

Ritchie, D. W., & Venkatraman, V. (2010). Ultra-fast FFT protein docking on graphics processors. Bioinformatics, 26(19), 2398-2405.

Robin, G., Sato, Y., Desplancq, D., Rochel, N., Weiss, E., & Martineau, P. (2014). Restricted diversity of antigen binding residues of antibodies revealed by computational alanine scanning of 227 antibody-antigen complexes. Journal of molecular biology, 426(22), 3729-3743.

Rost, B. (1999). Twilight zone of protein sequence alignments. Protein engineering, 12(2), 85-94.

Šali, A., Potterton, L., Yuan, F., van Vlijmen, H., & Karplus, M. (1995). Evaluation of comparative protein modeling by MODELLER. Proteins: Structure, Function, and Bioinformatics, 23(3), 318-326.

Schmidt, A. G., Xu, H., Khan, A. R., O'Donnell, T., Khurana, S., King, L. R., . . . & Settembre, E. C. (2013). Preconfiguration of the antigen-binding site during affinity maturation of a broadly neutralizing influenza virus antibody. Proceedings of the National Academy of Sciences, 110(1), 264-269.

Schneidman-Duhovny, D., Inbar, Y., Nussinov, R., & Wolfson, H. J. (2005). PatchDock and SymmDock: servers for rigid and symmetric docking. Nucleic acids research, 33(suppl_2), W363-W367.

Schymkowitz, J., Borg, J., Stricher, F., Nys, R., Rousseau, F., & Serrano, L. (2005). The FoldX web server: an online force field. Nucleic acids research, 33(suppl_2), W382-W388.

Sela-Culang, I., Alon, S., & Ofran, Y. (2012). A systematic comparison of free and bound antibodies reveals binding-related conformational changes. The Journal of Immunology, 189(10), 4890-4899.

Sela-Culang, I., Benhnia, M. R. E. I., Matho, M. H., Kaever, T., Maybeno, M., Schlossman, A., . . . & Crotty, S. (2014). Using a combined computational-experimental approach to predict antibody-specific B cell epitopes. Structure, 22(4), 646-657.

Sela-Culang, I., Kunik, V., & Ofran, Y. (2013). The structural basis of antibody-antigen recognition. Frontiers in immunology, 4, 302.

Shulman-Peleg, A., Nussinov, R., & Wolfson, H. J. (2005). SiteEngines: recognition and comparison of binding sites and protein-protein interfaces. Nucleic acids research, 33(suppl_2), W337-W341.

Sidhu, S. S., Li, B., Chen, Y., Fellouse, F. A., Eigenbrot, C., & Fuh, G. (2004). Phage-displayed antibody libraries of synthetic heavy chain complementarity determining regions. Journal of molecular biology, 338(2), 299-310.

Söderlind, E., Strandberg, L., Jirholt, P., Kobayashi, N., Alexeiva, V., Åberg, A. M., . . . & Danielsson, L. (2000). Recombining germline-derived CDR sequences for creating diverse single-framework antibody libraries. Nature biotechnology, 18(8), 852-856.

Tharakaraman, K., Robinson, L. N., Hatas, A., Chen, Y. L., Siyue, L., Raguram, S., . . . & Sasisekharan, R. (2013). Redesign of a cross-reactive antibody to dengue virus with broad-spectrum activity and increased in vivo potency. Proceedings of the National Academy of Sciences, 110(17), E1555-E1564.

Thom, G., Cockroft, A. C., Buchanan, A. G., Candotti, C. J., Cohen, E. S., Lowne, D., . . . & Minter, R. R. (2006). Probing a protein-protein interaction by in vitro evolution. Proceedings of the National Academy of Sciences, 103(20), 7619-7624.

Thorpe, I. F., & Brooks, C. L. (2007). Molecular evolution of affinity and flexibility in the immune system. Proceedings of the National Academy of Sciences, 104(21), 8821-8826.

Tina, K. G., Bhadra, R., & Srinivasan, N. (2007). PIC: protein interactions calculator. Nucleic acids research, 35(suppl_2), W473-W476.

Tokuriki, N., Stricher, F., Schymkowitz, J., Serrano, L., & Tawfik, D. S. (2007). The stability effects of protein mutations appear to be universally distributed. Journal of molecular biology, 369(5), 1318-1332.

Tokuriki, N., Stricher, F., Serrano, L., & Tawfik, D. S. (2008). How protein stability and new functions trade off. PLoS computational biology, 4(2) e1000002.

Tomlinson, I. M., Walter, G., Jones, P. T., Dear, P. H., Sonnhammer, E. L., & Winter, G. (1996). The imprint of somatic hypermutation on the repertoire of human germline V genes. J. Mol. Bio. 256:813-817.

Tovchigrechko, A., & Vakser, I. A. (2006). GRAMM-X public web server for protein-protein docking. Nucleic acids research, 34(suppl_2), W310-W314.

Wu, T. T., & Kabat, E. A. (1970). An analysis of the sequences of the variable regions of Bence Jones proteins and myeloma light chains and their implications for antibody complementarity. The Journal of experimental medicine, 132(2), 211-250.

* cited by examiner

FIG. 16

Binding contribution score

| | H1 | H2 | H3 | L1 | L2 | L3 |
|---|---|---|---|---|---|---|
| Contacting residues | 7 | 13 | 21 | 12 | 4 | 13 |
| Specific interactions | 0 | 2 | 5 | 2 | 0 | 3 |
| ddG | -0.91 | 1.43 | 8.04 | 3.87 | 1.43 | 6.48 |
| delta_ASA | 0.4 | 0.95 | 2.85 | 1.44 | 0.19 | 0.89 |
| Binding score | 4 | 9 | 16 | 9 | 5 | 12 |
| Independent epitope residues | 59.25% | | | | | |
| Integrated epitope residues | 11.1% | | | | | |

| | H1 | H2 | H3 | L1 | L2 | L3 |
|---|---|---|---|---|---|---|
| Contacting residues | 11 | 15 | 39 | 6 | 0 | 5 |
| Specific interactions | 1 | 3 | 6 | 0 | 0 | 0 |
| ddG | 2.48 | 0.55 | 12.62 | 1.48 | 0.03 | 1.32 |
| delta_ASA | 1.07 | 1.59 | 4.65 | 0.62 | 0 | 0.49 |
| Binding score | 5 | 7 | 16 | 4 | 4 | 4 |
| Independent epitope residues | 83.33% | | | | | |
| Integrated epitope residues | 5.55% | | | | | |

COMPUTER ASSISTED ANTIBODY RE-EPITOPING

CROSS-REFERENCE TO RELATED APPLICATIONS

This application is a National Phase Application of PCT International Application Number PCT/US2015/062768, International filing date Nov. 25, 2015, which claims the benefit of U.S. Provisional Application Ser. No. 62/085,205 and U.S. Provisional Application Ser. No. 62/085,210, both filed Nov. 26, 214; which are hereby incorporated by reference.

BACKGROUND OF THE INVENTION

Recombinant antibodies represent the fastest growing class of therapeutic medicines, and the generation of antibodies that meet specific criteria is increasingly important for therapeutic applications. Currently, there are two predominant methodologies for therapeutic antibody generation: immunization-based and surface display-based approaches. These methodologies are responsible for the majority of the currently marketed therapeutic antibodies and for the biopharma industry pipeline which are concentrated on only a small number of targets. A key challenge for the broader application of biotherapeutic approaches is the difficulty of raising functional antibodies against novel targets. Since many new targets are membrane spanning and multimeric proteins, there is a need to develop more effective methods to generate antibodies against these difficult targets. Also, the pharmaceutical properties of therapeutic antibodies are an active area for study concentrating on biophysical characteristics such as thermal stability and aggregation.

Of the currently approved antibody therapeutics, many are humanized rodent antibodies. Although obtaining fully human antibodies from phage displayed human antibody libraries or from transgenic rodents with human antibody genes are more popular techniques today, rodents with wild-type immunoglobulin genes remain an important source for therapeutic antibody discovery. Some industrial laboratories have been able to obtain antibodies with low picomolar affinity, thus providing good candidates for therapeutic antibody engineering, such as humanization. A major challenge to immunization-based antibody discovery is related to the nature of new targets themselves, many of which are membrane-spanning proteins. Therefore, conventional biochemistry in preparing soluble protein as immunogens does not work well for this target class. Also, immune tolerance can lead to difficulties generating neutralizing antibodies when antigens are well conserved or are toxic upon administration to animals. Specific, immunodominant epitopes may be preferentially selected, making it difficult to identify functional antibodies.

Display technologies such as phage, yeast and ribosome display are based on the in vitro selection of antibody fragments from libraries and overcome some of the limitations of immune tolerance or epitope dominance in vivo. However, selection from such libraries may not always generate high-affinity antibodies without subsequent affinity maturation. Moreover, these methods typically select the tightest binders, regardless of the epitope they bind, which often results in isolating non-functional antibodies. Furthermore, antibody fragments isolated from microbial display systems are not always easily reformatted to produce well-expressed IgGs, soluble enough to be formulated for subcutaneous delivery.

Mammalian cell expression systems offer a number of potential advantages for therapeutic antibody generation, including the ability to co-select for key manufacturing-related properties such as high-level expression and stability, while displaying functional glycosylated IgGs on the cell surface. However, mammalian cell display has been hampered by the smaller library sizes that can be screened, making direct isolation of high-affinity binders from naïve libraries improbable. Although small libraries biased toward a particular antigen have been used successfully, a more generalized approach to generate high-affinity human antibodies from immunologically naïve libraries has not been reported. Importantly, mammalian display systems are also designed to select fragments with higher affinity that are not necessarily functional.

Stability and aggregation level are two critical factors that affect the pharmaceutical properties of biologic drugs, including protein production, formulation, shelf-life, dosing route, in vivo half-life and immunogenicity. Both sequence and structure based approaches have been applied in attempts to improve biotherapeutic stability. Sequence based analyses such as germline analysis, sequence conservation analysis, and sequence covariance analysis have all revealed potential amino acid changes to improve protein stability. Structure-based engineering attempts to stabilize fragile regions have involved inserting extra stabilizing interactions or eliminating incompatible interactions.

Antibodies (Abs) have two distinct functions: one is to bind specifically to their target antigen (Ag); the other is to elicit an immune response against the bound Ag by recruiting other cells and molecules. The association between an Ab and an Ag involves a myriad of non-covalent interactions between the epitope—the binding site on the Ag, and the paratope—the binding site on the Ab. The ability of Abs to bind virtually any non-self surface with exquisite specificity and high affinity is not only the key to immunity but has also made Abs an enormously valuable tool in experimental biology, biomedical research, diagnostics and therapy. The diversity of their binding capabilities is particularly striking given the high structural similarity between all Abs. The availability of increasing amounts of structural data in recent years now allows for a much better understanding of the structural basis of Ab function in general, and of Ag recognition in particular.

Antibody-Antigen (Ab-Ag) interactions are based on non-covalent binding between the antibody (Ab) and the antigen (Ag). Correct identification of the residues that mediate Ag recognition and binding improves our understanding of antigenic interactions and permits the modification and manipulation of Abs. For example, introducing mutations into the V-genes has been suggested as a way to improve Ab affinity. (Crameri A et al., *Nat Med* 2: 100-102 (1996); Figini M. et al. *J Mol Biol* 239: 68-78 (1994); Hawkins, R. E. et al., *J Mol Biol* 226: 889-896 (1992). However, mutations in the framework regions (FRs) rather than in the Ag binding residues themselves are more likely to evoke an undesired immune response. (Lou, J. et al. "Affinity Maturation by Chain Shuffling and Site Directed Mutagenesis" in ANTIBODY ENGINEERING (New York: Springer) 377-396 (2010)). Knowing which residues are more likely to bind the Ag can help direct such mutations and be beneficial to Ab engineering. (Almagro, J. C., *J Mol Recognit* 17: 132-143 (2004); Gonzales, N. R. et al., *Mol Immunol* 41: 863-872 (2004); Padlan, E. A. et al. *Faseb J* 9: 133-139 (1995)).

It has been shown that Ag binding residues are primarily located in the complementarity determining regions (CDRs). (Padlan, E. A. et al., *Faseb J* 9: 133-139; MacCallum, R. M. et al., *J Mol Biol* 262: 732-745 (1996); Wu, T. T. et al., *J Exp Med* 132: 211-250 (1970)). Thus, the attempt to identify CDRs, and particularly the attempt to define their boundaries, has become the focus of extensive research over the last few decades. (Padlan, E. A. et al. *Faseb J* 9: 133-139 (1995); MacCallum, R. M. et al., *J Mol Riot* 262: 732-745 (1996); Zhao, S. et al. *Mol Immunol* 47: 694-700 (2010)); Kabat and co-workers attempted to systematically identify CDRs in newly sequenced Abs. (Wu, T. T., and Kabat, E. A., *J Exp Med* 132: 211-250 (1970); Kabat, E. A. et al., "Sequence of proteins of immunological interest", Bethesda: National Institute of Health 323 (1983)). Their approach was based on the assumption that CDRs include the most variable positions in Abs and therefore could be identified by aligning the fairly limited number of Abs available then. Based on this alignment, they introduced a numbering scheme for the residues in the hypervariable regions and determined which positions mark the beginning and the end of each CDR. The Kabat numbering scheme was developed when no structural information was available. Chothia et al. analyzed a small number of Ab structures and determined the relationship between the sequences of the Abs and the structures of their CDRs. (Chothia, C. et al., *J Mol Biol* 196: 901-917 (1987); Chothia, C. et al., *Nature* 342: 877-883 (1989)). The boundaries of the FRs and the CDRs were determined and the latter have been shown to adopt a restricted set of conformations based on the presence of certain residues at key positions in the CDRs and the flanking FRs. This analysis suggested that the sites of insertions and deletions in CDRs L1 and H1 are different than those suggested by Kabat. Thus, the Chothia numbering scheme is almost identical to the Kabat scheme, but based on structural considerations, places the insertions in CDRs L1 and H1 at different positions. As more experimental data became available, the analysis was performed anew, re-defining the boundaries of the CDRs. These definitions of CDRs are mostly based on manual analysis and may require adjustments as the structure of more Abs become available. Abhinandan et al. aligned Ab sequences in the context of structure and found that approximately 10% of the sequences in the manually annotated Kabat database have erroneous numbering. (Abhinandan, K. R. et al., *Mol Immunol* 45: 3832-3839A (2008)). A more recent attempt to define CDRs is that of the IMGT database which curates nucleotide sequence information for immunoglobulins (IG), T-cell receptors (TcR) and Major Histocompatibility Complex (MHC) molecules. (Lefranc, M. P. et al., *Dev Comp Immunol* 27: 55-77. (2003)). It proposes a uniform numbering system for IG and TcR sequences, based on aligning more than 5000 IG and TcR variable region sequences, taking into account and combining the Kabat definition of FRs and CDRs, structural data, and Chothia's characterization of the hypervariable loops. Their numbering scheme does not differentiate between the various immunoglobulins (i.e., IG or TcR), the chain type (i.e., heavy or light) or the species.

A drawback of these numbering schemes is that CDR length variability is accommodated with either annotation of insertion (Kabat and Chothia) or by providing excess numbers (IMGT). Abs with unusually long insertions may be hard to annotate this way, and therefore their CDRs may not be identified correctly. Honegger and Pluckthun suggested a structurally improved version of the IMGT scheme. (Honegger, A. et al., *J Mol Biol* 309: 657-670 (2001)). Instead of introducing unidirectional insertions and deletions as in the IMGT and Chothia schemes, they were placed symmetrically around a key position. MacCallum et al. have proposed focusing on the specific notion of Ag binding residues rather than the more vague concept of CDRs. (MacCallum, R. M. et al., *J Mol Biol* 262: 732-745 (1996)). They suggested that these residues could be identified based on structural analysis of the binding patterns of canonical loops. Other studies have dubbed those Ag binding residues Specificity Determining Regions (SDRs). (Almagro, J. C. et al., *J Mol Recognit* 17: 132-143 (2004); Padlan, E. A. et al., *Faseb J* 9: 133-139 (1995)).

The specificity of the Ab molecule to its cognate Ag has been exploited for the development of a variety of immunoassays, vaccinations, and therapeutics. Ab engineering may offer to expand the application of Abs by permitting improvements of affinity (Marks, J. D. et al. *Biotechnology* 10:779-8310 (1992); Soderlind, E. et al., *Immunotechnology* 4:279-85 (1999)) and specificity (Hemminki, A. et al., *Immunotechnology* 4:59-69 (1998); Ohlin, M. et al., *Mol Immunol* 33:47-56 (1996)). Understanding of the role each structural element in the Ab plays in Ag recognition is essential for successful engineering of better binders. The engineering of Abs is also important for the clinical use of Abs from non-human sources. Early studies on the use of rodent Abs in humans determined that they can be immunogenic (Mirick, G. R. et al., *Q J Nucl Med Mol Imaging* 48:251-7 (2004)). Humanization by grafting of the CDRs from a mouse Ab to a human FR is a commonly used engineering strategy for reducing immunogenicity (Jones, P. T. et al., *Nature* 321:522-510 (1986); Queen, C. et al., *Proc Natl Acad Sci USA* 86:10029 (1989)). In most cases, the successful design of high-affinity, CDR-grafted, Abs requires that key residues in the human acceptor FRs that are crucial for preserving the functional conformation of the CDRs will be back-mutated to the amino acids of the original murine Ab (Queen, C. et al., *Proc Natl Acad Sci USA* 86:10029 (1989); Co, M. S. et al., *Nature* 351:501 (1991). Several groups (Padlan, E. A. et al., *FASEB J* 9:133-9 (1995); Ofran Y. et al., *J Immunol* 181:6230-5 (2008); Kunik, V. et al., *PLoS Comput Biol* 8 (2012)) used the experimentally determined 3-D structures of Ab-Ag complexes in the Protein Data Bank (PDB) (Berman, H. M. et al., "The Protein Data Bank" *Nucleic Acids Res* 28:235 (2000) (hereby incorporated by reference in its entirety) to determine which residues participate in Ag recognition and binding. Such knowledge can be exploited to identify residues that are important for the function of the Ab in general and for Ag recognition in particular, and may guide Ab engineering (Haidar, J. N. et al., *Proteins* 80:896-912 (2012); Hanf, K. J. et al., *Methods* 10 (2013) (hereby incorporated by reference in their entirety)). Residues that help maintain the functional conformation of the CDRs, for example, can be used to improve Ab humanization efforts by CDR-grafting.

More recent studies have shown that virtually all Ag binding residues fall within regions of structural consensus. (Kunik, V. et al., PloS Computational Biology 8(2): e1002388 (February 2012)) (hereby incorporated by reference in its entirety). These regions are referred to as Ag Binding Regions (ABRs). It was shown that these regions can be identified from the Ab sequence as well. "Paratome", an implementation of a structural approach for the identification of structural consensus in Abs, was used for this purpose. (Ofran, Y. et al., *J. Immunol.* 181:6230-6235 (2008)) (hereby incorporated by reference in its entirety). While residues identified by Paratome cover virtually all the Ag binding sites, the CDRs (as identified by the commonly used CDR identification tools) miss significant portions of them. Ag binding residues which were identified by Paratome but were not identified by any of the common CDR identification methods are referred to as Paratome-unique residues. Similarly, Ag binding residues that are identified by any of the common CDR identification methods but are not identified by Paratome are referred to as CDR-unique residues. Paratome-unique residues make crucial energetic contribution to Ab-Ag interactions, while CDRs-unique residues have a rather minor contribution. These results allow for better identification of Ag binding sites and thus for better identification of B-cell epitopes. They may also help improve vaccine and Ab design.

B cells are activated during exposure to pathogens, and produce antibodies (Abs) that bind specific antigens (Ags). The initial repertoire of germline Abs is generated by rearrangement of the V(D)J gene segment. (Maizels, N., *Annu Rev Genet* 39, 23-46 (2005)). These Abs are the first responders to the Ag, and are believed to bind Ag with low affinity. (Di Noia, J. M. & Neuberger, M. S., *Annu Rev Biochem* 76, 1-22 (2007)). Improvement of affinity occurs in the days after the initial exposure through introduction of high-rate base changes in the Ab sequence, known as somatic hypermutations (SHMs), and selection of B-cell clones that have better affinity toward the Ag. (Rajewsky, K., *Nature* 381: 751-758 (1996)). The SHM process enables development of an efficient secondary response and immunological memory, which is key to development of B-cell immunity. Investigating SHMs is therefore essential for understanding the immune system and can guide Ab engineering, thus improving development of Abs as research, diagnostic and therapeutic agents.

BRIEF SUMMARY OF THE INVENTION

In one embodiment, the claimed invention is directed to a method for generating a library of antigen binding molecules for screening for binding to an epitope of interest, the method comprising:
 a. selecting a template antigen-binding molecule from a set of possible template antigen binding molecules wherein said selected template does not specifically bind the epitope of interest but is known to specifically bind another epitope;
 b. selecting at least one residue position in said template antigen-binding molecule for mutation; and
 c. selecting at least one variant residue to substitute at the at least one residue position selected in b;
 such that a library containing a plurality of variants of said template is generated. In another embodiment, the method further comprises synthesizing the template variants to form the library. In some embodiments, the set of possible template antigen-binding molecules comprises a plurality of known antibodies that do not bind the epitope of interest.

In some embodiments, the step of selecting a template antigen-binding molecule comprises screening the three-dimensional structures of the set of possible antigen-binding molecules based on one or more of the following criteria: shape complementarity to the epitope of interest, physicochemical complimentarity to the epitope of interest, and the predicted free energy of the interaction with the epitope of interest. In some embodiments, the step of selecting a template antigen-binding molecule further comprises screening the three-dimensional structures of the set of possible antigen-binding molecules based on physicochemical complimentarity to the epitope of interest. In another embodiment, the step of selecting a template antigen-binding molecule further comprises screening the three-dimensional structures of the set of possible antigen-binding molecules based on the predicted free energy of the interaction with the epitope of interest.

In some embodiments, the step of selecting at least one residue position comprises screening the three-dimensional structure of the template antigen-binding molecule to identify residues likely to contribute to binding to the epitope of interest. In another embodiment, the step of selecting at least one residue position comprises conducting multiple sequence alignment of the nucleic acid sequence of the template antigen-binding molecule to identify substitutable positions.

In certain embodiments, the step of selecting at least one variant residue comprises, for each residue identified in step b above, identifying substitutions that are preferred, allowed and/or neutral at that residue position. The preferred, allowed and/or neutral substitutions can be determined by analyzing the sequences of a plurality of known antibodies derived from the same germline sequences as the template antigen-binding molecule. In one embodiment, the step of selecting at least one variant residue further comprises synthesizing variants of the template antigen-binding molecule to form a library.

The claimed invention is also directed to a library of antigen-binding molecules made by one or more of the above method(s).

In another embodiment, the invention is directed to screening the library with the antigen of interest to select for antigen-binding molecules that have desired properties (e.g., binding affinity, stability, etc.)

In another embodiment, the invention is directed to an antigen-binding molecule isolated from said library after said screening.

In another embodiment, the claimed invention is directed to a method for screening a library of antigen-binding molecules, comprising
 a. screening said library with an epitope of interest to identify antigen-binding molecules that bind said epitope of interest;
 b. sequencing the binders identified in step a. to determine which residues are enriched and which are depleted;
 c. using the information from step b. to synthesize an optimized library of variants of the binders; and
 d. repeating steps a-c using the optimized library.

In one embodiment, the at least one residue selected for mutation is in a CDR region of the template. In a preferred embodiment, the antigen-binding molecules are antibodies and the residues selected for mutation are in less than all of the CDRs, or in regions outside of the CDR that are likely to affect antigen binding.

In certain embodiments, the methods of the invention are computer implemented. Thus, the invention is also directed to a database on a computer readable medium comprising the three-dimensional structure of a plurality of known antigen-binding molecules. In one embodiment, the invention is directed to a method for generating a library of antigen binding molecules for screening for binding to an epitope of interest, said method comprising:
 a. executing a computer program to select a template antigen-binding molecule from a set of possible template antigen-binding molecules, wherein said selected template does not specifically bind the epitope of interest but may be known to specifically bind another epitope;
 b. selecting at least one residue position in said template antigen-binding molecule for mutation;
 c. selecting at least one variant residue to substitute at the at least one residue position selected in b;

such that a library containing a plurality of variants of said template is generated.

BRIEF DESCRIPTION OF THE DRAWINGS/FIGURES

FIG. 1: Iterative process of re-epitoping existing antibodies to bind a preselected epitope on an antigen.

FIG. 2. Hotspot motifs and occurrence of SHMs. (A) The fraction of the germline occurrences of an amino acid that are mutated during SHM versus the fraction of its occurrences that fall within a DNA hotspot motif is shown in a scatter plot. The y value for each data point is the proportion of a specific amino acid in a hotspot motif (RGYW or WRCY). The x value for each data point is the proportion of a specific amino acid that was mutated during the SHM process. The proportions in both cases are calculated relative to the total number of the specific amino acid in the germline sequences (V and J segments) of the 196 Abs in the dataset. (B) The distance of the middle codon from the nearest hotspot motif was calculated (see 'Experimental procedures') for each amino acid or mutation up to position 105 (according to IMGT numbering) in the V gene. The distances for mutations (gray line) or amino acids (black line) in the V gene are presented in a histogram using bins of 1 base wide.

FIG. 3. Mutation propensity and energy contribution of the various Ab structural regions. (A) The Ab residues were divided into their structural regions, as demonstrated by coloring of a representative structure of Ab 1F9 against turkey egg white lysozyme C. The image was generated from PDB ID 1DZB using Discovery Studio Visualizer (Accelrys, San Diego, Calif.). The Ag is shown in grey on top. The Ab variable region is shown also in ribbon representation marked according to the structural group: Ag interface in *, VHVL interface in A, both interfaces in #, ABRs (CDRs) that are not in interfaces in o, and other residues in gray. (B) The ΔΔG values for substitution of each SHM back to its germline amino acid were calculated using FoldX (see 'Experimental procedures'). The ΔΔG values are presented in a histogram using bins of 1 kcal·mol$^{-1}$ wide, with each region marked as described above. (C) The percentage of residues in each region out of all residues in the variable regions (C) are shown in pie charts.

FIG. 4. SHM contacting residues, germline contacting residues and protein-protein interfaces. The data for SHM contacting residues are shown in dark gray (A-C), those for germline contacting residues are shown in light gray (A-C) and those for protein-protein interfaces are shown in white bars (C). (A) Binding site composition according to the origin of the contacting residues. (B) The ΔΔG values for substitution of each contacting residue by alanine were calculated using FoldX (see 'Experimental procedures'). The ΔΔG values are presented in a histogram using bins of 1 kcal·mol$^{-1}$ wide. (C) For the amino acid composition, the amino acids are listed on the x axis and the y values are the amino acid frequency in the contacting residues. Error bars represent the standard error. (D) The similarity between the amino acids compositions was calculated using Jensen-Shannon divergence.

FIG. 5. Propensities of amino acids to be mutated during affinity maturation. The 'propensity to be mutated' (see 'Experimental procedures') for each amino acid in the various structural regions is shown. Error bars represent the standard error. The structural regions are marked as follows: Ag interface marked as *, VHVL interface marked as Δ, both interfaces marked as #, and ABRs that are not in interfaces marked as o.

FIG. 6. Amino acid composition of SHMs in the various structural regions. The amino acid composition of newly introduced residues was calculated as described in the text. Error bars represent the standard error.

The structural regions are marked as follows: Ag interface marked as *, VH-VL interface marked as Δ, both interfaces marked as #, and ABRs that are not in interfaces are marked as o.

FIG. 7. Mean ΔΔG value and mutation probability for each Ab position. Ab positions are numbered according to the IMGT numbering for the V domain (Lefranc M P, Pommie C, Ruiz M, Giudicelli V, Foulquier E, Truong L, Thouvenin-Contet V & Lefranc G (2003) IMGT unique numbering for immunoglobulin and T cell receptor variable domains and Ig superfamily V-like domains, *Dev Comp Immunol* 27, 55-77.) The Ab positions in the VH domain (A) and the VL domain (B) are indicated on the x axis. The mutation probability is represented by asterisks, and was calculated as the number of mutations in a specific position divided by the number of appearances of any amino acid in this specific position. If for a given position, the number of appearances of any amino acid was ≤5, it was excluded from the figure. The mean ΔΔG values for each position was calculated from the ΔΔG values for substitution of each SHM in the relevant position back to its germline amino acid. The mean ΔΔG value is represented by gray bars, with error bars indicating standard error. The CDR positions according to IMGT definitions Lefranc M P, Pommie C, Ruiz M, Giudicelli V, Foulquier E, Truong L, Thouvenin-Contet V & Lefranc G (2003) IMGT unique numbering for immunoglobulin and T cell receptor variable domains and Ig superfamily V-like domains. *Dev Comp Immunol* 27, 55-77. are enclosed in gray boxes.

FIG. 8: Amino acids preference to be mutated during affinity maturation. The amino acids are listed over the x axis and the y values are the preferences. AA1 gl group→X mature group is the number of changes from specific amino acid to any amino acid in the group.

$$\frac{AA1gl\text{ group}}{\text{total }aagl\text{ group}}$$

is the frequency of a specific amino acid in the germ-line sequences of the group. mutations in group is the number of mutations in the group. Standard errors are presented by the error bars FIG. 9: Average antigen binding ΔΔG and mutation probability per antibody position. Antibody positions of VH(a) and VL(b) are listed over the X axis. The average ΔΔG is represented by bars together with standard error markings that were calculated for each position. Number of mutations is represented by asterisks.

FIG. 10: Yeast surface display (YSD) was used to demonstrate the blocking of IL17Ra binding by our designs. Cells were incubated with 40 nM biotinylated IL17a, without ("+IL17a") or with 120 nM IL17Ra ("+IL17a+receptor") or without any recombinant protein ("No IL17a"). Cells were then stained with streptavidin-APC conjugate and analyzed using a flow cytometry apparatus. Results displayed as a histogram of fluorescence (from the APC channel) distribution among the population.

FIG. 11: The ability of designed scFv to block IL17a: IL17Ra complex was tested after pre-incubated for 1 h at the designated temperatures. The assay was done at a concentration that gives 50% blocking w/o preincubation.

FIG. 12: Flowchart depicting an embodiment of the procedure for designing a library of the invention.

FIG. 13: Average ΔΔG and mutation probability per Ab position. Ab positions are according to IMGT unique numbering for V-domain [44]. The Ab positions of the VH (A) and VL (B) domains are listed over the X axis. Mutation probability is represented by asterisks and was calculated as the number of mutations in a specific position divided by the number of appearances of any amino acid in this specific position. If for a given position, the number of appearances of any amino acid was <=5, it was excluded from the figure. The average ΔΔG for each position was calculated out of the ΔΔG values for substitution of each SHM in the relevant position beck to its germ-line amino acid. The average ΔΔG is represented by gray bars with error bars for standard error. The CDRs positions according to IMGT definitions are enclosed in gray rectangles.

FIG. 14: mutation probability vs Ab residue position: the probability of finding a mutation at a given position in the variable region of the human VH(A) and VL(B) domains and mouse VH(c) and VL(d) domains. If the number of appearances of an amino acid in a specific position was equal or less than five, it was omitted from the figure. Residue numbering and probability calculation are described in the Methods section. Gray bars are the mutations probabilities for CDR positions (IMGT definitions) and black empty bars are the mutations probabilities for CDRH4 positions in human VH domain.

FIG. 15: The ΔΔG distribution of SHMs. The ΔΔG values for the substitution of each SHM beck to its germ-line amino acid were calculated using FoldX. The ΔΔG values for mutations in the VH (black broken line) or in the VL (gray line) are presented in histogram by bins of 1 kcal/mole wide.

Figure 16:
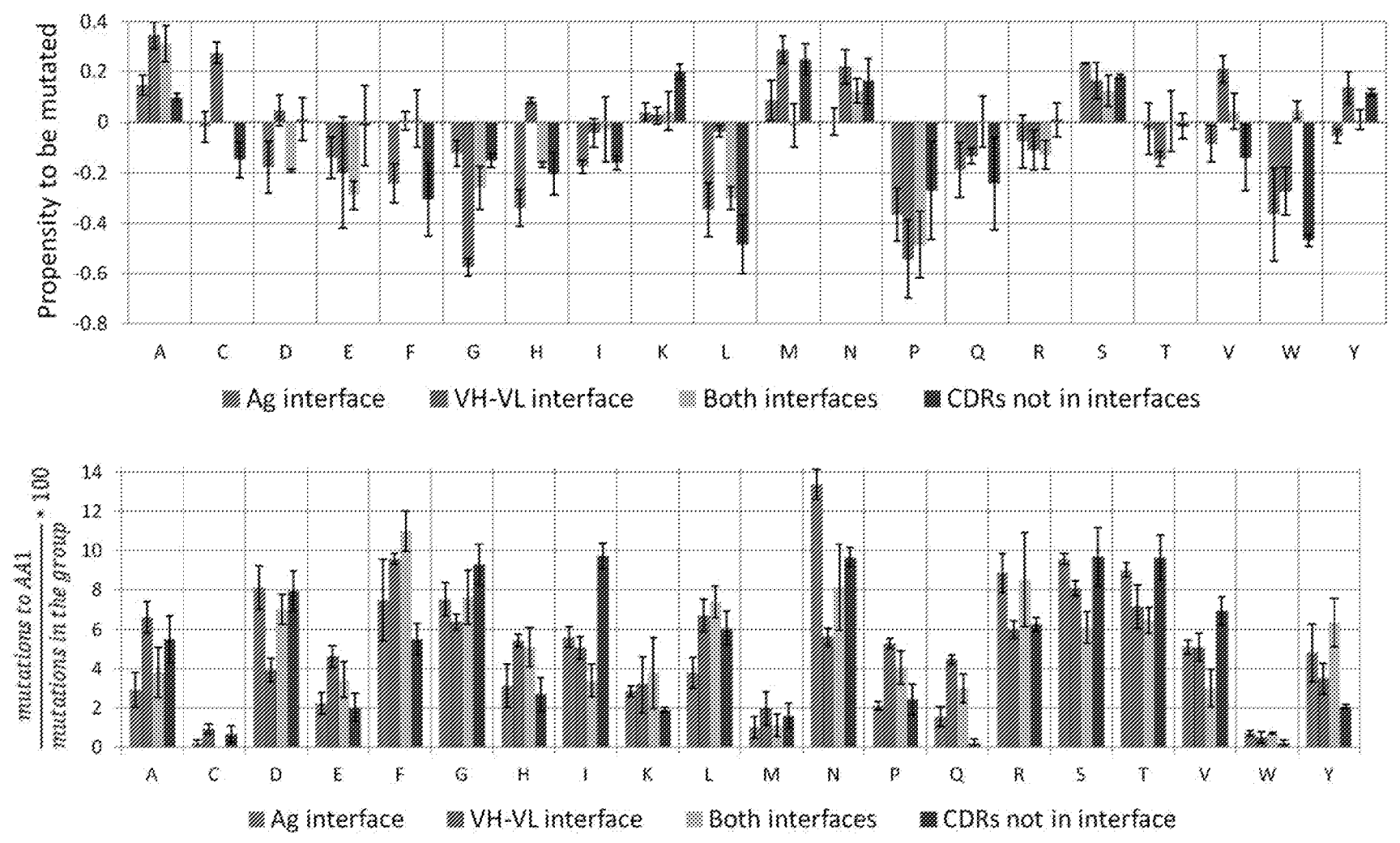

FIG. 16: the preference of removing a certain amino acid, or introducing a certain amino acid is presented here. The top histogram shows the preference of removing a certain amino acid based on its position in the antibody. The bottom histogram shows the preference of introducing a new amino acid based on its position in the antibody. These are design principles for SHM based library.

FIG. 17: CDRH4 loop in the Ab VH domain: Ab-Ag complex (PDBID: 3GBM) is shown in ribbon representation. The heavy and light variable regions are in the bottom and the Ag is at the top. CDRH4 is (bottom) denoted as stripes and the Ag-residues in contact (top) with it (less than six Å) are denoted as stripes.

FIG. 18: The binding contribution score of CDRs in natural and synthetic Abs—Binding contribution score (varies between 4 to 16) of each CDR in each Ab-Ag complex was calculated using the "CDRs Analyzer". On the Y axis are the average scores of a given CDR across all of the natural (white bars) or synthetic (gray bar) Ab-Ag complexes. Error bars represent standard errors.

FIG. 19: Distribution of H-bonds, salt-bridges and cation-pi across the CDRs-Percentage of salt-bridges, H-bonds and cation-pi interactions (top to bottom) that occur in each CDR in natural Abs and synthetic Abs. Labels are composed of CDR name (e.g. H1,L2) and the percentage of the specific interaction that are from residues in this CDR.

FIG. 20: Complexity of Ab-Ag interactions in terms of independent and integrated epitope residues—The average percentage of independent residues in the epitope, i.e. contacting only residues from one CDRs, are shown for the entire Ab (A) and for the six CDRs of the two groups (B). The average percentage of the integrated residues in the epitope, i.e. contacting residues from at least three CDRs, are shown for natural Ab and synthetic Abs (C) and for six CDRs of the two groups (D). An Integrated residue in the epitope was attributed to a certain CDR if the residue contacts that CDR and at least two other CDRs. Error Bars represent standard errors.

FIG. 21: Natural and synthetic Ab-Ag interaction—The crystal structure of the complex between hemagglutinin (HA) and the natural 2D1 Ab (PDBID: 3LZF) (A) and the crystal structure of the complex between membrane-type serine protease 1 (MT-SP1) and the synthetic E2 Abs (PDBID: 3BN9) are shown. The Ags are presented in surface view. The Abs are presented as a ribbon wherein non CDRs residues and the CDRs in the ribbon are represented based on the binding contribution score of the CDR from low contribution to high contribution. Each Ab-Ag complex is accompanied by a table, detailing the calculated parameters, the binding contribution score and the percent of independent and integrated epitope residues.

FIG. 22: Amino acid composition of the heavy chain CDRs of natural and synthetic Abs. Amino acid composition of CDRH1 (A). Amino acid composition of CDRH2 (B). Amino acid composition of CDRH3 (C).

FIG. 23: Frequency of charged and polar amino acids in the heavy chain CDRs of natural and synthetic Abs. The summed frequency of charged amino acids (D,E,H,K and R) for the three CDRs of the heavy chain (A). The frequency of charged amino acids in CDRH2 (B). The summed frequency of polar amino acids (M,N,Q,S,T,W and Y) for the three CDRs of the heavy chain (C).

DETAILED DESCRIPTION OF THE INVENTION

Definitions

Figure 1:
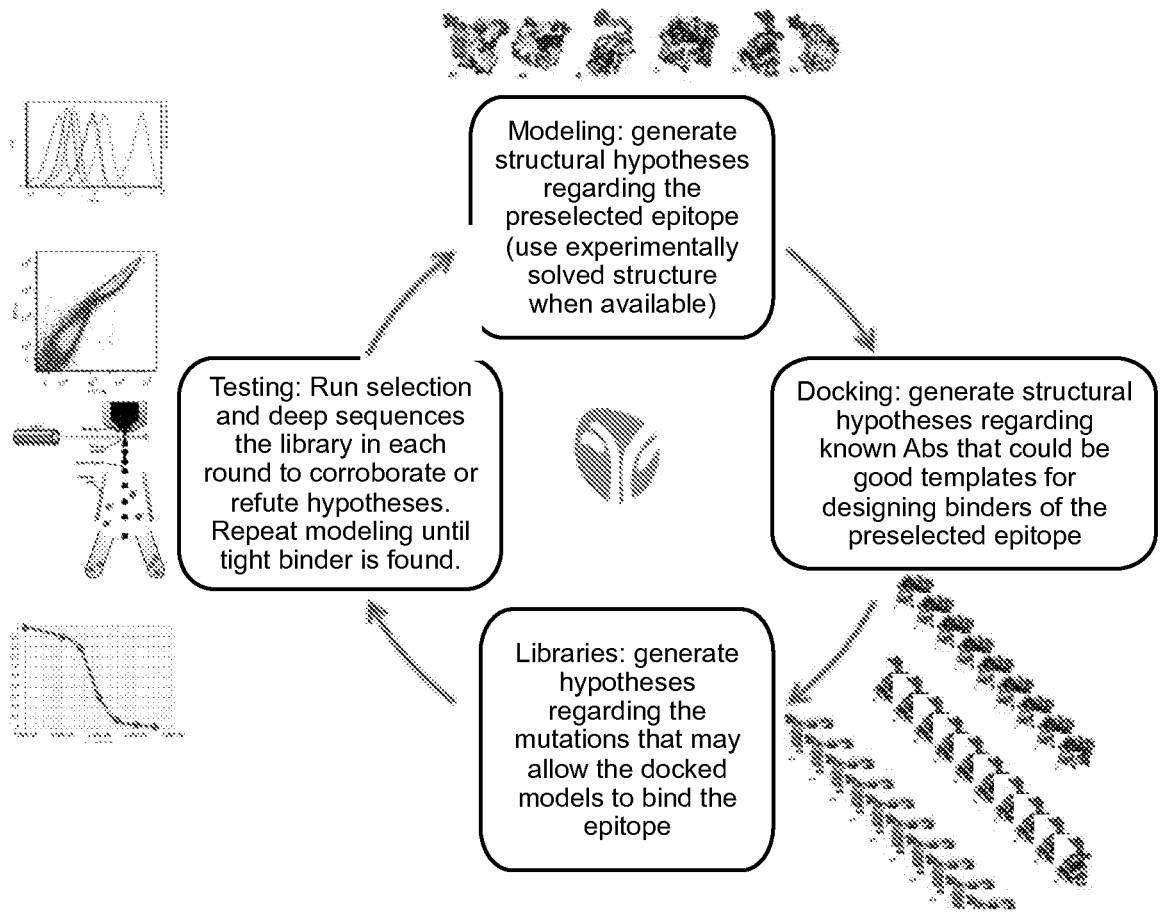

As used herein, the term "antigen binding molecule" refers in its broadest sense to a molecule that specifically binds an antigenic determinant. An antigen binding molecule can be, for example, an antibody or a fragment thereof that specifically binds to an antigenic determinant. By "specifically binds" is meant that the binding is selective for the antigen of interest and can be discriminated from unwanted or nonspecific interactions.

As used herein, the term "antibody" is intended to include whole antibody molecules, including monoclonal, polyclonal and multispecific (e.g., bispecific) antibodies, Also encompassed are antibody fragments that retain binding specificity including, but not limited to, VH fragments, VL fragments, Fab fragments, F(ab')$_2$ fragments, scFv fragments, Fv fragments, minibodies, diabodies, triabodies, and tetrabodies (see, e.g., Hudson and Souriau, Nature Med. 9: 129-134 (2003) (hereby incorporated by reference in their entirety)). Also encompassed are humanized, primatized and chimeric antibodies.

As used herein, the term "variant" refers to a polypeptide differing from a specifically recited polypeptide of the invention by amino acid insertions, deletions, and/or substitutions, created using, e.g., recombinant DNA techniques. Variants of the antigen binding molecules of the present invention include antigen binding molecules wherein one or several of the amino acid residues are modified by substitution, addition and/or deletion in such manner that does not substantially affect antigen binding affinity (that is, the affinity remains within one order of magnitude of the affinity of another variant). Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence amino acids.

As used herein, "shape complementarity" means the 3D shapes, either as detected experimentally or through homology modeling or through de-novo modeling, of the interacting surfaces fit each other without clashes or steric hindrances.

As used herein, "physico-chemical complementarity" means alignments of complementary charges, pi-pi interactions, donors and/or acceptors of H-bonds and any other molecular interactions that stabilize the complex.

As used herein, "substitutable positions" means positions in the antibody that, according to sequence and structure analysis, may be substituted without compromising the structure, expression stability or other characteristics of the antibody other than what it can bind.

As used herein, "preferred substitution" means that variability in a given position occurs more than expected by chance when comparing similar sequences.

As used herein, "neutral substitution" means that variability in a given position occurs as expected by chance when comparing similar sequences.

As used herein, "allowed substitution" means that variability in a given position occurs less than expected by chance when comparing similar sequences.

As used herein, "enriched residues" and "depleted residues" are determined as follows: The propensity of each amino acid in a given position in the original library determines the expected distribution of amino acids in this position, assuming that the position does not affect binding. After one or more rounds of selection, the observed propensities of amino acids in that position are recorded. If, by a predefined statistic, e.g. measuring the observed frequency compared to expected frequency using a measure such as log-odds, a certain amino acid is observed significantly more frequently than expected under the null hypothesis, then the amino acid is said to be enriched in that position. If it appears significantly less, it is said to be depleted.

Protein-protein docking is a computational method used to predict the structure of macromolecular complexes by orienting the three dimensional structures of two binding partners relative to each other, a goal of which is to accurately model the binding interface. A variety of algorithms can be utilized to sample the rotational and translational search space, including Fast Fourier Transform (Comeau, S. R., et al., ClusPro: a fully automated algorithm for protein-protein docking: *Nucleic Acids Res*, v. 32, p. W96-9 (2004); Ohue, M., et al., MEGADOCK: an all-to-all protein-protein interaction prediction system using tertiary structure data: *Protein Pept Lett*, v. 21, p. 766-78 (2014); Tovchigrechko, A., and I. A. Vakser, GRAMM-X public web server for protein-protein docking: *Nucleic Acids Res*, v. 34, p. W310-4 (2006)) (each of which is hereby incorporated by reference in its entirety), geometric hashing (Schneidman-Duhovny, D., et al., PatchDock and SymmDock: servers for rigid and symmetric docking: *Nucleic Acids Res*, v. 33, p. W363-7 (2005)) (hereby incorporated by reference in its entirety), Spherical polar Fourier (Ritchie, D. W., and V. Venkatraman, 2010, Ultra-fast FFT protein docking on graphics processors: *Bioinformatics*, v. 26, p. 2398-405) (hereby incorporated by reference in its entirety) Monte Carlo Search (Gray, J. J., et al. Protein-protein docking with simultaneous optimization of rigid-body displacement and side-chain conformations: *J Mol Biol*, v. 331, p. 281-99 (2003); Huang, S. Y., Search strategies and evaluation in protein-protein docking: principles, advances and challenges: *Drug Discov Today, v.* 19, p. 1081-1096 (2014)) (each of which is hereby incorporated by reference in its entirety). The key to successful protein-protein docking is the ability to select native or near-native structures from the thousands of docking poses the search algorithm generates, which is not a trivial challenge (Huang, S. Y., Search strategies and evaluation in protein-protein docking: principles, advances and challenges: *Drug Discov Today*, v. 19, p. 1081-1096 (2014); Moal, I. H., et al., Scoring functions for protein-protein interactions: *Curr Opin Struct Biol*, v. 23, p. 862-7 (2014)) (each of which is hereby incorporated by reference in its entirety). To select docking poses, different scoring functions can be implemented to rank the set of docking poses, for example, optimizing shape complementarity, energy functions (vdw, electrostatics, desolvation), binding free energies, and statistical potentials (Chen, R., et al., ZDOCK: an initial-stage protein-docking algorithm: *Proteins*, v. 52, p. 80-7 (2003); Gray, J. J., et al., Protein-protein docking with simultaneous optimization of rigid-body displacement and side-chain conformations: *J Mol Biol, v.* 331, p. 281-99 (2003); Huang, S. Y., Search strategies and evaluation in protein-protein docking: principles, advances and challenges: *Drug Discov Today*, v. 19, p. 1081-1096 (2014); Moal, I. H., et al., Scoring functions for protein-protein interactions: *Curr Opin Struct Biol*, v. 23, p. 862-7 (2013); Norel, R., et al., Electrostatic contributions to protein-protein interactions: fast energetic filters for docking and their physical basis: *Protein Sci*, v. 10, p. 2147-61 (2001); Ohue, M., et al., MEGADOCK: an all-to-all protein-protein interaction prediction system using tertiary structure data: *Protein Pept Lett*, v. 21, p. 766-78 (2014); Schneidman-Duhovny, et al., PatchDock and SymmDock: servers for rigid and symmetric docking: *Nucleic Acids Res*, v. 33, p. W363-7 (2005)) (each of which is hereby incorporated by reference in its entirety). In addition to these physical and statistical based scoring functions, biological data can be incorporated either at the search stage or the scoring stage, for example defining residues that contribute to the binding interface or restricting the docked interface to the cdrs of an Ab in Ab-Ag docking (Dominguez, C., et al., HADDOCK: a protein-protein docking approach based on biochemical or biophysical information: *J Am Chem Soc*, v. 125, p. 1731-7 (2003); Gray, J. J., et al., Protein-protein docking with simultaneous optimization of rigid-body displacement and side-chain conformations: *J Mol Biol*, v. 331, p. 281-99 (2003)) (each of which is hereby incorporated by reference in its entirety).

Several challenges to the problem of protein-protein docking exist. Docking methods generally perform well when re-docking the individual binding partners from the structure a bound complex, yet performance degrades when the structures of two proteins in their unbound state are used (Janin, J., 2010, Protein-protein docking tested in blind predictions: the CAPRI experiment: *Mol Biosyst*, v. 6, p. 2351-62) (hereby incorporated by reference in its entirety). Moreover, often rigid docking is performed, which does not take into account the potentially large conformation changes in secondary structure that may occur in some cases of protein-protein binding. Advances in docking include attempting to incorporate flexibility into the structures being docked, whether on the level of backbone or side chain (Zacharias, M., 2010, Accounting for conformational changes during protein-protein docking: *Curr Opin Struct Biol*, v. 20, p. 180-6) (hereby incorporated by reference in its entirety).

An reasonably accurate model of the interface of a protein-protein complex is a important for protein design experiments that aim to introduce novel function to protein scaffold (Fleishman, S. J., et al., Computational design of proteins targeting the conserved stem region of influenza hemagglutinin: *Science, v.* 332, p. 816-21(2011)) (hereby incorporated by reference in its entirety). In some cases, there has even been success using models of the proteins of interest for docking and subsequent protein design (Tharakaraman, K., et al. Redesign of a cross-reactive antibody to dengue virus with broad-spectrum activity and increased in vivo potency: *Proc Natl Acad Sci USA*, v. 110, p. E1555-64 (2013)) (hereby incorporated by reference in its entirety).

In order to predict the structure of a macromolecular complex, using docking or other methods, a three-dimensional structure of the individual proteins is required. In the absence of experimentally determined structures (i.e. X-ray or NMR), a model of the protein must be generated. In general, models can be built using three methods—homology modeling, ab initio modeling and fold-recognition/threading methods (Petrey, D., and B. Honig, 2005, Protein structure prediction: inroads to biology: *Mol Cell*, v. 20, p. 811-9) (hereby incorporated by reference in its entirety). Reliable models can be generated by homology modeling if the protein of interest has a homolog with an experimentally determined structure, where the homology is at least ~30% sequence identity (over a significant alignment length)(Rost, B., 1999, Twilight zone of protein sequence alignments: *Protein Eng, v.* 12, p. 85-94) (hereby incorporated by reference in its entirety). The homolog structure is used as 'template' on which to build the model (Sali, A., and T. L. Blundell, Comparative protein modelling by satisfaction of spatial restraints: *J Mol Biol*, v. 234, p. 779-815 (1993); Sali, A., et al., Evaluation of comparative protein modeling by MODELLER: *Proteins*, v. 23, p. 318-26 (1995); Webb, B., and A. Sali, Comparative Protein Structure Modeling Using MODELLER: *Curr Protoc Bioinformatics*, v. 47, p. 5.6.1-5.6.32 (2014)) (each of which is hereby incorporated by reference in its entirety). This 30% identity 'rule of thumb' may be sufficient for reliably modeling the correct protein fold; however, insertions or deletions, or sequence variability within loop regions, complicate the modeling and additional modeling approaches may be required. For proteins that do not have known 3D structures of homologs, or for regions of a protein with a high degree of variability relative to the template, methods such as ab initio modeling, or fold-recognition can be implemented (Petrey, D., and B. Honig, Protein structure prediction: inroads to biology: *Mol Cell*, v. 20, p. 811-9 (2005)) (hereby incorporated by reference in its entirety).

Structural relationships between evolutionarily distant sequences, as identified by structure alignments and/or other computational tools, can be used as a method to predict function for proteins that lack functional annotation but have known structures (Goldsmith-Fischman, S., and B. Honig, Structural genomics: computational methods for structure analysis: *Protein Sci*, v. 12, p. 1813-21 (2003); Goldsmith-Fischman, S., et al., The SufE sulfur-acceptor protein contains a conserved core structure that mediates interdomain interactions in a variety of redox protein complexes: *J Mol Biol*, v. 344, p. 549-65 (2004) (each of which is hereby incorporated by reference in its entirety). As an extension of this idea, the structure of the interface in a protein-protein complex (experimental or modeled by docking) may be used to identify and/or predict additional potential binders, by aligning regions of the protein comprising one side of the interface with a database of protein 3D structures, either by structural alignment of atoms or alignment of protein surfaces (Dey, F., et al., Toward a "structural BLAST": using structural relationships to infer function: *Protein Sci*, v. 22, p. 359-66 (2013); Gao, M., and J. Skolnick, iAlign: a method for the structural comparison of protein-protein interfaces: *Bioinformatics*, v. 26, p. 2259-65 (2010); Pandit, S. B., and J. Skolnick, Fr-TM-align: a new protein structural alignment method based on fragment alignments and the TM-score: *BMC Bioinformatics*, v. 9, p. 531 (2008); Shulman-Peleg, A. et al., SiteEngines: recognition and comparison of binding sites and protein-protein interfaces: *Nucleic Acids Res*, v. 33, p. W337-41 (2005); Zhang, Q. C., et al., Structure-based prediction of protein-protein interactions on a genome-wide scale: *Nature*, v. 490, p. 556-60 (2012)) (each of which is hereby incorporated by reference in its entirety).

Molecular Dynamics (MD) is a method that computationally simulates the movement of atoms and subsequent behavior of macromolecules in a biological system. (Karplus, M., and J. A. McCammon, Molecular dynamics simulations of biomolecules: *Nat Struct Biol*, v. 9, p. 646-52 (2002)) (hereby incorporated by reference in its entirety). The physical properties of the interaction potentials between atoms are described by a force-field, a set of functions approximating different properties of the atoms. The solvent properties of the biological system can be modelled explicity (i.e. using 3D models of water molecules) or implicitly, using various solvent models (Feig, M. et al., *Journal of Computational Chemistry* 25 (2): 265-84. (2004) (hereby incorporated by reference in its entirety)). MD can be utilized to assess and evaluate models of proteins, protein-ligand complexes, protein-protein interfaces.

In addition to physics-based approaches, machine learning methods can be implemented to analyze and predict components of protein-protein interfaces. Machine learning methods like Support Vector Machines (SVMs) and Random Forests are general algorithms developed to 'learn' from example data represented as vectors (Breiman, L., Random forests: Machine Learning, v. 45, p. 5-32 (2001); Cortes, C., and V. Vapnik, Support-vector networks, Machine Learning, September 1995, Volume 20, Issue 3, pp 273-297,) (each of which is hereby incorporated by reference in its entirety). Machine learning approaches as well as statistics-based methods have been used to predict Ag-Ab interfaces (Sela-Culang, I., et al., Using a combined computational-experimental approach to predict antibody-specific B cell epitopes: Structure, v. 22, p. 646-57 (2014)) (hereby incorporated by reference in its entirety) and suggest positions that may participate in Ag binding (Burkovitz, A., I. et al., Large-scale analysis of somatic hypermutations in antibodies reveals which structural regions, positions and amino acids are modified to improve affinity: FEBS J, v. 281, p. 306-19 (2014)) (hereby incorporated by reference in its entirety).

The molecular mechanisms that underlie somatic hypermutations have been the focus of extensive research. The introduced mutations are predominantly point mutations and rarely base insertions or deletions (Zhao, S. et al. *Mol Immunol* 47:694-700 (2010); Li, Z. et al., *Genes Dev* 18, 1-11 (2004) (each of which is hereby incorporated by reference in its entirety)) and are mediated by the activation-induced deaminase (AID) enzyme (Maul, R. W. et al., *Adv Immunol* 105, 159-191 (2010); Muramatsu, M. et al., *J Biol Chem* 274, 18470-18476 (1999) (each of which is hereby incorporated by reference in its entirety). AID introduces diversity by converting cytosine to uracil, which activates error-prone DNA repair mechanisms (Maul, R. W. et al., *Adv Immunol* 105, 159-191 (2010); Pham, P. et al., *Nature* 424, 103-107 (2003); Peled, J. U. et al., *Annu Rev Immunol* 26: 481-511 (2008) (each of which is hereby incorporated by reference in its entirety). Cytosines located within DNA motifs that are preferred binding targets of the AID enzyme are commonly referred to as hotspots (Dorner, T. et al., *Eur J Immunol* 28, 3384-3396 (1998) (hereby incorporated by reference in its entirety). However, not all of the hotspots are targeted (Kinoshita, K. et al., *Nat Rev Mol Cell Biol* 2, 493-503 (2001) (hereby incorporated by reference in its entirety)), and many SHMs occur near hotspots but not within them (Clark, L. A. et al., *J Immunol* 177, 333-340 (2006) (hereby incorporated by reference in its entirety)). The assumption that AID plays an important role in the SHM process inspired attempts to utilize it in vitro, e.g. by coupling mammalian cell-surface display with AID-directed SHM (Bowers, P. M. et al., *Proc Natl Acad Sci USA* 108, 20455-20460 (2011) (hereby incorporated by reference in its entirety)), or by designing phage display libraries based on DNA hotspots (Chowdhury, P. S. et al., *Nat Biotechnol* 17, 568-572 (1999) (hereby incorporated by reference in its entirety)).

Studies that have attempted to characterize SHMs structurally mostly involved analyses of the crystal structures of one or a few pairs of germline and mature variants of a specific Ab in order to determine how structural factors affect affinity enhancement. In one such study, examination of the X-ray crystal structures of four anti-lysozyme Ab variants at various maturation stages revealed that binding is enhanced by burial of increasing amounts of an apolar surface area and by improving shape complementarity. (Li, Y. et al., *Nat Struct Biol* 10, 482-488 (2003) (hereby incorporated by reference in its entirety). However, analysis of another set of Abs found that the mature Ab does not have better shape complementarity to the Ag than its germline variant, but exhibits a small improvement in shape complementarity between the variable light (VL) chain and the variable heavy (VH) chain, and has a higher electrostatic contribution to Ag binding than that of the germline Ab. (Midelfort, K. S. et al., *J Mol Biol* 343, 685-701 (2004) (hereby incorporated by reference in its entirety). The X-ray structure of an anti-hapten Ab and its corresponding germline Ab suggested that, in this case, the increased affinity is achieved mainly by electrostatic optimization. (Chong, L. T. et al., *Proc Natl Acad Sci USA* 96, 14330-14335 (1999) (hereby incorporated by reference in its entirety). Several studies used molecular dynamics simulations of a handful of mature Abs (Wong, S. E. et al., *Proteins* 79, 821-829 (2011) (herein incorporated by reference in its entirety), or a specific Ab lineage (Schmidt, A. G. et al., *Proc Natl Acad Sci USA* 110, 264-269 (2013); Thorpe, I. F. et al., *Proc Natl Acad Sci USA* 104, 8821-8826 (2007) (each of which is herein incorporated by reference in its entirety), and reported that rigidification of the paratope leads to a reduction in the entropic cost of the interaction.

The studies that have examined whether SHMs are focused on residues involved in Ag binding reached contradictory conclusions. Clark et al. identified SHMs in over 11 000 Ab sequences. (Clark, L. A. et al., *J Immunol* 177, 333-340 (2006) (herein incorporated by reference in its entirety). They reported that Ag-contacting positions are mutated three times more often than core residues. However, in this analysis, interface positions in the Ab sequence were defined as Ab positions that are within 12 Å of an Ag atom in any PDB structure, a definition that covers mostly residues that do not physically interact with the Ag. SHMs and hotspots were reported to be over-represented in the complementarity-determining regions (CDRs) (Clark, L. A. et al., *J Immunol* 177, 333-340 (2006); Dorner, T. et al., *J Immunol* 158, 2779-2789 (1997)). However, while CDRs cover ~80% of the Ag-binding residues, 50-60% of the residues in the CDRs do not contact the Ag. (Kunik, V. et al., *PLoS Comput Biol* 8, e1002388 (2012) (herein incorporated by reference in its entirety). Several studies indicated that SHMs mostly occur in the periphery of the germline Ag-binding site and not in its center (Tomlinson, I. M. et al., *J Mol Riot* 256, 813-817 (1996); Thom, G. et al., *Proc Natl Acad Sci USA* 103, 7619-7624 (2006) (hereby incorporated by reference in its entirety), and that SHMs do not show a clear preference toward residues that are in contact with the Ag (Ramirez-Benitez, M. C. et al., *Proteins* 45, 199-206 (2001); Raghunathan, T. et al., *J Mol Recog* 25, 103-113 (2012) (hereby incorporated by reference in their entirety)). It has even been suggested that mutations in the interface may be disfavored as they disrupt Ab-Ag interaction. (Ramirez-Benitez, M. C. et al., *Proteins* 45, 199-206 (2001); Persson, J. et al., *Tumour Biol* 30, 221-231 (2009) (hereby incorporated by reference in their entirety).

In one embodiment, the steps of the process of the present invention correspond to the iterative process described in FIG. 1.

Modeling:

In one embodiment of the invention, a model of the antigen of interest in the receptor-bound conformation, is generated (e.g. using tools for homology structural modeling such as MODELLER (Fiser, A., et al. Modeling of loops in protein structures: *Protein Sci, v.* 9, p. 1753-73 (2000); Marti-Renom, M. A., et al., Comparative protein structure modeling of genes and genomes: *Annu Rev Biophys Biomol Struct*, v. 29, p. 291-325 (2000); Sali, A., and T. L. Blundell, Comparative protein modelling by satisfaction of spatial restraints: *J Mol Biol*, v. 234, p. 779-815 (1993)) (each of which is hereby incorporated by reference in its entirety) as implemented in the Discovery Studio suite, or any other structure prediction tool)(Accelrys et al., 2013 (hereby incorporated by reference in its entirety)). When the experimentally determined structure is available (e.g. in the PDB (Berman, H. M., et al., The Protein Data Bank: *Acta Crystallogr D Biol Crystallogr*, v. 58, p. 899-907 (2002)) (hereby incorporated by reference in its entirety)), it can be used as well). The model may be further refined by energy minimization (e.g. using CHarMM as implemented in the Discovery Studio suite (Brooks, B. R., et al. CHARMM: the biomolecular simulation program: *J Comput Chem*, v. 30, p. 1545-614 (2009)) (hereby incorporated by reference in its entirety), or any software for minimization), and in some cases molecular dynamics (MD) simulations (e.g. using GROMACS (Hess, B., et al. GROMACS 4: Algorithms for Highly Efficient, Load-Balanced, and Scalable Molecular Simulation: *Journal of Chemical Theory and Computation*, v. 4, p. 435-447 (2008)) (hereby incorporated by reference in its entirety) or other MD software tools)

When it is impossible to reliably model the entire protein, a structural model of the desired epitope alone may be used. This model can be generated using, for example, homology modeling (as described above) or de-novo prediction of the structural determinant.

Docking:

In one embodiment of the present invention, the model (or experimental structure) is then docked against a database of antibody three-dimensional structures, using, for example, ZDOCK (Chen, R., et al. ZDOCK: an initial-stage protein-docking algorithm: *Proteins*, v. 52, p. 80-7 (2003); Pierce, B., and Z. Weng, ZRANK: reranking protein docking predictions with an optimized energy function: *Proteins*, v. 67, p. 1078-86 (2007); Vreven, T., et al., Performance of ZDOCK in CAPRI rounds 20-26: *Proteins* (2013)) (each of which is herein incorporated by reference in its entirety) as implemented in Discovery Studio, (Accelrys, Software, and Inc., 2013, *Discovery Studio Modeling Environment, Release* 4.0, San Diego, Accelrys Software Inc. (hereby incorporated by reference in its entirety); Marcatili, P., et al. The association of heavy and light chain variable domains in antibodies: implications for antigen specificity: *Febs Journal*, v. 278, p. 2858-2866 (2011)) (hereby incorporated by reference in its entirety) and/or additional docking algorithms (e.g. Hex Ritchie, D. W., and V. Venkatraman, Ultra-fast FFT protein docking on graphics processors: *Bioinformatics*, v. 26, p. 2398-405 (2010)), (hereby incorporated by reference in its entirety) Megadock (Ohue, M., et al., MEGADOCK: an all-to-all protein-protein interaction prediction system using tertiary structure data: *Protein Pept Lett*, v. 21, p. 766-78 (2014)) (each of which is herein incorporated by reference in its entirety). Biological and structural data for the antigen and antibody may be used to focus the docking or to eliminate unlikely poses (e.g. poses in which the contacts with the antigen are made by residues in the constant region) so that the epitope of interest and the CDRs are in the docked interface. This screening of poses may rely on the following considerations:

1. Determining whether the contacting residues in the pose involve CDR positions that are likely to be in contact with the antigen. This can be based on biophysical assessment and on statistical assessment of the propensities of contacts in each position in all known antibodies, as described in (Kunik, V., and Y. Ofran, The indistinguishability of epitopes from protein surface is explained by the distinct binding preferences of each of the six antigen-binding loops: *Protein Eng Des Sel*. (2013); Kunik, V., et al., Structural consensus among antibodies defines the antigen binding site: *PLoS Comput Biol*, v. 8, p. e1002388 (2012b)) (each of which is hereby incorporated by reference in its entirety). Identification of the antigen binding residues can be based on the process described in (Kunik, V., et al. Paratome: an online tool for systematic identification of antigen-binding regions in antibodies based on sequence or structure, *Nucleic Acids Res*, v. 40: England, p. W521-4 (2012a)) (hereby incorporated by reference in its entirety), or on other methods for identifying CDRs (e.g. Chothia, C., and A. M. Lesk, Canonical structures for the hypervariable regions of immunoglobulins: *J Mol Biol*, v. 196, p. 901-17 (1987); Giudicelli, V., et al., IMGT/GENE-DB: a comprehensive database for human and mouse immunoglobulin and T cell receptor genes: *Nucleic Acids Res*, v. 33, p. D256-61 (2005); Kabat, E., A., et al., Sequence of proteins of immunological interest, National Institute of Health, Bathesda (1983); Lefranc, M. P., et al., IMGT/3Dstructure-DB and IMGT/DomainGapAlign: a database and a tool for immunoglobulins or antibodies, T cell receptors, MHC, IgSF and MhcSF: *Nucleic Acids Research*, v. 38, p. D301-D307 (2010); Lefranc, M. P., et al. IMGT/3Dstructure-DB and IMGT/StructuralQuery, a database and a tool for immunoglobulin, T cell receptor and MHC structural data: *Nucleic Acids Research*, v. 32, p. D208-D210 (2004); Lefranc, M. P., et al. IMGT unique numbering for immunoglobulin and T cell receptor variable domains and Ig superfamily V-like domains: *Dev Comp Immunol*, v. 27, p. 55-77 (2003); Morea, V., et al. Antibody modeling: implications for engineering and design: *Methods*, v. 20, p. 267-79 (2000)) (hereby incorporated by reference in their entirety) or antigen binding residues (Krawczyk, K., et al., Antibody i-Patch prediction of the antibody binding site improves rigid local antibody-antigen docking: *Protein Eng Des Sel*, v. 26, p. 621-9 (2013); Krawczyk, K., et al., Improving B-cell epitope prediction and its application to global antibody-antigen docking: *Bioinformatics*, v. 30, p. 2288-94 (2014); Olimpieri, P. P., et al. Prediction of site-specific interactions in antibody-antigen complexes: the proABC method and server: *Bioinformatics*, v. 29, p. 2285-91 (2013); TRAMONTANO, A., et al. FRAMEWORK RESIDUE-71 IS A MAJOR DETERMINANT OF THE POSITION AND CONFORMATION OF THE 2ND HYPERVARIABLE REGION IN THE VH DOMAINS OF IMMUNOGLOBULINS: *Journal of Molecular Biology*, v. 215, p. 175-182 (1990)) (each of which is hereby incorporated by reference in its entirety).

2. Removing poses in which the epitope does not overlap with the preselected epitope.

3. Selecting poses that, based on structure-function analysis, are likely to result in desired biological activity.

In one embodiment, the resulting docking poses are then filtered in order to identify poses that have "native-like" properties, such as shape and/or biophysical feature complementarity. Additional scores are learned from known antibody-antigen complexes. The following filters may be implemented:

A. Docking ranking: Top X ranking by various docking scoring functions.

B. Docking consensus: For each docked antibody-antigen complex, poses that pass filter A are compared between at least two different docking algorithms, and those that are generated by more than one algorithm (based on agreement in RMSD of the antibody CDRs) are selected for further analysis.

C. Knowledge-based features of known antibody-antigen complexes: Use machine learning to evaluate the complexes that have passed filter B. For example, we developed two different types of machine-learning classifiers, based on a similar approach to the one described in (Sela-Culang, I. et al., *Structure* 22:646-657 (2014) (herein incorporated by reference in its entirety).

First Type of Classifiers:

The present inventors assembled a training set of antibody-antigen complexes of known structure. In each complex the present inventors identified the ABR/CDR residues on the antibody that contact the antigen, and the residues on the antigen that contact the antibody. Each antigen residue was described in terms of its secondary structure (predicted or experimentally determined), evolutionary conservation, solvent accessibility, the identity, secondary structure and conservation of each of its neighbors (the inventors used a sequence window of 3 to 7 residues on each side but other window sizes may be used as well). The antibody residues were described in varied windows in terms of residue type, solvent accessibility, the position of residue within the CDR, the type of the CDR, and whether it is a germ-line residue or mutated (SHM). In addition, we built a knowledge-based potential for contacts between antibody residues and antigen residues. These potentials quantify the propensity (e.g. in terms of log likelihood) for a contact between a certain type of residue on the antibody and a certain type of residue on the antigen. That is, it assesses whether a certain type of residue-residue contact between antibody and antigen occurs more or less than expected by chance. This allowed the inventors to determine whether this particular contact is favored or disfavored in antibody-antigen interfaces. The inventors also built a more detailed set of such potentials for each CDR separately. This allows us to give a positive or negative score for each contact on each CDR. When possible (e.g. when the amount of experimental data permits), the inventors also built additional sets of potentials for specific structural positions on each CDR. This was done by aligning multiple CDRs that are similar to each other and then assessing the propensities of each of the 20×20 possible contacts between residue on the antibody position and residues on the antigen.

The input vector for the supervised machine-learning algorithm (Random Forest and SVMs was used, but other machine learning algorithms can be used as well), was a vector that describes a residue position on the antibody, a vector that described a residue position on the antigen and the contact potential for this pair. The positive training set was the observed contacts, and the negative set was random pairing of ABR antibody and antigen surface residues. A 3-fold cross-validation was used. The classifier distinguished well between real and decoy antigenic contacts.

Antibody-antigen complexes can be examined by the analysis of the predictions of classifiers' predictions on the interface residue pairs. For example, geometric or the arithmetic mean of the predictions scores on all or on a subset of the residue pairs in the interface of question.

A Second Type of Classifier:

The present inventors assembled a positive training set of antibody-antigen interfaces collected from experimentally determined 3D structures. A negative set was assembled from docking structures of antibodies to proteins, under the assumption that in the vast majority of cases a random antibody will not bind a random antigen and thus these interfaces represent false interfaces. The inventors filtered these negative interfaces, as described above, to retain only native-like complexes. Then, each interface was described using the following features: the number of contacts, what fraction of contacts are germ-line and what fraction are SHMs. How many specific contacts are there, how many H-bonds, how many aromatic interactions, etc. A score for the curvature of the surface, assessment of shape complementarity, Assessment of charge complementarity, area of the interface, relative area of interface on the antigen, reduction in solvent accessible area for the antibody and for the theoretical paratope (as calculated by canonic CDRs or by Paratome (Kunik, V., S. Ashkenazi, and Y. Ofran, Paratome: an online tool for systematic identification of antigen-binding regions in antibodies based on sequence or structure, *Nucleic Acids Res*, v. 40: England, p. W521-4 (2012a)) (herein incorporated by reference in its entirety). Other biophysical and structural description of the interface may be used as well (e.g. conservation). The inventors also recorded the potentials for all contacts, as described above. In addition docking was run for the positive set, and the docking score of all docked poses was recoded. The inventors added to the vector that represented each interface features that described the distribution of docking scores. This is motivated by the observation that the distribution of docking scores of the different poses of a given antibody-antigen pair, differ dramatically between pair that are known to bind each other and pairs that are not known to bind each other (and that are assumed not to). These features include the distance (in terms of standard deviations) of the extreme values from the mean and or the median, the standard deviation itself, the distant between the mean and the median, and quintile characteristics. The inventors then used a Random Forest and an SVM to distinguish between real interfaces and decoys. A 10-fold cross validation has shown that this classifier distinguishes well between real and false interfaces.

In addition to identifying "native-like" complexes based on results of protein-protein docking methods, the antibody-antigen complex may be modeled based on information obtained from structural analyses of protein-protein interfaces. Structures of either the antibodies or the antigen, or even only the epitope, may be screened against a database of 3D structures of protein complexes, in the form of local structure alignments, to identify protein-protein interfaces in which one partner shares structural features with the query protein. Superposition of the query (antibody or antigen/epitope) on the structurally similar protein-protein complex may suggest a model of the antibody-antigen complex, which can subsequently be analyzed using binding free energy calculations (e.g. using the energy calculation tools in Discovery Studio (Accelrys, Software, and Inc., 2013, *Discovery Studio Modeling Environment, Release* 4.0, San Diego, Accelrys Software Inc.) (hereby incorporated by reference in its entirety), or similar tools such as FoldX (Schymkowitz, J., et al. The FoldX web server: an online force field: *Nucleic Acids Research*, v. 33, p. W382-8 (2005) (hereby incorporated by reference in its entirety), Rosetta (Kuhlman, B., et al. Design of a novel globular protein fold with atomic-level accuracy: *Science*, v. 302, p. 1364-8 (2003); Kunik, V., et al., Paratome: an online tool for systematic identification of antigen-binding regions in antibodies based on sequence or structure, *Nucleic Acids Res*, v. 40: England, p. W521-4 (2012a); Liu, Y., and B. Kuhlman, RosettaDesign server for protein design: *Nucleic Acids Res*, v. 34, p. W235-8 (2006) (hereby incorporated by reference in their entirety) or other computational tools). It is also possible to use machine-learning analysis described above. This methodology can be also implemented as a filter to analyze the models resulting from protein-protein docking. In addition, antibody-antigen interfaces arising from protein-protein docking can be structurally compared, using these methods, with known protein-protein interfaces to identify interactions that may introduce specificity.

Docking models that pass the filters and represent potential complexes with the template antibody may be subjected to energetic refinement (for example, minimization and side chain refinement implemented in Discovery Studio or similar methods) prior to further analyses, and MD simulations may be used to assess their stability.

The process of pose selection described above enables the selection of a docked model with the antibody structure to be used as a template for library design.

Figure 3A:
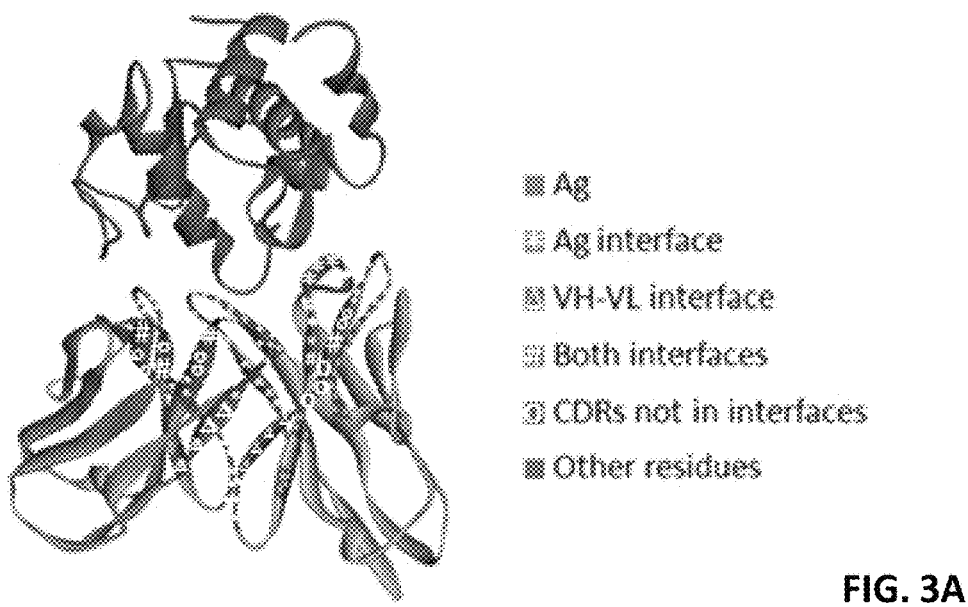
Figure 3B:
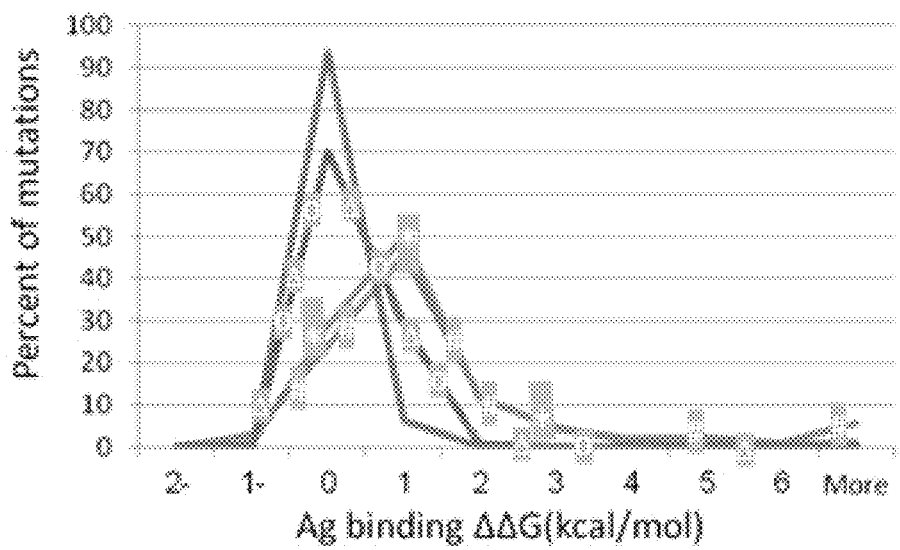
Figure 3C:
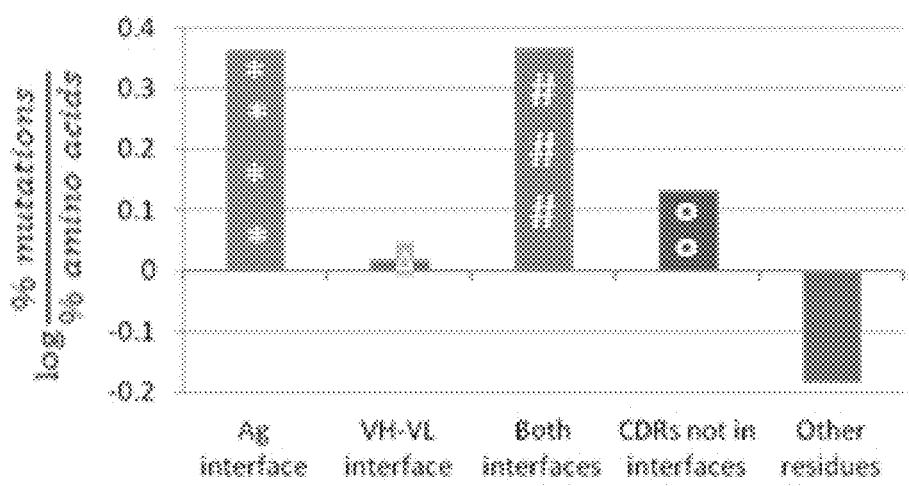
Figure 4:
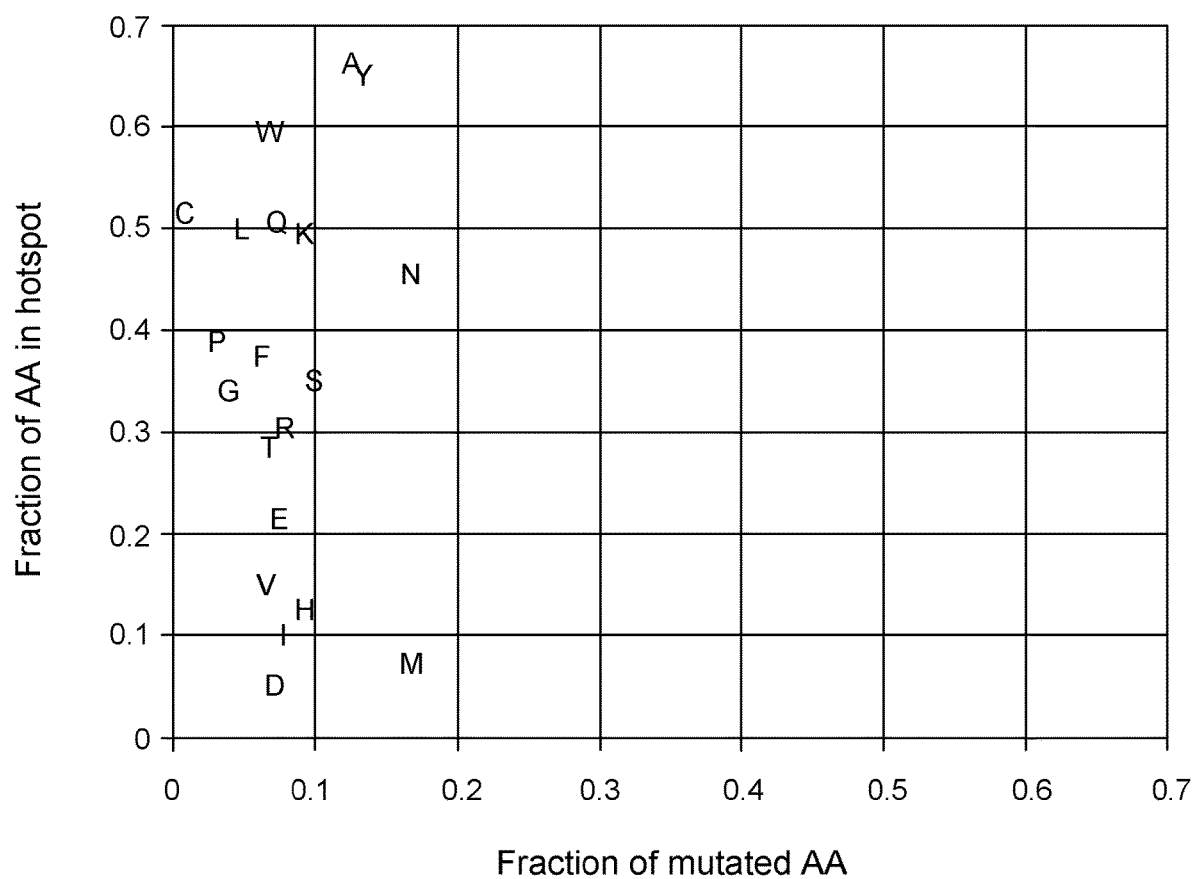

Libraries:

In one embodiment of the present invention, positions within the CDRs of the template antibody or antibodies are selected for the introduction of variability for library design. For each antibody template, the CDRs are identified using, for example, Paratome (Kunik, V., et al. Paratome: an online tool for systematic identification of antigen-binding regions in antibodies based on sequence or structure, *Nucleic Acids Res*, v. 40: England, p. W521-4 (2012a)) (hereby incorporated by reference in its entirety) or other tools for CDR identification. Based on the docked model of the antibody-antigen complex, residues within the CDRs that are in the interface with the antigen in the model are selected as potential candidates for mutational variability. Sequence analysis (using Blast or similar program) and, in some cases, structure based sequence alignments (North, B. et al., *J. Mol. Biol.* 406:228-256 (2011) (herein incorporated by reference in its entirety) are used to analyze these positions to determine whether they are likely to tolerate variability (based on how often variability is observed in related sequences). In addition, bioinformatic analyses of SHM data such as the data available in the analysis in (Burkovitz, A., I. Sela-Culang, and Y. Ofran, 2014, Large-scale analysis of somatic hypermutations in antibodies reveals which structural regions, positions and amino acids are modified to improve affinity: FEBS J, v. 281, p. 306-19) (hereby incorporated by reference in its entirety), may be used to evaluate the variability of these positions as well as their potential structural and functional relevance. Thus, the SHM data can be used to select both the positions and the variations. As seen in FIG. 3 and FIG. 4, each position has different tolerability for SHMs, and each position prefers different substitutions. Such data, including more detailed assessment for substitution in each CDR and, when possible, for specific positions, are crucial when designing the original library.

Variation at each selected CDR position can be determined using physical-chemical considerations, knowledge-based approaches, and based on the SHMs data described above. In one embodiment, the residue positions are mutated in silico to other amino acids, either in the context of the docked model or the structure of the free antibody, in order to calculate the effect of the mutation on both the binding free energy and the folding energy (stability), respectively, using, for example, the Mutation Energy protocols implemented in Discovery Studio (Accelrys, Software, and Inc., 2013, *Discovery Studio Modeling Environment, Release* 4.0, San Diego, Accelrys Software Inc.) (hereby incorporated by reference in its entirety), or similar such algorithms (e.g. FoldX (Schymkowitz, J., J. Borg, F. Stricher, R. Nys, F. Rousseau, and L. Serrano, 2005, The FoldX web server: an online force field: Nucleic Acids Research, v. 33, p. W382-8) (hereby incorporated by reference in its entirety) Rosetta or algorithms available in the Schrödinger suit (Kuhlman, B., G. Dantas, G. C. Ireton, G. Varani, B. L. Stoddard, and D. Baker, 2003, Design of a novel globular protein fold with atomic-level accuracy: *Science*, v. 302, p. 1364-8; Liu, Y., and B. Kuhlman, 2006, RosettaDesign server for protein design: *Nucleic Acids Res*, v. 34, p. W235-8; Schrödinger, Release, and 2014-3, 2014, MacroModel, version 10.5, Schrödinger, LLC, New York, N.Y.; Schymkowitz, J., J. Borg, F. Stricher, R. Nys, F. Rousseau, and L. Serrano, 2005, The FoldX web server: an online force field: *Nucleic Acids Research*, v. 33, p. W382-8) (each of which is herein incorporated by reference in its entirety)). Sequence analysis and structure based sequence alignments are used to analyze the CDR positions when considering resulting in silico mutations to determine their likelihood. 3D models of the mutated antibodies in complex with the antigen may be analyzed by machine learning to identify favorable mutations and may be subjected to molecular dynamics simulations to assess the stability of the mutant antibody-antigen docked pose. Interfaces of known binders of the antigen can also be used as a guide for the variability. Applying Genetic algorithm or another search/optimization algorithm on the classifiers can be used to suggest positions and mutations in the library.

EXAMPLES

Example 1

Identification of Substitutable Paratope Residues and Potential Substitutions

This experiment sought to determine the principles that guide in vivo Ab affinity maturation. In particular, we attempted to identify factors that determine which residues are removed and which new ones are introduced during the SHM process. Given the controversies regarding the tendency of the paratope to undergo SHM, we sought to determine whether different structural parts of the Abs have different tendencies for substitutions. To this end, we analyzed 3495 SHMs in 196 structurally characterized Ab-Ag complexes, and examined (a) the role of AID hotspots in directing mutations, (b) the selective pressure for substitutions in different structural regions of the Ab, and (c) the predicted energetic effect of each substitution. It was found that AID motifs have no effect on selection of mutated residues, but the energetic contribution to Ag binding appears to have a major effect. Finally, a map was generated of the preferred substitutions in each region of the Ab. These results contribute to understanding of the principles that govern the SHM process, and may guide the design and engineering of high-affinity Abs.

Using the data regarding preferred substitutions, we identified residues in the template sequence to be modified. Template variants were created by substituting these residues with variant residues indicated by the SHM analysis. In this manner, a library of template variants was formed for subsequent screening.

Example 2

Materials and Methods

A. Ab-Ag Complex Dataset Construction 3D structure files of 752 Ab-Ag complexes were downloaded from IMGT/3Dstructure-DB (version 4.5.0). (Ehrenmann, F. et al., *Nucleic Acids Res* 38, D301-D307 (2010); Kaas, Q. et al., *Nucleic Acids Res* 32, D208-D210 (2004) (each of which is herein incorporated by reference in its entirety). Complexes with Abs from human (154 structures) or mouse and chimeric Abs (492 structures) were retained. Abs from mouse and chimeric Abs were grouped as mouse Abs. To identify the light and heavy chains in each complex, we clustered human sequences into two clusters and murine sequences into two clusters, each corresponding to either heavy or light, using BlastClust. (Dondoshansky, I. et al., *BLASTclust* (*NCBI Software Development Toolkit*). *National Center for Biotechnology Information, Bethesda, Md.* (2002) (herein incorporated by reference in its entirety). Complexes that included only one chain and light chain dimers were removed. For redundancy removal, VH and VL sequences of each Ab were concatenated, and BlastClust was used with sequence identity of 97% and coverage of 95%. The Ab-Ag complex that was not engineered or mutated was the selected representative sequence in each cluster. In cases where there was more than one non-engineered complex, the longest Ag with the best resolution was used. We identified Ags that are proteins or peptides. All other Ags were removed. One complex (PDB ID 1IGC) in which the sole non-Ab chain was protein G was also excluded from the analysis. In case where the closest gene in IMGT did not agree with the annotated species, we reviewed the relevant literature, which led to exclusion of 12 complexes from the analysis: six of these cases were humanized Abs, five of them came from non-naive synthetic libraries and one came from rabbit. Overall, the dataset contained 196 non-redundant Ab-Ag complexes.

B. Identification of Germline Precursors and SHMs

Sequence alignment was used to identify the related germline gene precursors and identify SHMs. Only variable regions were analyzed. Human and mouse sequences were submitted separately. Default parameters were used. The CDRH3 and CDRL3 alignments were manually reviewed and corrected accordingly. Similar results were obtained when the analysis was repeated after removing junction positions (positions 106-116 for the VH domain and positions 115 and 116 for the VL domain).

C. Definition of SHM Contacting Residues, Germline Contacting Residues and Protein-Protein Interfaces For each complex structure in the protein-protein dataset (fully described previously in Kunik, V. et al., *Protein Eng Des Sel* 26:599-609 (2013)) (herein incorporated by reference in its entirety), the interface of a given chain included all residues in that chain for which at least one of their heavy atoms is within a distance of 6 Å from any of the other chains (Ofran, Y., "Prediction of protein interaction sites" In COMPUTATIONAL PROTEIN-PROTEIN INTERACTIONS (Nussinov R & Schreiber G, eds), pp. 167-184. CRC Press, Boca Raton, Fla. (2009)) (herein incorporated by reference in its entirety). The interface residues in all the chains in the protein-protein dataset were grouped as "protein-protein interfaces". For each complex structure in the Ab-Ag dataset, the contacting residues included all residues for which at least one of their heavy atoms is within a distance of 6 Å from the Ag (Ofran, Y., "Prediction of protein interaction sites" In COMPUTATIONAL PROTEIN-PROTEIN INTERACTIONS (*Nussinov R & Schreiber G,* eds), pp. 167-184. CRC Press, Boca Raton, Fla. (2009)) (herein incorporated by reference in its entirety). It was shown in a previous study that using a distance cut-off of 5 Å does not change the overall composition of contacting residues in Ab-Ag interfaces (Kunik, V. et al., *Protein Eng Des Sel* 26: 599-609 (2013)) (herein incorporated by reference in its entirety). Contacting residues that were retained throughout Ab affinity maturation were defined as "germline contacting residues". Contacting residues that were modified during Ab affinity maturations were defined as "SHM contacting residues".

D. Energy Calculation

We performed a computational alanine scan for all contacting residues in the Ab, and assessed the effect of this mutation on Ag binding. To assess SHMs, we mutated each introduced residue back to its germline residue. ΔΔG values were calculated using FoldX. (Schymkowitz, J. et al., *Nucleic Acids Res* 33, W382-W388 (2005); Guerois, R. et al., *J Mol Biol* 320: 369-387 (2002)) (each of which is herein incorporated by reference in its entirety). The following steps were performed in both cases, as they differ from each other only in the mutation target (alanine or the corresponding germline residue). First, PDB structures were optimized using the FoldX RepairPDB function. Then each mutation was performed separately using the BuildModel function. This resulted in generation of mutants and their corresponding wild-type structure models. The heavy chain and the light chain of the Ab were grouped together to calculate the energy values of the assembled Ab, and the AnalyzeComplex function was used to calculate the binding ΔG of each model. The ΔΔG value for each mutant was then calculated by subtracting the wild-type ΔG value from the mutant ΔG value.

E. Ab Structural Division Into Non-Overlapping Structural Regions

Contact between two residues was defined as at least two heavy atoms (one from each residue) within a distance of 6 Å. The region "Ag interface" comprises all residues that contact the Ag but do not contact residues from the other Ab chain. The region "VH-VL interface" comprises all residues that contact the other Ab chains but not the Ag. The region "both interfaces" comprises Ab residues that contact both the Ag and the other Ab chain. The ABRs were identified using Paratome. (Kunik, V. et al., *Nucleic Acids Res* 40, W521-W524 (2012)) (herein incorporated by reference in its entirety). Residues in the ABR regions that do not contact the Ag or the other Ab chain were grouped as "ABRs not in interfaces".

F. Amino Acids Within DNA Hotspot Motifs

The DNA hotspot motifs were RGYW or WRCY (Darner, T. et al., *Eur J Immunol* 28, 3384-3396 (1998)) (herein incorporated by reference in its entirety) where R indicates a purine base, Y indicates a pyrimidine base, and W indicates for an A or T base. For each amino acid, the proportion within hotspot motifs is the number of occasions the amino acid appeared within the hotspot motif out of the total appearances of the same amino acid in the germline sequences (V and J segments only) for all Abs in the dataset.

G. Distance from the Nearest Hotspot Motif

For each amino acid or mutation up to position 105 (according to IMGT numbering) in the V region, the distance from the nearest hotspot motif (RGYW or WRCY) was calculated as described previously. (Clark, L. A. et al., *J. Immunol.* 177: 333-340 (2006)) (herein incorporated by reference in its entirety). Briefly, the distance was defined as the number of bases between the middle codon and the nearest base of a hotspot motif A distance of zero indicates that the middle codon is inside a hotspot motif. Since the motifs have four positions the center nucleotide of a codon is four times more likely to fall somewhere within the motif than to fall in any other specific distance from it. Therefore, the observed number of cases with a distance of zero was divided by four before calculation of distributions. Amino acids or mutations that had two hotspots within the exact same distance were counted twice for that distance (with opposite signs).

H. Amino Acid Propensity for Mutation

The 196 Ab-Ag complexes were divided into three random subsets. The propensity of each amino acid to be mutated in each subset was calculated as:

$$\text{Propensity to be mutated} = \log \frac{AA1gl \text{ region} \to X \text{ mature region} + 1}{\frac{AA1gl \text{ region}}{\text{Total } aagl \text{ region}} \times \text{mutations in the region} + 1}$$

where AA1 gl region→X mature region is the number of changes from amino acid AA1 in the germ-line to any amino acid in the structural region, $$\frac{AA1gl \text{ region}}{\text{Total } aagl \text{ region}}$$

is the frequency of amino acid AA1 in the germ-line sequences of structural region, and. mutations in the region is the number of mutations in the structural region. Priors of 1 were added. Propensity values from each of the random subsets were averaged and then used for standard error calculation.

I. Mutation Probability and Ab Position Numbering

Abs positions and CDR definitions are numbered according to IMGT numbering. (Lefranc, M. P. et al., *Dev Comp Immunol* 27: 55-77 (2003)) (herein incorporated by reference in its entirety). The mutation probability was calculated as the number of mutations in a specific position divided by the number of appearances of an amino acid in this specific position. If the number of appearances of an amino acid in a specific position was ≤5, it was excluded from FIG. 7.

J. Standard Error Calculation

Figure 2:
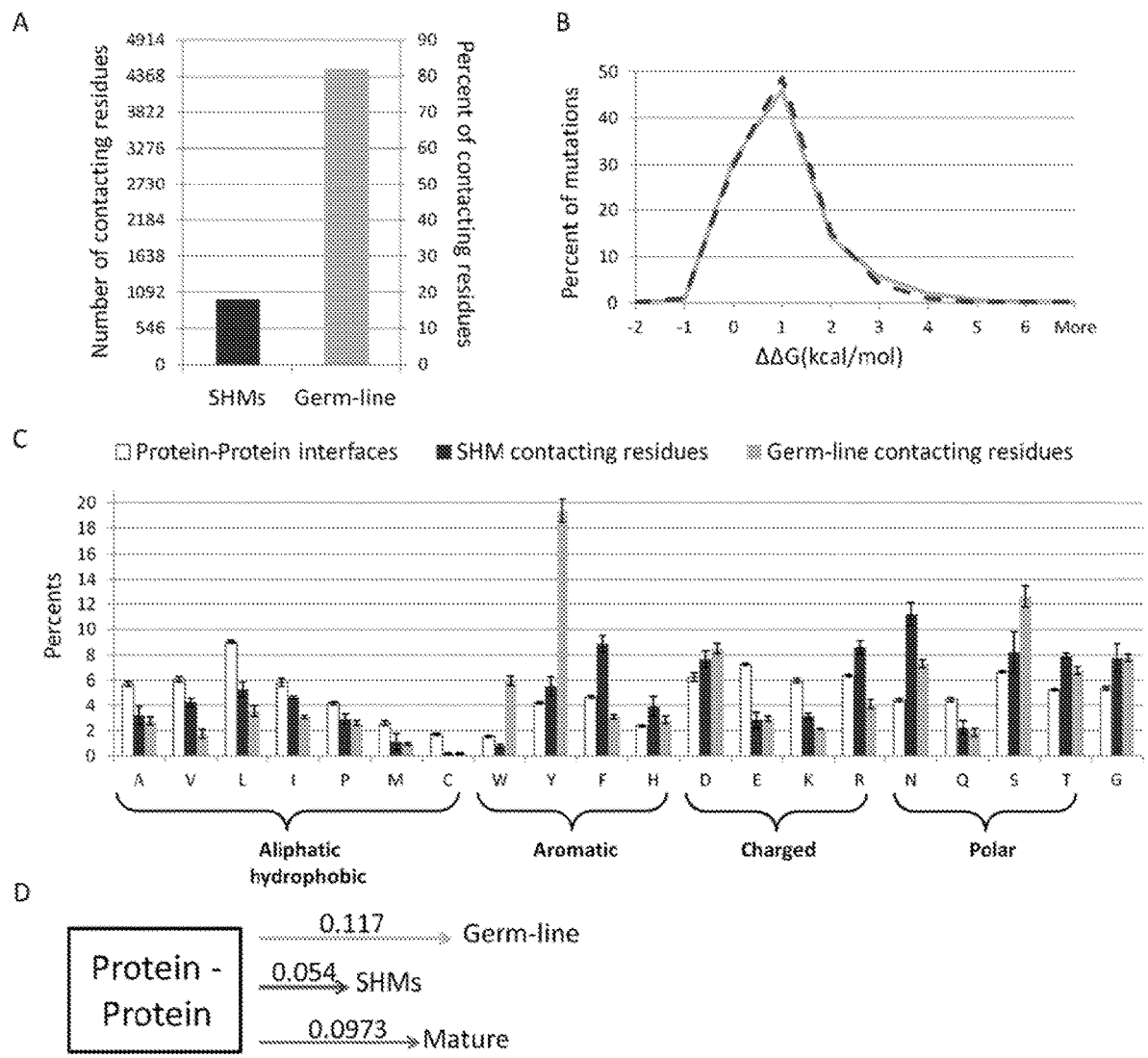
Figure 5:
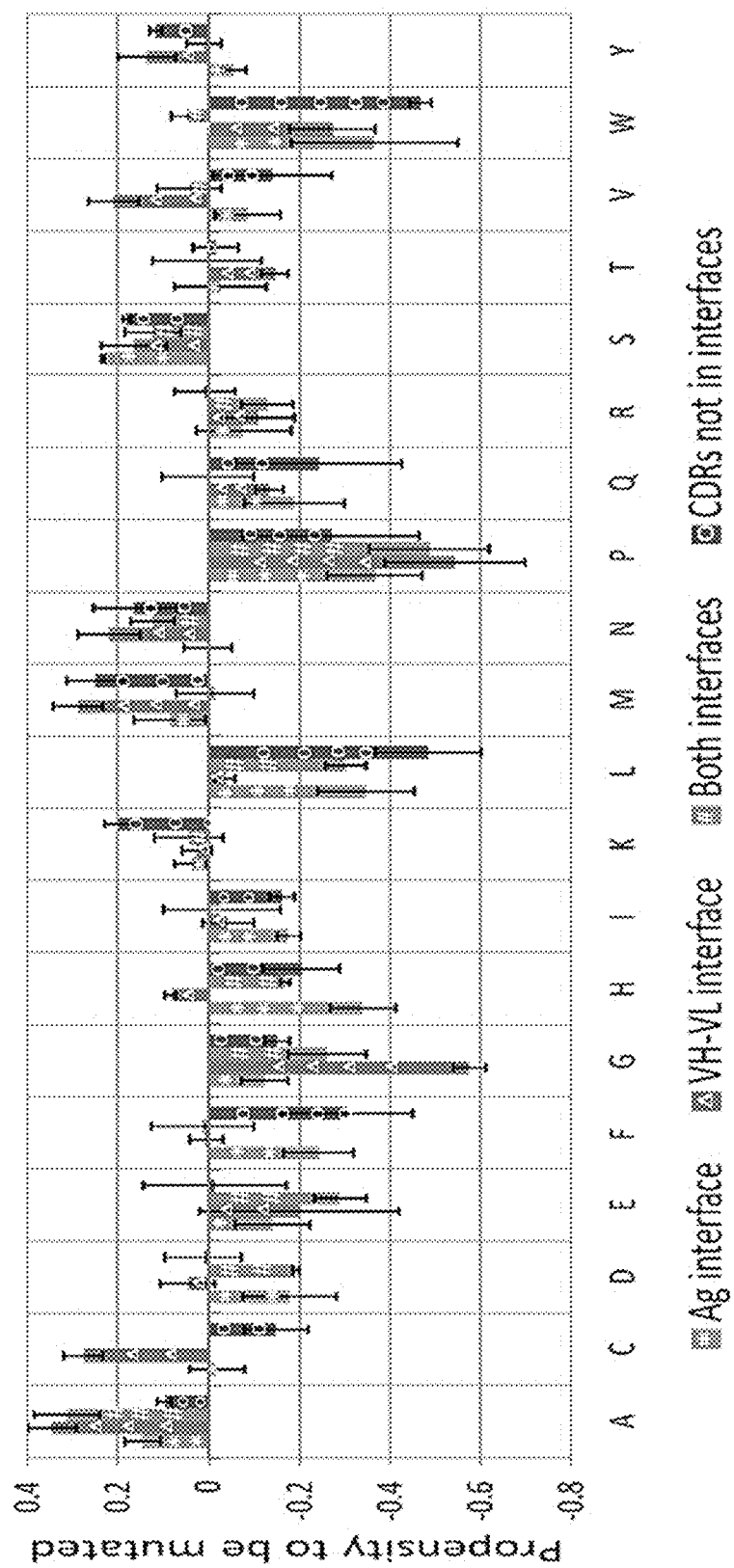
Figure 6:
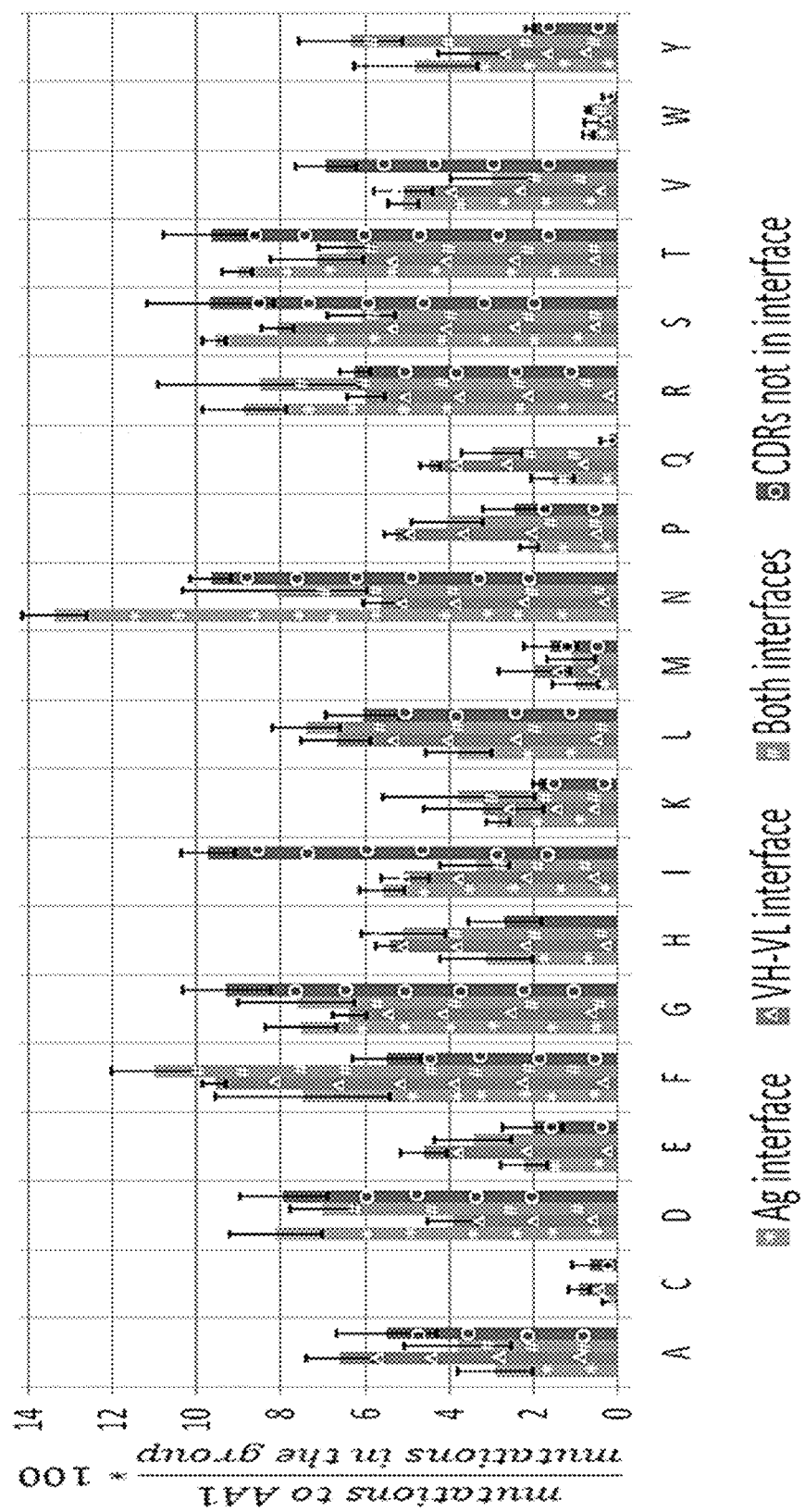

Standard errors for FIGS. 2, 5 and 6 were calculated by dividing the 196 Ab-Ag complexes or 210 general protein-protein interfaces into three random subsets. Values from each of the random subsets were averaged and then used for standard error calculation. For FIG. 7, ΔΔG values for each position were averaged and used for standard error calculation.

Example 3

A. Dataset Construction and SHMs Identification

A non-redundant dataset of 196 Ab-Ag complexes was generated (Table S1). Overall, 3495 SHMs were identified in the variable regions. Of those, 2172 occurred in mouse sequences (with a mean of 14.87 mutations per Ab) and 1323 occurred in human sequences (with a mean of 26.46 mutations per Ab). This difference may be ascribed, at least in part, to the way Abs are collected from mice and humans. The former are typically killed, and Abs collected, shortly after exposure to the Ag when they are a few months old. Human Abs, on the other hand, are typically collected from the blood of infected adults after repeated exposures to Ags.

B. AID Hotspot Motifs are Not Correlated to SHMs

As only the amino acid sequences of the mature Abs are available in the Protein Data Bank, it is impossible in most cases to retrieve the DNA sequences of the mature Ab from public databases. However, it is possible to retrieve the DNA sequences of the germline genes. These sequences allow us to evaluate the relationships between SHMs and AID hotspot motifs (RGYW or WRCY; R indicates a purine base, Y indicates a pyrimidine base, W indicates an A or a T base) (Darner T, et al., *Eur. J. Immunol.* 28:3384-3396 (1998) (hereby incorporated by reference in its entirety) in the germline genes.

FIG. 2A shows how often a certain amino acid overlaps with an AID hotspot motif versus how often it is actually mutated during SHM. The calculated correlation coefficient is −0.0127, indicating that amino acids that hit hotspot motifs more often, are not more likely to undergo SHM. This is most extreme in the case of methionine and aspartic acid, which are the least frequent amino acids in AID hotspots and have more mutations than AID sites. We also mapped the location of mutations in the V gene to their positions in the germline genes. Then, we calculated the distance of each mutation and each residue in all Ab V genes from the nearest hotspot motif. This was previously performed by Clark et al. (Clark, L. A. et al., *J. Immunol.* 177:333-340 (2006) hereby incorporated by reference in its entirety) for a set of ~11 000 Ab sequences. FIG. 2B shows the distribution of mutations at different distances from hotspots. The results here are very similar to the previously published results (Clark, L. A. et al., *J. Immunol.* 177:333-340 (2006)). Based on these results, it has been previously suggested that mutations are more likely to occur in positions that are located closer to a hotspot motif. However, we added a control to this analysis by checking the distance of codons from the nearest hotspot motif for residues that were not necessarily substituted in SHMs. We found that the typical distance of a residue from a hotspot is very similar whether it has been mutated during SHM or not, suggesting that the distribution of hotspots along the sequence is such that any codon encoding an amino acid is more likely to be located near or within a hotspot than to be distant from one. However, FIG. 2B shows that position 0 has a slightly higher value for residues that underwent SHM (gray line) compared to other residues (black line), indicating that residues that have been mutated are slightly more likely to have codons that overlap with an AID hotspot. However, this slight preference explains only a negligible proportion of the SHMs: 13% of residues that have been mutated overlap with AID hotspots, compared to 9% of all residues. This observation indicates that hotspot motifs may be viewed as an enabler of SHMs, but that other factors are involved in determining which mutations survive clonal selections.

Figure 15:
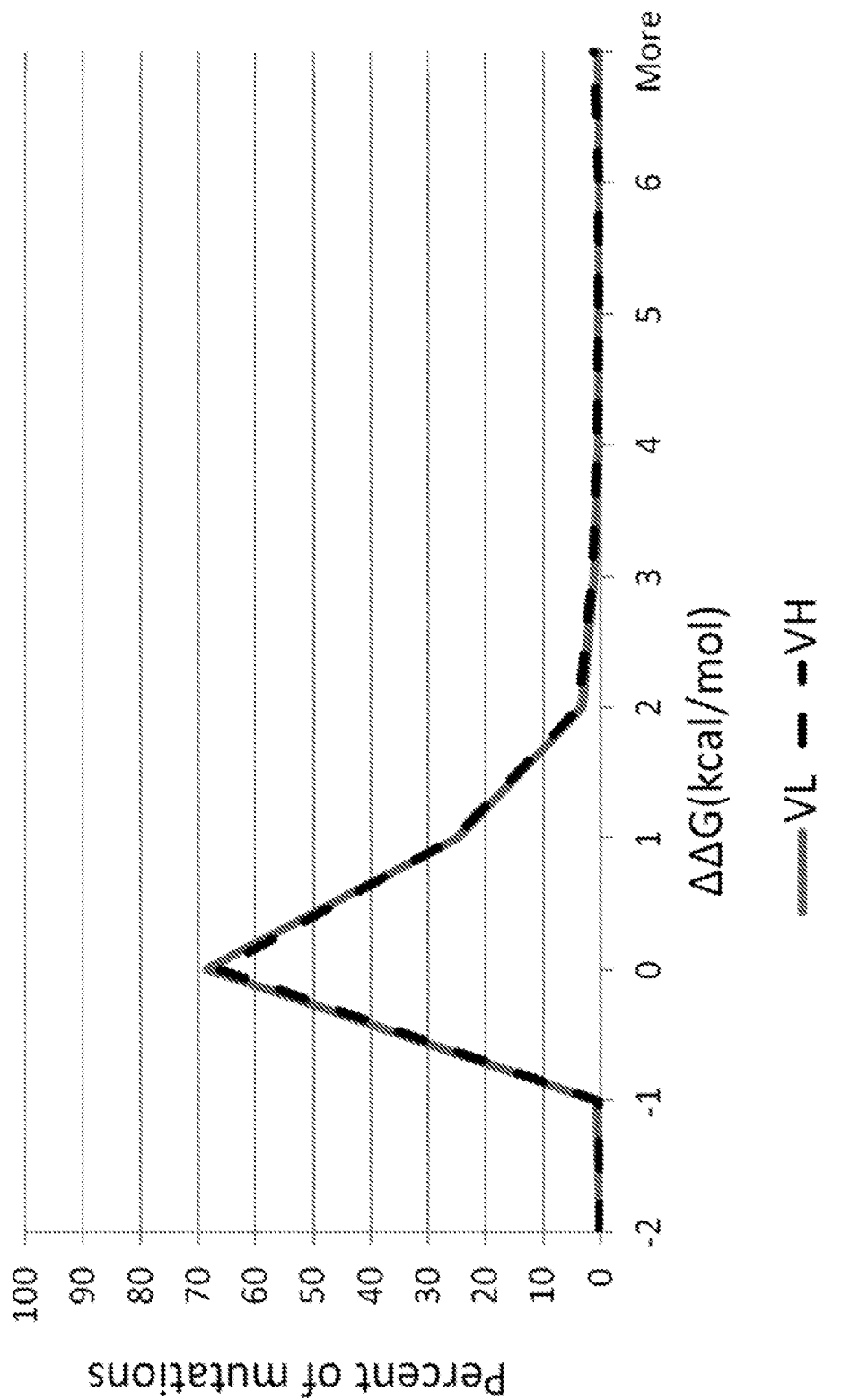
Figure 17:

C. SHMs Occur More in Heavy Chains, but Light Chain SHMs are as Important Energetically We assessed the energetic effect on the binding of the Ag for every mutated residue in the Ab by mutating it back to its germline amino acid (in silico) and predicting the effect of this mutation on the ΔΔG of binding. The calculations were performed using FoldX (Schymkowitz, J. et al., *Nucleic Acids Res* 33: W382-W388) (hereby incorporated by reference in its entirety), which uses parameters and weights derived from experimental data from a large number of mutations. Large-scale assessments of the energetic predictions by FoldX for 1030 mutants (Guerois, R. et al., *J Mol Biol* 320: 369-387 (2002) (hereby incorporated by reference in its entirety)) have shown them to be strongly correlated (R=0.83) with experimentally measured effects. Thus, while FoldX may not always provide individual accurate predictions, it may be trusted to reveal trends in large sets of mutations. Half (51%) of the SHMs had predicted ΔΔG values of 0, suggesting that they have no effect on binding, while 32% of the SHMs had positive ΔΔG values and only 17% had negative ΔΔG values, indicating that, as expected, mutating mature residues back to their germline amino acids hampers Ag binding more often than improving it. The distribution of ΔΔG values for SHMs in the VH domain is almost identical to that of SHMs in the VL domain (FIG. 15). However, 63.3% of SHMs occur in the VH domain. As the size of both domains is virtually identical, we conclude that there is a preference for SHM in the heavy chain, but each individual mutation has a similar effect regardless of the chain in which it occurs.

D. The Ag Combining Site has the Highest SHM Propensity

We divided the Ab into five non-overlapping structural regions (FIG. 3A): (a) "Ag interface", which includes residues that contact the Ag, (b) "VH-VL interface", which includes residues on each chain that contact the other chain, (c) "both interfaces", which includes residues that are implicated in both Ag and VH-VL interfaces, (d) antigen-binding region (ABR) residues that are not in contact with the Ag, and (e) "other residues". ABRs are stretches of the six hypervariable loops that roughly correspond to the CDRs (Kunik, V. et al., *PLoS Comput Biol* 8: e1002388 (2012)); Kunik, V. et al., *Nucleic Acids Res* 40:W521-W524 (2012), but cover more of the Ab-Ag interface (Kunik, V. et al., *PLoS Comput Biol* 8: e1002388 (2012). For each of the five regions, we predicted the energetic effect of each SHM on binding by mutating each SHM residue back to its germline amino acid. The strongest energetic effect was observed in residues in the Ag interface and in both interfaces (FIG. 3B). However, mutations to the VH-VL interface and mutations to the ABR residues that are not in interfaces still affect binding energy more than mutations in other areas of the Ab. Thus, although these mutations do not occur in the binding site per se, they contribute to the binding energy. We also assessed the propensity of SHMs in these five structural regions. First, we calculated the percentage of residues in each region out of the residues in the variable regions (FIG.

3C) and the percentage of SHMs (% mutations) in each region out of all SHMs. For a given region, the mutation propensity was calculated $$P_r = \log \frac{\% \ mutations_r}{\% \ residues_r}$$

where 'r' represents one of the five structural regions. If there is no preference for mutations in one region, the value of $P_r$ for that region is 0. This propensity may be used to assess the selective pressure on each of the structural regions defined. Consistent with previous reports (Ramirez-Benitez, M. C. et al., *Proteins* 45:199-206 (2001)), Raghunathan, G. et al., *J. Mol. Recog.* 25:103-113 (2012)), we found that most of the mutations (71.63%) occur outside the Ag-binding site, with 18.55%, 13.75% and 39.33% of the mutations being introduced into the regions "VH-VL interface", "ABRs not in interfaces" and "other residues", respectively. However, 87.75% of the Ab residues in the variable region do not contact the Ag. Thus, when normalizing to the relative sizes of these regions (FIG. 3C), we found that the strongest propensity for SHMs is in fact for the Ag interface and for residues in both interfaces. These regions account for 12.25% of the Ab residues but for 28.36% of the SHMs. For ABR residues that are not in interfaces, a lower but significant positive propensity is observed. The VH-VL interface has SHM probability values slightly above zero. Two-fifths (39.3%) of the SHMs occur in "other residues", which cover 59.8% of the Ab. Thus, there is a negative preference for SHMs in positions that are not in the first four regions defined above. The results in FIG. 3B, imply that the propensity for SHM and the predicted energetic contribution are correlated, as a correlation coefficient of 0.8 was calculated between the mutation probabilities and the mean ΔΔG values of SHMs in each region.

E. Germline Residues Account for Most of the Binding of the Ag

To determine which contacts contribute more to Ag binding, i.e. those that are formed by the residues mutated during SHM ("SHM contacting residues") or those that are formed by residues retained from the primary germline sequence ("germline contacting residues"), we compared their predicted energetic contribution by mutating each contacting residue to alanine and calculating the effect of this mutation on binding energy (see "Experimental procedures"). The results are shown in FIG. 4. Only 18% of the contacting residues in the mature Abs were the result of SHMs (FIG. 4A). However, the distribution of the energetic contribution of these residues is almost identical to that of germline residues that make contact with the Ag (FIG. 4B). We conclude that Ag binding is accounted for in large part by the germline Ab sequences. SHM may fine-tune this interaction by adding some contacts with similar energy distribution. It is possible that some SHMs also induce conformational changes that allow more germline residues to contact the Ag, thus improving affinity.

F. SHMs Make the Ab-Ag Interface more Similar to Other Protein-Protein Interfaces We compared the amino acid composition of SHM contacts and germline contacts with those of general protein-protein interfaces. All aliphatic hydrophobic amino acids (alanine, isoleucine, leucine, methionine, proline and valine) are under-represented in the Ab-Ag interface compared with general interfaces (FIG. 4C). However, SHMs increase the representation of aliphatic residues in the interface compared to the germline. Tyrosine, serine and tryptophan were previously reported to be abundant in Ab paratopes (Ofran, Y. et al., *J. Immunol.* 181:6230-6235 (2008)), Collis, A. V. et al., *J. Mol. Biol.* 325:337-354 (2003)). They are highly over-represented in the germline contacting residues (19.35%, 12.63% and 5.95%, respectively) but much less so in SHMs (5.53%, 8.18% and 0.71%, respectively) and in protein-protein interfaces (4.19%, 6.66% and 1.53%, respectively). Our results corroborate previous findings (Clark, L. A. et al., *J. Immunol.* 177:333-340 (2006)) showing that this over-representation is already encoded in the germline sequence. However, SHM slightly decreases this over-representation, bringing the mature interface composition closer to that of general protein-protein interfaces. Although the energy contribution of both types of Ag contacting residues is similar, their amino acid composition is remarkably different. Asparagine, phenylalanine and arginine are abundant in contacts arising during SHM, while tyrosine, serine and tryptophan are abundant in the germline contacts. We assessed the similarity between the amino acid compositions of these three types of interfaces using Jensen-Shannon divergence (Jianhua, L., *IEEE Trans Information Theory* 37:145-151 (1991) hereby incorporated by reference in its entirety) (FIG. 4D). Samples that come from the same distribution have a Jensen-Shannon divergence that is close to 0, and the Jensen-Shannon divergence increases as the differences in the compared distributions increase. The largest Jensen-Shannon divergence was found between germline contacting residues and general protein contacting residues (0.117). The greatest similarity was found between protein-protein interfaces and SHM contacting residues, with a Jensen-Shannon divergence of 0.054, which is smaller than the Jensen-Shannon divergence between SHM contacting residues and germline contacting residues (0.077). Thus, although germline contacts differ substantially from general protein-protein interfaces, SHM contacts, which are more similar to general protein-protein interfaces, make the final composition of the mature Ab interface more similar to protein-protein interfaces, with a Jensen-Shannon divergence of 0.0973.

G. Structure and Function Drive the Propensity for Mutation

To understand the role of different amino acids in SHM and the differences between the structural regions, we further analyzed the propensities for mutation in germline amino acids during SHM. As shown in FIG. 5, alanine and serine are mutated more than expected by chance across all structural regions, while glycine, proline and leucine are mutated less than expected. Alanine, methionine and valine are the only aliphatic hydrophobic amino acids that are mutated significantly more than expected by chance. This enrichment holds for valine only in the VH-VL interface and for methionine in all structural regions except 'both interfaces'.

All polar amino acids show a very distinct preference across these four structural regions. Tyrosine, which is highly important in Ag binding due to its over-representation in Ab ABRs (Kunik, V. et al., *Prot. Eng. Des. Sel.* 26:599-609 (2013), is actually a preferred target for substitution in ABRs residues that are not in interfaces and in the VH-VL interface. The only exception is the Ag interface, in which tyrosine is slightly protected from substitutions. Threonine, which has also been suggested to be over-represented in Ag interfaces (Ofran, Y. et al., *J. Immunol.* 181:6230-6235 (2008)), is mostly neutral to mutation, but is mutated less than expected in the VH-VL interface. Tryptophan is a slightly preferred target for mutation among the residues that are part of both interfaces, and is highly under-mutated in all other regions. Asparagine and glutamine show opposite patterns. While asparagine is over-represented, glutamine is under-represented in both the VH-VL interface and ABRs that are not in any interface. Asparagine also has high mutability in both interfaces, and glutamine is mutated less than expected in the Ag interface. As for the charged amino acids, arginine shows a negative propensity for mutation in the VH-VL interface and in both interfaces. Lysine shows a positive propensity for mutations in ABRs that are not in interfaces. Glutamic acid, aspartic acid and histidine are all less mutated than expected in the Ag interface and in both interfaces.

H. Five Amino Acids Account for 49% of Mutations in the Ag Interface Region

Figure 23:
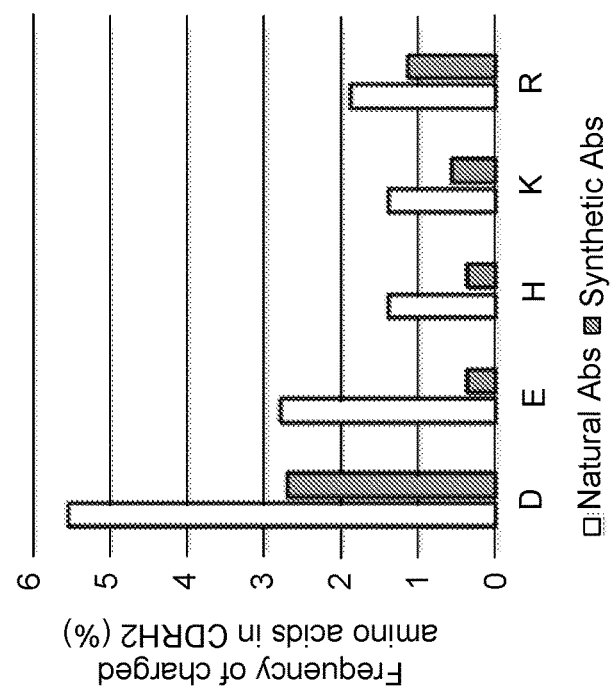
Figure 23:
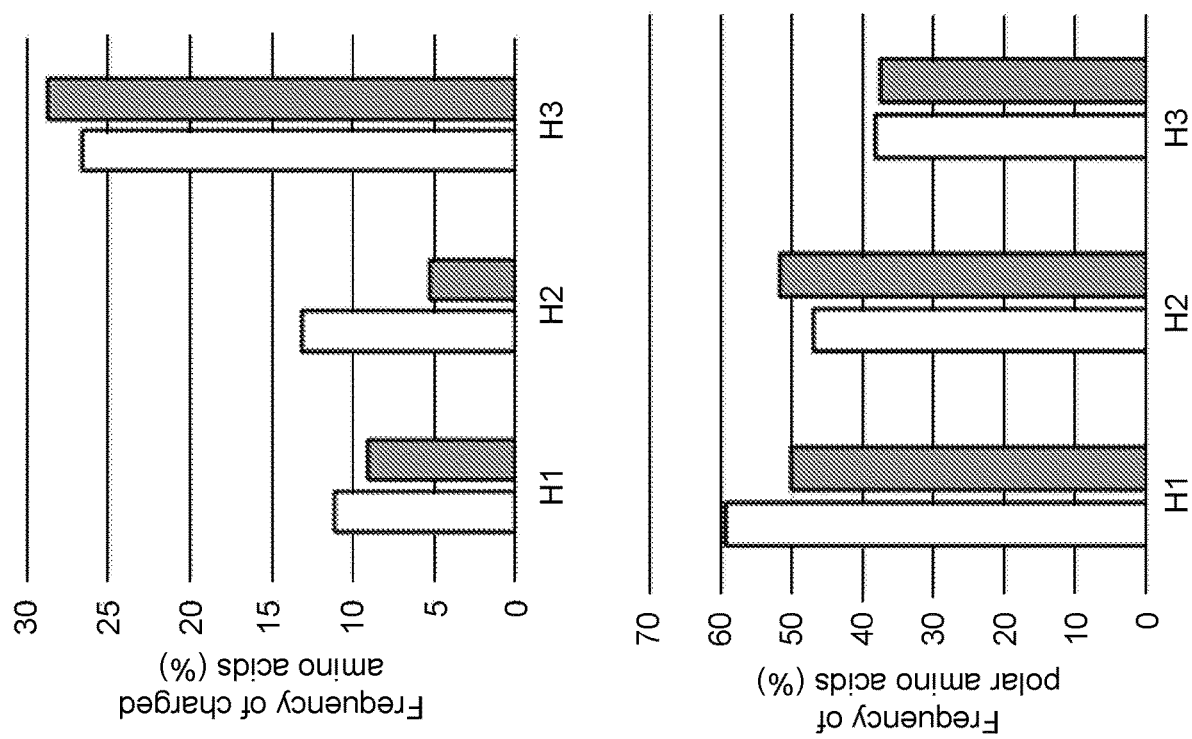

FIG. 6 shows the amino acid composition of the residues that are introduced during SHM. The amino acid composition for SHMs in each structural region was calculated as the percentage of "Mutations to AA1" out of the "Mutations in the regions". As "Mutations to AA1" is the number of mutation to a specific amino acid and "Mutations in the regions" is the total number of mutations in the structural region. Different factors may affect the frequency of introducing a certain amino acid into the sequence of the Ab, such as codon redundancy, number of base changes required to introduce a new residue, the frequency of the original codon in germline sequences, the frequency of the amino acid within all protein sequences, the probability of the substitution in general, and even codon usage. As shown in FIG. 6, which presents the raw frequencies of substitutions within each region, there are significant differences for many residues in terms of their propensities to be introduced into the different regions. FIG. 23 shows the same frequencies normalized by the number of codons each amino acid has in the genetic code. Interestingly, asparagine, aspartic acid and phenylalanine remain highly favored, and tryptophan and cysteine remain the most disfavored.

The propensities for substitutions in FIG. 6 show that, in all regions, asparagine is introduced more than glutamine. Aspartic acid is introduced more than glutamic acid in all regions except the VH-VL interface. This may be due to the smaller size of aspartic acid and asparagine compared with glutamic acid and glutamine. Histidine, lysine and proline are introduced into all regions rather moderately. Valine and isoleucine are commonly introduced only in ABR positions that are not in interfaces. Alanine is introduced often into the VH-VL interface and into ABRs that are not in interfaces, but substantially less into the Ag interface. Phenylalanine, glycine, asparagine, arginine, serine and threonine are popular additions to all structural regions. The VH-VL interface, which is made up of two interacting β sheets, is rich in hydrophobic or short polar amino acids (phenylalanine, serine, threonine, alanine, leucine and glycine) that are introduced during the SHM process. When focusing only on the Ag interface, the most frequent substitutions are asparagines. Other common substitutions in the Ag interface are arginine, serine, threonine and aspartic acid. These five polar amino acids account for 49% of mutations in the Ab-Ag interface. Glycine and phenylalanine are the next most prevalent, probably due to the small size of glycine (Dayhoff, M. O. et al., "A model of evolutionary change in proteins" In *Atlas of Protein Sequence and Structure* (Dayhoff Mo., ed), vol 5, pp. 345-352 (1978). *National Biomedical Research Foundation*, Washington, D.C. and the structure similarity between phenylalanine and tyrosine, an amino acid that is highly represented in the germline sequence (37.5% of mutated tyrosine are substituted by phenylalanine).

Figure 7:
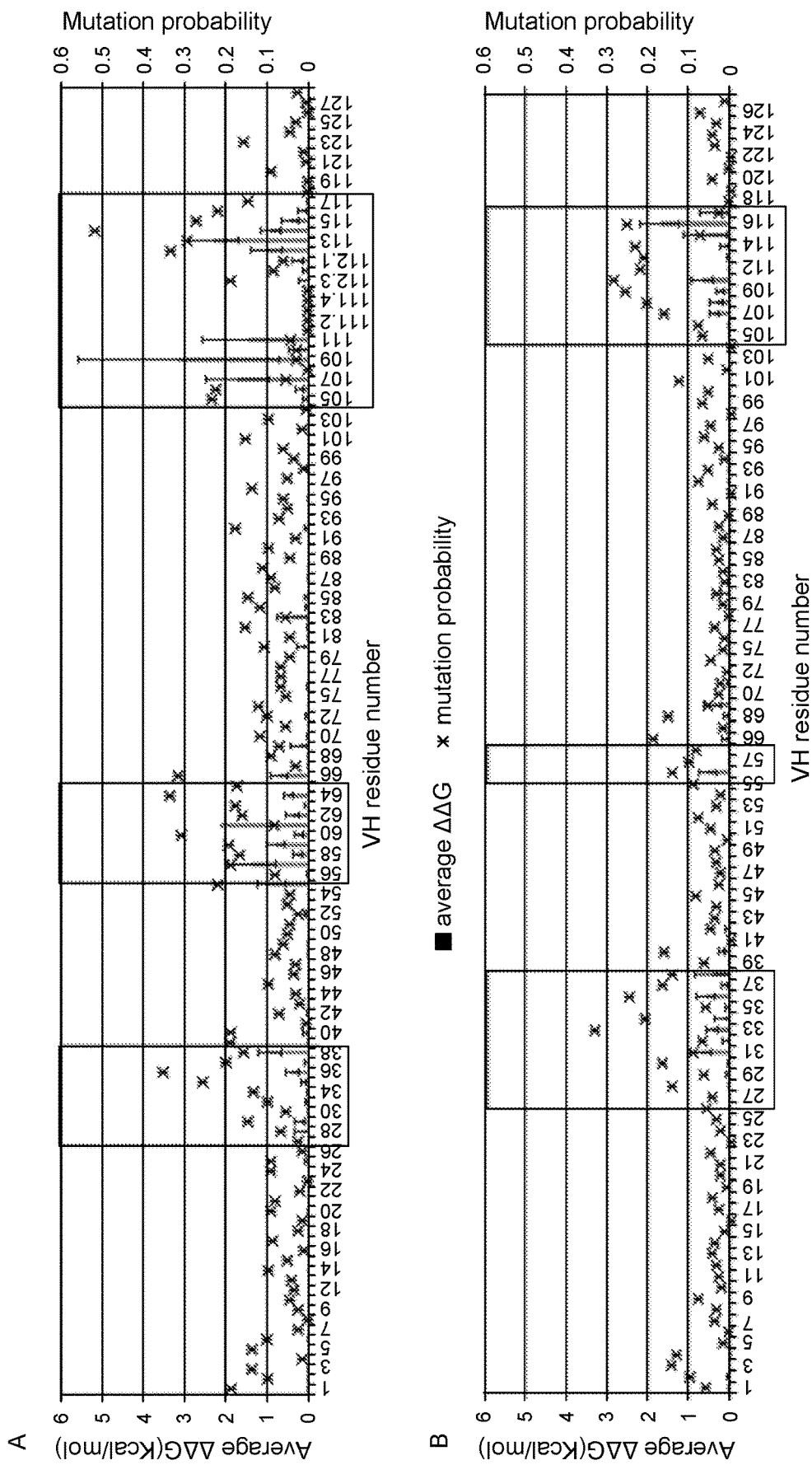
Figure 8:
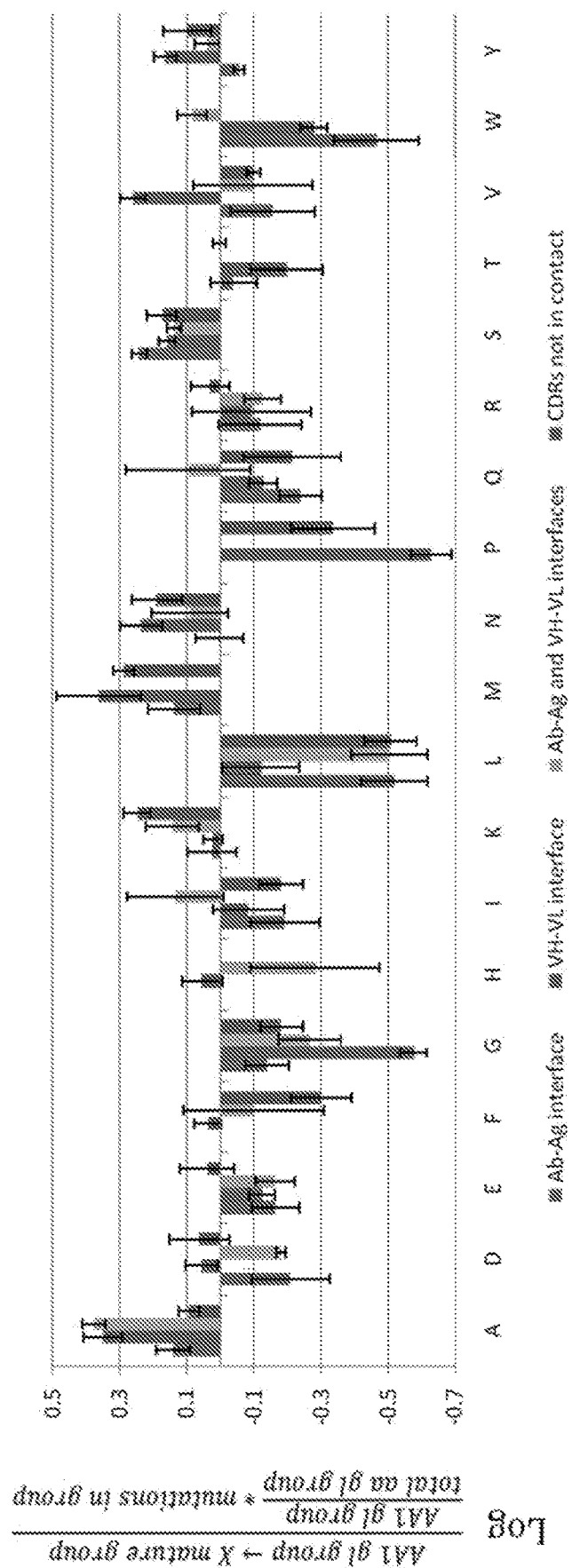
Figure 9A:
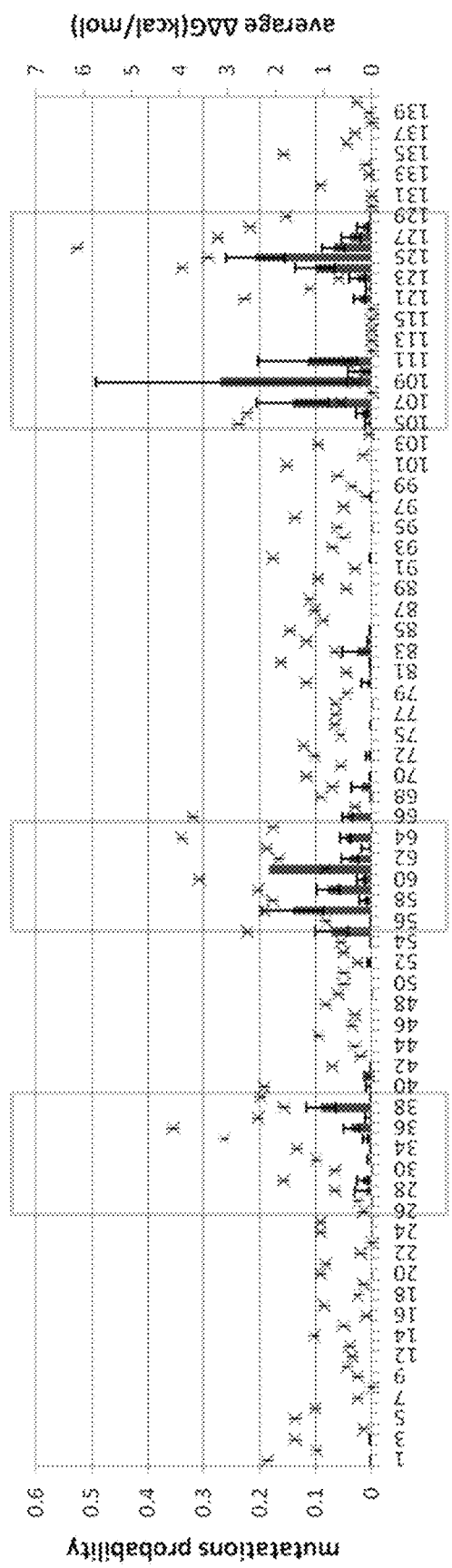
Figure 9B:
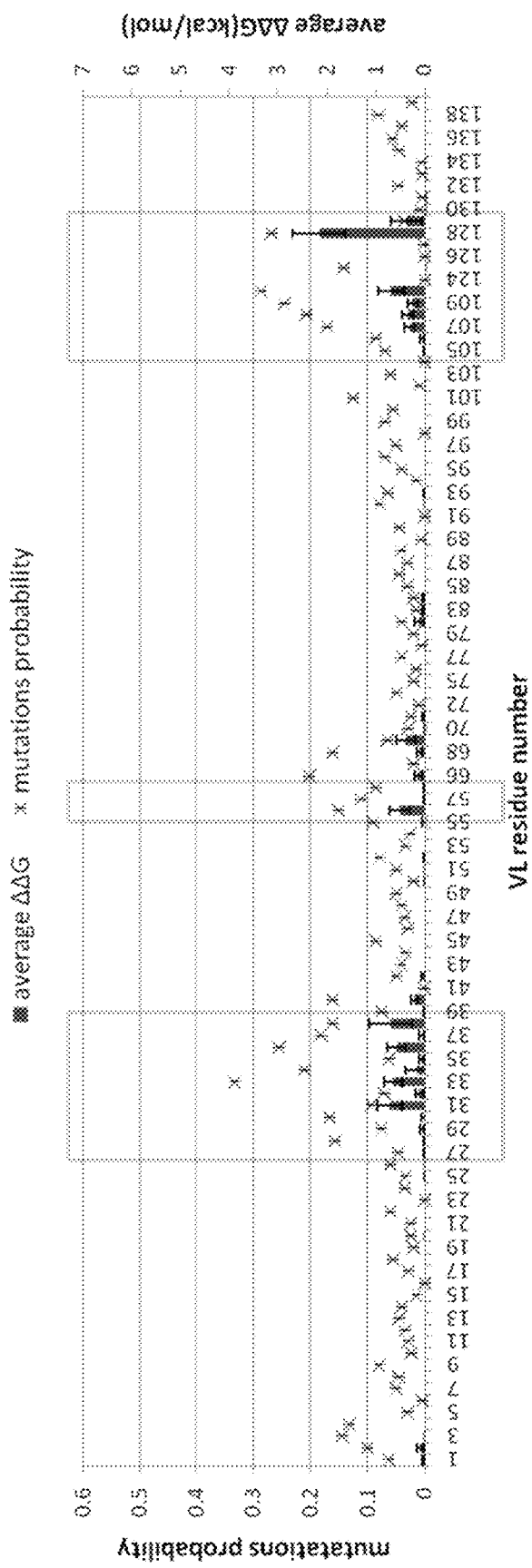
Figure 13:
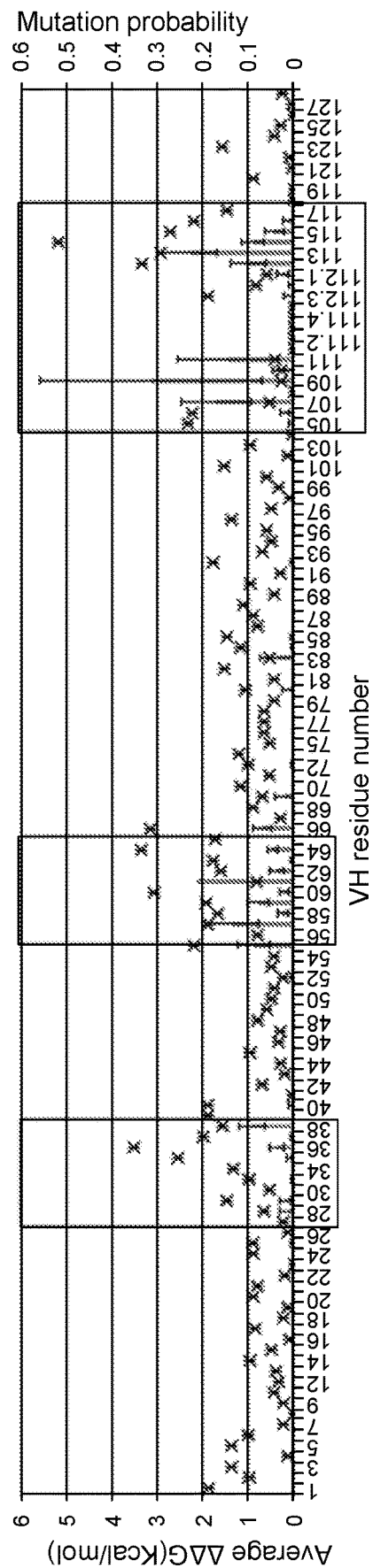
Figure 13:
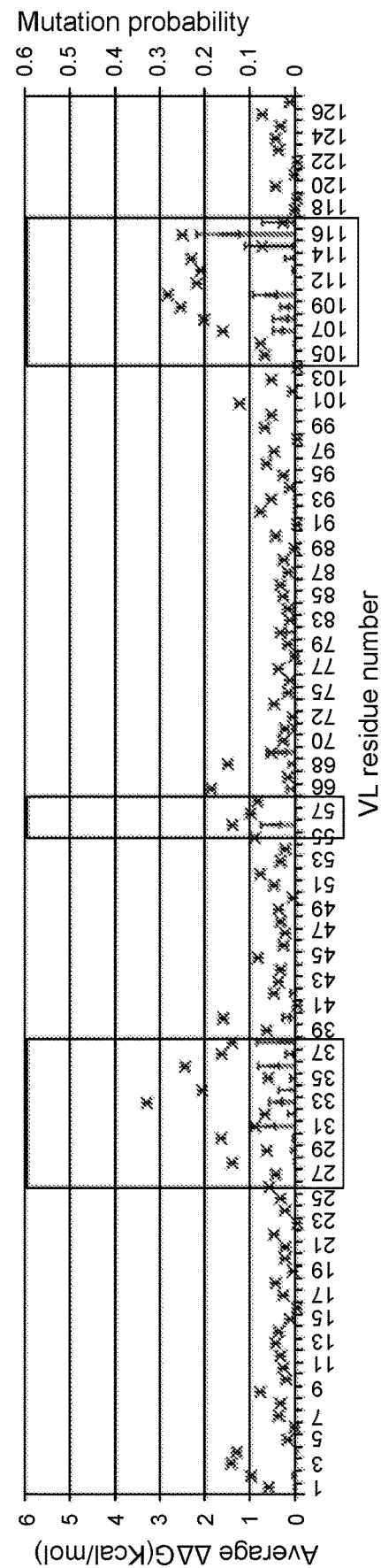
Figure 14:
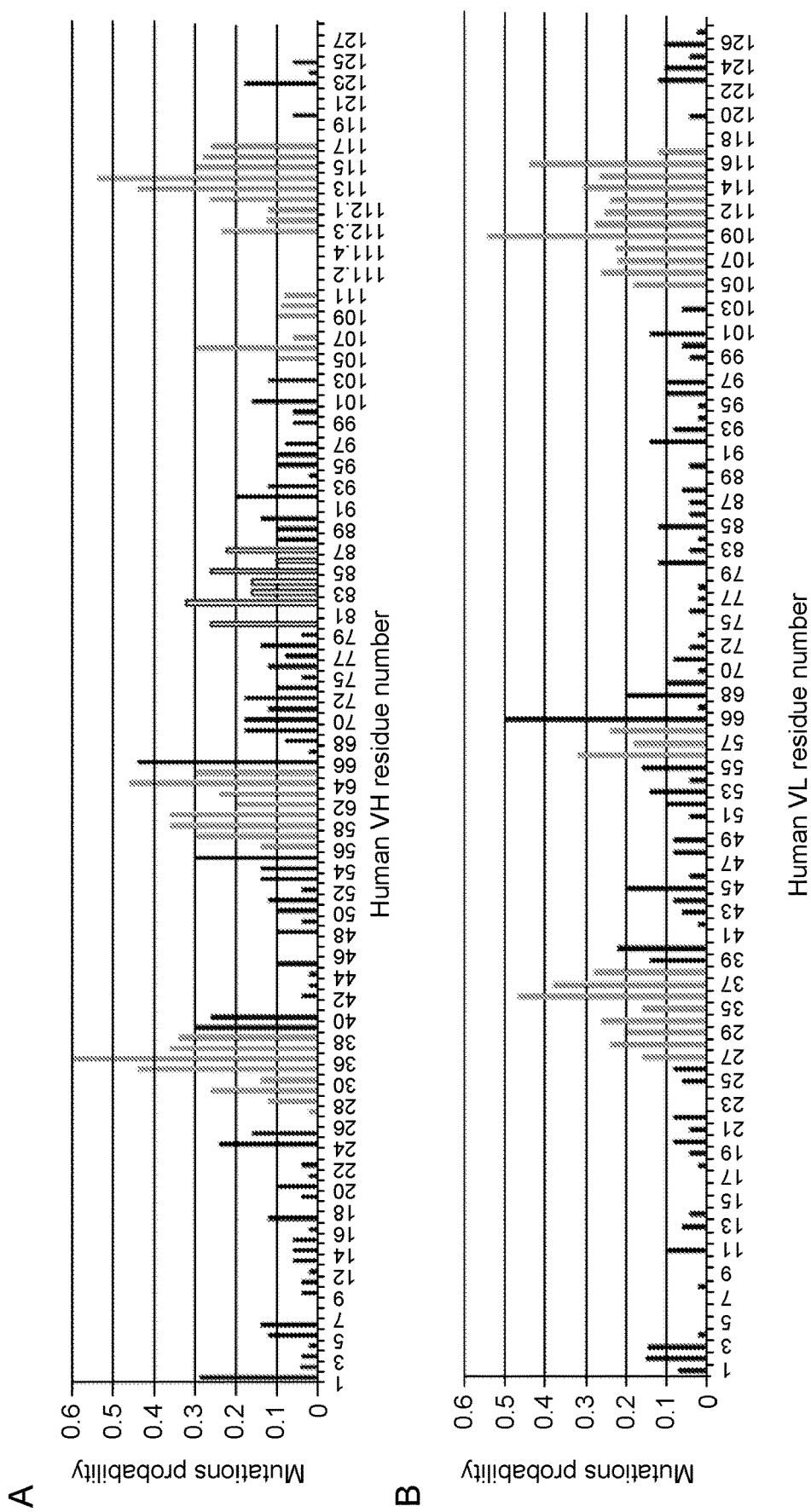
Figure 14:
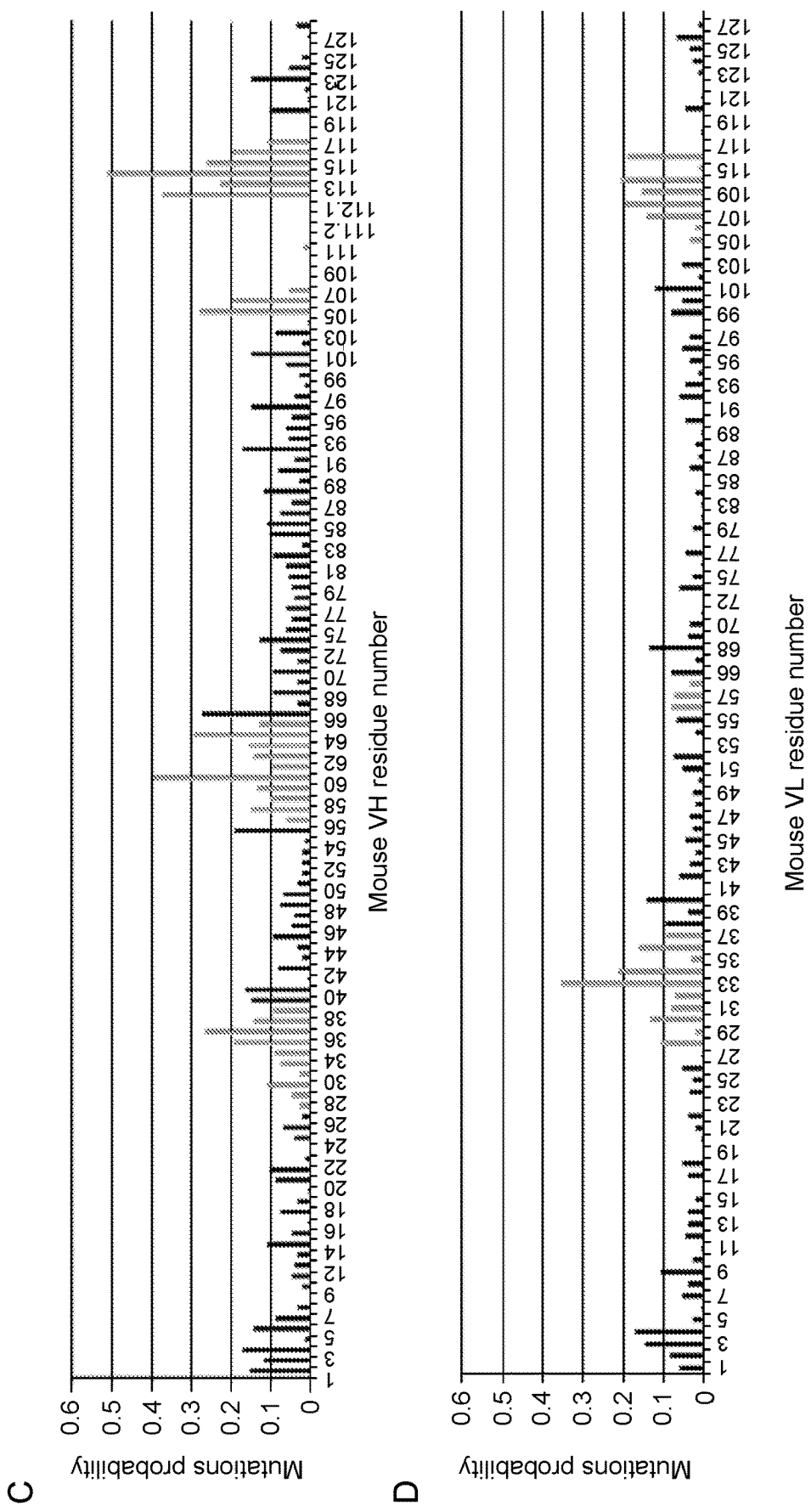

I. Mutation Probability and Energy Contribution Reveal Promising Positions for Affinity Enhancement Rational design of high-affinity Abs requires targeting of Ab positions for mutations. Our analysis identifies such positions based on in vivo SHM data. FIG. 7 shows the probability of mutations for each Ab position (according to IMGT numbering for the V domain (Lefranc, M. P. et al., *Dev Comp Immunol* 27: 55-77 (2003) (hereby incorporated by reference in its entirety) and the mean contribution to binding energy of the SHMs in these positions across all Abs in the dataset. For CDRH3, it is not feasible to identify the germline sequence, as it contains a variable number of residues that originate from the D gene fragment. Thus, the data for this CDR do not include the D regions. SHMs are enriched in the CDRs and their vicinity (see also Fig. S3). This observation is in agreement with previous studies (Clark, L. A. et al., *J. Immunol.* 177, 333-340; Tomlinson I M, et al. The imprint of somatic hypermutation on the repertoire of human germline V genes. J Mol Biol 256: 813-817 (1996).] and consistent with the fact that ~80% of the Ag-binding residues are within the CDRs (Kunik, V. et al., *PloS Comput. Biol.* 8:e1002388 (2012)). However, an additional region with high mutation probability was found between residues 80 and 87 in the human VH domain (FIG. 13). This is consistent with previous reports on the so-called CDRH4 that was suggested to exist in this area (Raghunathan, G. et al., *J. Mol. Recog.* 25:103-113 (2012)); Capra, J. D. et al., *Proc. Natl. Acad. Sci. USA* 74:845-848 (1974). Positions 80-87 in the VH domain form a loop (Fig. S4) similar to the CDRs, accounting for 1.36% of the human Ab-Ag interactions and 0.3% of the mouse interactions. This is in agreement with the high SHM probability that we observed in this region in human sequences but not in mouse sequences (FIG. 13).

The regions in the Ab that have high average $\Delta\Delta G$ values for mutating their residues back to the germline amino acids overlap to some extent with regions that have a high mutation probability. However, not all CDR positions undergo substitutions that contribute to binding. For example, CDRH2 (VH positions 56-65) has high mutation probabilities for most of its residues. However, positions 63 and 65 have, on average, no energetic effect on binding despite their high probability for mutations. Positions that are frequently mutated and also show a substantial effect of SHMs on Ag-binding energy, such as 38, 55, 57, 59, 112, 113 and 114 on the VH domain and 110 and 116 on the VL domain, may be promising targets for in vitro affinity enhancement.

J. Discussion

Many of the insights into the structural basis of in vivo affinity maturation were obtained from analyses of SHMs in a single pair, or in several pairs, of germline and mature Abs Li Y, Li H, Yang F, Smith-Gill S J & Mariuzza R A (2003) X-ray snapshots of the maturation of an antibody response to a protein antigen. *Nat Struct Biol* 10, 482-488. Midelfort K S, Hernandez H H, Lippow S M, Tidor B, Drennan C L & Wittrup K D (2004) Substantial energetic improvement with minimal structural perturbation in a high affinity mutant antibody. *J Mol Biol* 343, 685-701. Chong L T, Duan Y, Wang L, Massova I & Kollman P A (1999) Molecular dynamics and free-energy calculations applied to affinity maturation in antibody 48G7. *Proc Natl Acad Sci USA* 96, 14330-14335. Wong S E, Sellers B D & Jacobson M P (2011) Effects of somatic mutations on CDR loop flexibility during affinity maturation. *Proteins* 79, 821-829.-Schmidt A G, Xu H, Khan A R, O'Donnell T, Khurana S, King L R, Manischewitz J, Golding H, Suphaphiphat P, Carfi A, et al. (2013) Preconfiguration of the antigen-binding site during affinity maturation of a broadly neutralizing influenza virus antibody. *Proc Natl Acad Sci USA* 110, 264-269. Thorpe I F & Brooks C L 3rd (2007) Molecular evolution of affinity and flexibility in the immune system. *Proc Natl Acad Sci USA* 104, 8821-8826., Acierno J P, Braden B C, Klinke S, Goldbaum F A & Cauerhff A (2007) Affinity maturation increases the stability and plasticity of the Fv domain of anti-protein antibodies. *J Mol Biol* 374, 130-146.]. Large-scale studies that attempted to elucidate the principles that guide SHM reached contradictory conclusions regarding preference for SHMs in the Ab-Ag interface (Clark L A, Ganesan S, Papp S & van Vlijmen H W (2006) Trends in antibody sequence changes during the somatic hypermutation process: 333-340; Dorner T, Brezinschek H P, Brezinschek R I, Foster S J, Domiati-Saad R & Lipsky P E (1997) Analysis of the frequency and pattern of somatic mutations within nonproductively rearranged human variable heavy chain genes. *J Immunol* 158, 2779-2789; Ramirez-Benitez M C & Almagro J C (2001) Analysis of antibodies of known structure suggests a lack of correspondence between the residues in contact with the antigen and those modified by somatic hypermutation. *Proteins* 45: 199-206; Raghunathan G, Smart J, Williams J & Almagro J C (2012) Antigen-binding site anatomy and somatic mutations in antibodies that recognize different types of antigens. *J Mol Recog* 25: 103-113.). Our division of the Ab into various structural regions, and the calculation of mutation probability and the energy effects of SHMs in each region, reveal that the highest propensity for SHMs is in Ag-binding regions (Ag interface and both interfaces). These regions also provide the greatest energetic contribution to Ag binding. These results are consistent with the selection of B cells based on Ag binding and with previous studies that showed fine-tuning of the Ag-binding site through SHMs (Li Y, Li H, Yang F, Smith-Gill S J & Mariuzza R A (2003) X-ray snapshots of the maturation of an antibody response to a protein antigen. *Nat Struct Biol* 10, 482-488: Chong L T, Duan Y, Wang L, Massova I & Kollman P A (1999) Molecular dynamics and free-energy calculations applied to affinity maturation in antibody 48G7. *Proc Natl Acad Sci USA* 96, 14330-14335). Although to a lower extent than the regions involved Ag binding, ABR residues that are not in the interfaces and residues in the VH-VL interface are both favored targets for mutations and make a substantial energetic contribution to Ag binding. This is consistent with previous studies that showed how internal interface stabilization (Acierno J P, Braden B C, Klinke S, Goldbaum F A & Cauerhff A (2007) Affinity maturation increases the stability and plasticity of the Fv domain of anti-protein antibodies. *J Mol Biol* 374, 130-146.) and increased VH-VL interface shape complementarity (Midelfort K S, Hernandez H H, Lippow S M, Tidor B, Drennan C L & Wittrup K D (2004) Substantial energetic improvement with minimal structural perturbation in a high affinity mutant antibody. *J Mol Biol* 343, 685-701). result in enhanced Ag binding.

DNA motifs that enhance targeting of the AID enzyme have been the focus of many studies that attempted to identify SHM sites. Such DNA hotspot motifs were previously suggested to play an important role in the formation of SHMs (Darner T, Foster S J, Farner N L & Lipsky P E (1998) Somatic hypermutation of human immunoglobulin heavy chain genes: targeting of RGYW motifs on both DNA strands. *Eur J Immunol* 28, 3384-3396). However, our results indicate that the mature Ab sequence is determined by the affinity and possibly the stability of the Ab. The lack of correlation between the extent to which an amino acid is located within hotspots and its frequency among mutated positions suggests that structural and functional considerations play a much more important role than the presence of AID hotspots.

Our analysis of SHM, germline and general protein-protein interfaces suggested some evolutionary insights. Tyrosine and tryptophan, which are large, flexible, amphipathic amino acids, were previously suggested to be highly represented in the Ag interfaces, and have been proposed to allow binding of several structurally similar Ags (Mian I S, Bradwell A R & Olson A J (1991) Structure, function and properties of antibody binding sites. *J Mol Biol* 217, 133-151.) However, the affinity maturation process decreases their representation and increases the representation of aliphatic hydrophobic amino acids. Both SHM contacts and protein-protein contacts are the result of specific evolution and optimization of contacts, while germline-Ag contacts occur between partners that have never met before. This may explain the abundance of germline interface residues that may form several different kinds of contacts, and also the higher similarity between protein-protein interfaces and SHM contacting residues. This observation is consistent with a previous study that suggested that Ab affinity maturation and protein-protein interface evolution are guided by similar principles (*J Riot Chem* 285: 3865-3871).

The $\Delta\Delta G$ values in this study were predicted by FoldX (Guerois R, et al. Predicting changes in the stability of proteins and protein complexes: a study of more than 1000 mutations: 369-387 (2002) (hereby incorporated by reference in its entirety). While there may be other tools that allow energetic assessment of individual mutations, FoldX enables rapid assessment of a large number of SHMs. An independent assessment has shown that FoldX is particularly good in assessment of the energetic effect of mutations to amino acids other than alanine and mutations of residues located in loops (Potapov V, et al., Assessing computational methods for predicting protein stability upon mutation: good on average but not in the details 553-560 (2009). Previous studies have shown that FoldX may be used to identify trends in the evolution of protein function (Tokuriki N, et al., How protein stability and new functions trade off PLoS Comput Biol 4, e1000002 (2008); Tokuriki N, et al., The stability effects of protein mutations appear to be universally distributed 1318-1332 (2007)). Furthermore, it has recently been used for the study Ab-Ag interactions (Kunik V, et al. Structural consensus among antibodies defines the antigen binding site. PLoS Comput Biol 8, e100238 (2012). Kunik V & Ofran Y. The indistinguishability of epitopes from protein surface is explained by the distinct binding preferences of each of the six antigen-binding loops: 599-609 (2013). The FoldX energy function also includes scoring parameters for the entropic cost of mutation. However, these parameters are calculated based on theoretical data and have been acknowledged to be a crude estimation of the entropy (Schymkowitz J, et al. The FoldX web server: an online force field. *Nucleic Acids Res* 33: W382-W388 (2005). It has been shown that loss of flexibility in the Ab paratope and thus a lower entropic cost of the interaction is an important aspect in Ab affinity maturation (Wong S E, et al. Effects of somatic mutations on CDR loop flexibility during affinity maturation, *Proteins* 79: 821-829 (2011); Schmidt A G, et al., Preconfiguration of the antigen-binding site during affinity maturation of a broadly neutralizing influenza virus antibody, *Proc Natl Acad Sci USA* 110: 264-269 (2013).

Thorpe I F & Brooks C L 3rd, Molecular evolution of affinity and flexibility in the immune system, *Proc Natl Acad Sci USA* 104 8821-8826 (2007). Quantification of such effects requires long molecular dynamics simulations or experimental procedures. Such methods are not applicable for a large number of Ab-Ag complexes, thus the estimation of paratope rigidification is beyond the scope of this study.

The Ab-Ag dataset we used consists of 196 non-redundant Ab-Ag complexes. As more Ab-Ag complexes become available, it will be possible to also apply this approach to Ab-hapten interaction, which is currently not practical, and even to the interfaces with specific Ags such as gp120 or hemagglutinin, to elicit SHM patterns that are unique for that Ag. For example, it has recently been shown that Abs that broadly neutralize HIV are characterized by a remarkably high number of SHMs (Scheid J F, et al., Broad diversity of neutralizing antibodies isolated from memory B cells in HIV-infected individuals, *Nature* 458: 636-640 (2009); Kwong P D & Mascola J R, Human antibodies that neutralize HIV-1: identification, structures, and B cell ontogenies, *Immunity* 37: 412-425 (2012); Wu X, et al., Rational design of envelope identifies broadly neutralizing human monoclonal antibodies to HIV-1, *Science* 329: 856-861 (2010). and may require also SHMs in their framework regions (Klein F, et al. Somatic mutations of the immunoglobulin framework are generally required for broad and potent HIV-1 neutralization, *Cell* 153: 126-138 (2013).

Over recent decades, Abs have become one of the most effective and popular tools in biotechnology and biomedicine (Maynard J & Georgiou G, Antibody engineering, *Annu Rev Biomed Eng* 2: 339-376 (2000)) and more than 30 Abs and Ab derivatives have been approved for therapeutic use by the US Food and Drug Administration (Beck A, et al., Strategies and challenges for the next generation of therapeutic antibodies, *Nat Rev Immunol* 10: 345-352 (2010). Therapeutic and diagnostic Abs frequently require engineering to enhance the affinity of Abs raised in immunized animals or selected by library screens. This step is important to expand detection limits, extend dissociation half-life, decrease drug dosage and increase drug efficiency (Lippow S M, et al., Computational design of antibody-affinity improvement beyond in vivo maturation, *Nat Biotechnol* 25: 1171-1176(2007). The structural and biophysical principles identified here may allow more focused in vitro design of Abs with enhanced affinities for use in building the libraries of the invention.

Example 4

Antibody Repitoping

1. Modeling

A model of the antigen of interest, in this case IL-17A in the receptor bound conformation, was generated using Modeler as implemented in the Discovery Studio suite.

2. Docking

The model was then docked against a large database of antibody three-dimensional structures using ZDOCK as implemented in Discovery Studio. Various poses were screened in order to identify poses that have "native like" properties. For the IL-17A antibody, poses providing optimal blocking of the binding site of the IL17AR were sought. A docking pose of antibody 2ZJS (PDB id) and the model of IL-17A was selected as a template for library design.

3. Libraries

Positions within the CDRs of the antibody were selected for the introduction of variability for library design according to the methods described infra. For the initial library based on the 2ZJS antibody from the PDB, docked to IL-17A as described above, five positions were selected for variation (1 on chain H, 4 on chain L), yielding a library with diversity (at the amino acid level) of ~500,000. In addition to the 2ZJS-based library, other libraries were designed based on the docking models with the following PDB structures: 2ADG, 1GPO, 3A6C, 3C09, 1DFB Libraries based on 2ADG and 2ZJS yielded IL-17A binders.

4. Testing

The initial selection of libraries (2ZJS and 2ADG) against IL-17A yielded several clones that bound the antigen specifically with sub-micromolar affinity, based on titrations performed on the yeast.

After each round of selection the surviving clones were deep-sequenced to analyze which variants are subject to selective pressures and which substitutions are favored or disfavored in the various positions. The results of this analysis were used to design an improved library. Briefly, positions that are under selective pressure (i.e. mutations in these positions improve or hamper binding) are positions that have an effect on the interface. This information can be used to refine the original model of antibody-antigen complex, and, in turn will allow another iteration of the process described above, yielding new libraries with more focused variations.

5. Another Iteration:

Clones selected from this library as IL-17A binders, were utilized as the basis for the introduction of additional variation to improve affinity and utility. Specific positions within the antibody were selected based on sequence analysis (for example, Blast), positions suggested in the literature, and/or the analysis of deep sequencing data from the initial library. Based on these analyses, a next-generation library was designed.

In this particular case, we were able to identify several positions in two of the libraries that were under selection. For example, in the library that was based on 2ZJS we observed that in two neighboring positions we saw a clear overrepresentation of aromatic residues. This round of selection culminated in a scFv that show full cross blocking of the soluble IL17Ra.

Figure 10:
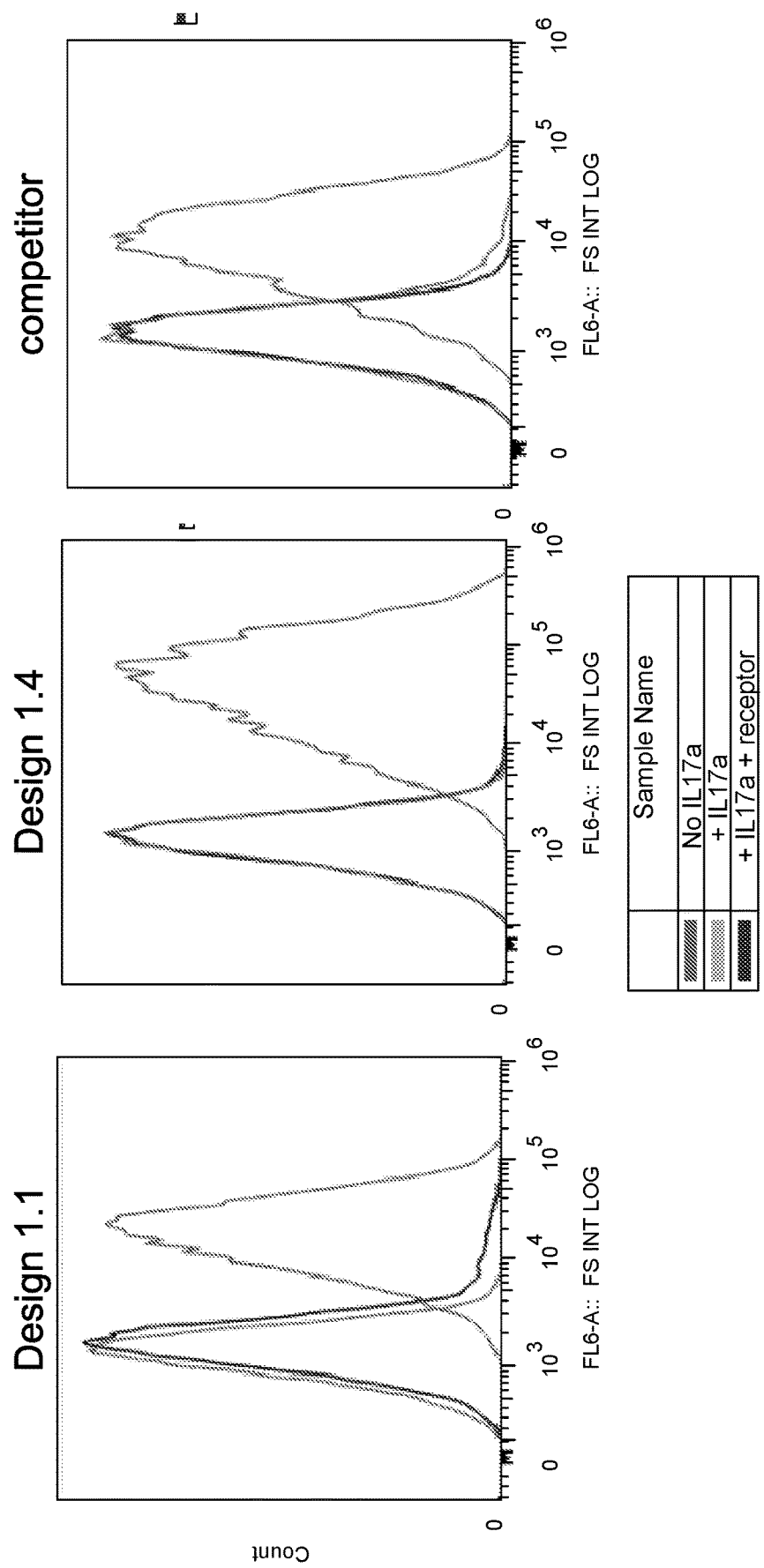

6. Isolate Binders:

FIG. 10 shows the binding of two antibodies, isolated from two different libraries to IL17a. As a benchmark we also show the binding of a publicly available antibody against IL17a, developed by Medimmune (Gerhardt et al., 2009) (hereby incorporated by reference in its entirety). Importantly, the Medimmune antibody is known to bind IL17a in a certain site and to exclude binding of IL17a mostly by stabilizing a conformation that does not permit IL17-RA binding. Our strategy was to exclude IL17-RA binding by binding a different epitope. Hence, if our antibodies indeed bind the desired epitope, we expect them to fully compete with IL17Ra, but not with the Medimmune antibody. FIG. 10 shows that our antibody competes with IL17Ra. Additional experiments have shown that our antibody does not compete with the Medimmune antibody.

Figure 11:
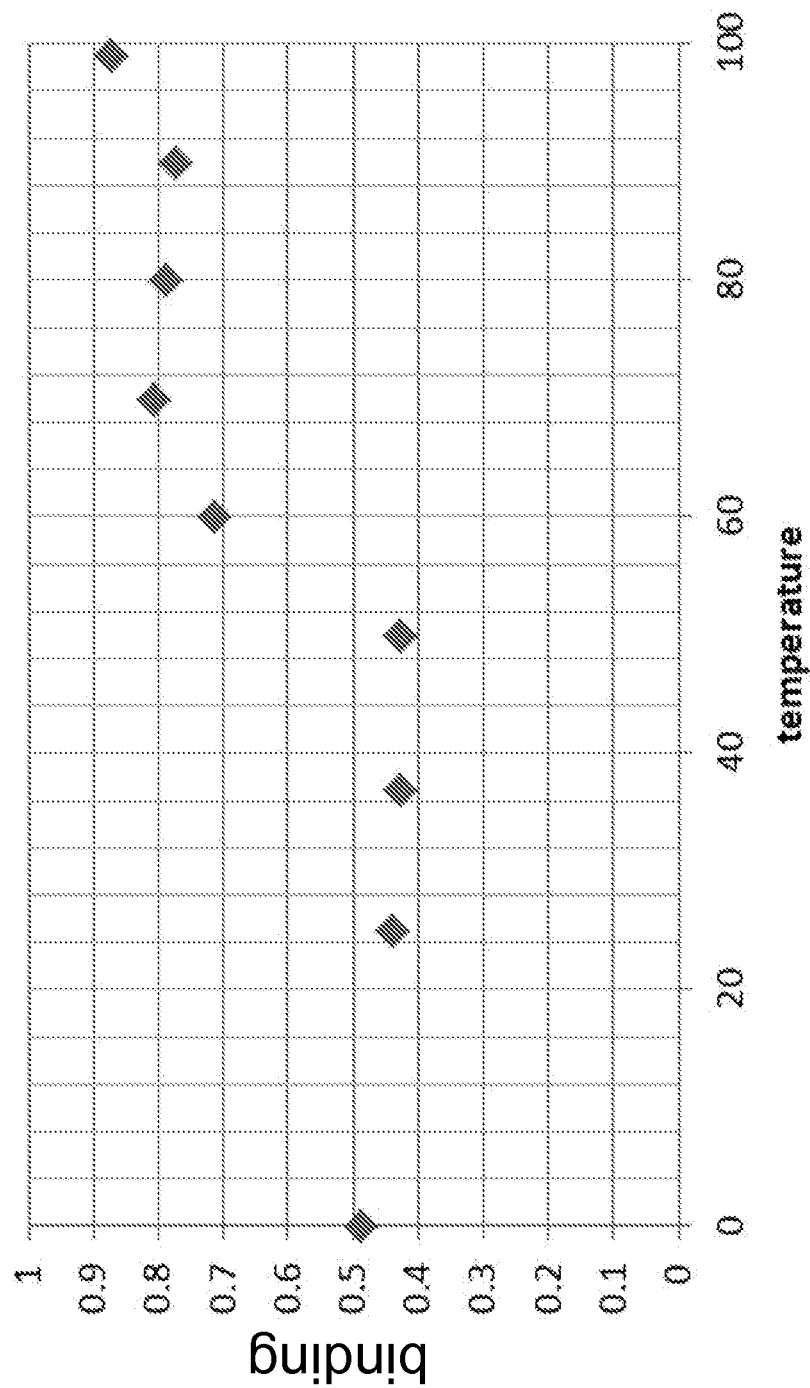
Figure 12:
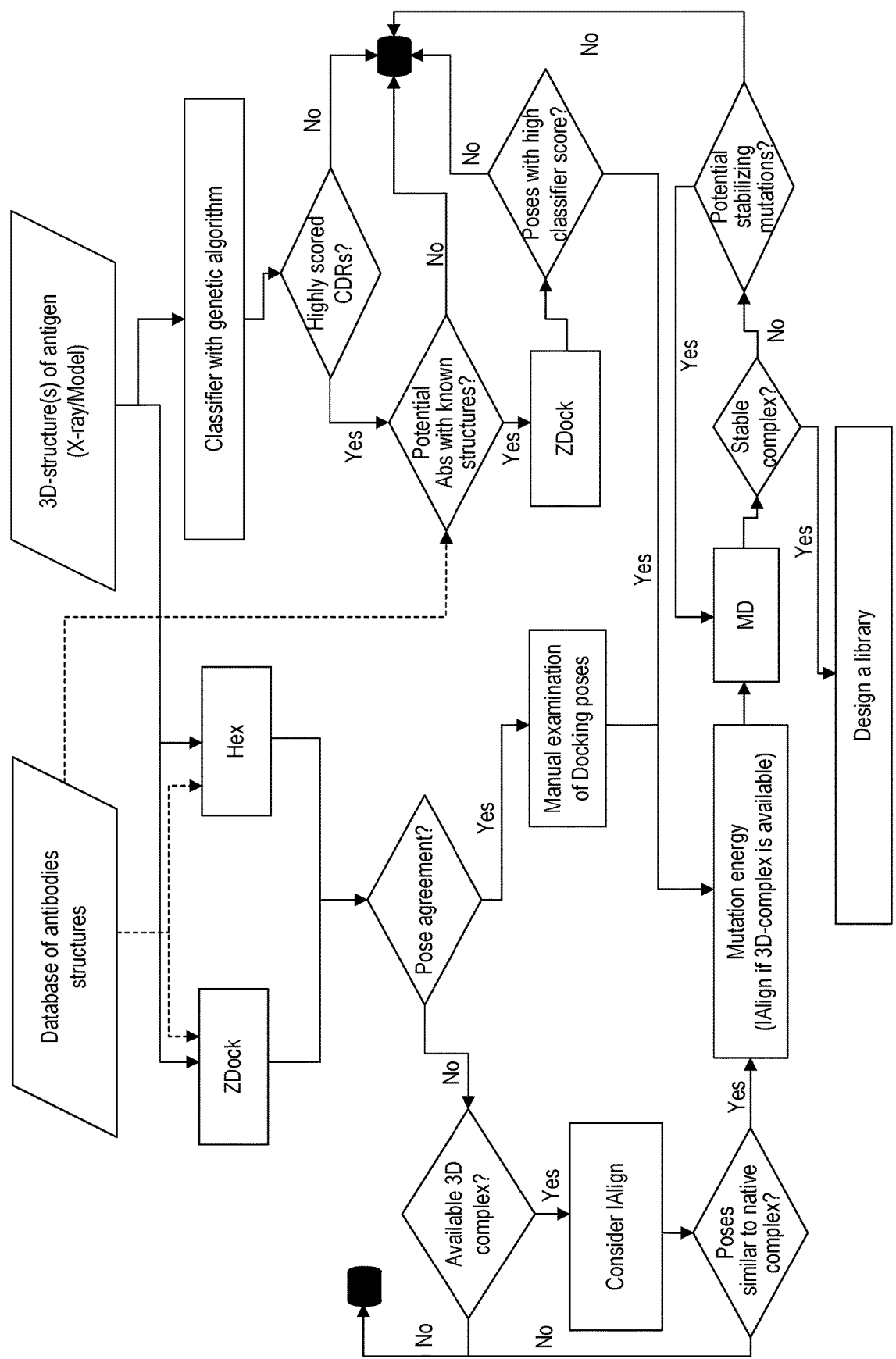

Additional analysis of the soluble scFv has shown that it does not only bind the IL17a but is also highly thermostable, as shown in FIG. 11.

Example 5

Differences Between Synthetic and Natural Antibodies

A. Background

A critical question, therefore, in designing synthetic libraries is to what extent the resulting Abs are similar to natural Abs in the way they recognize and bind the Ag. Indeed, good therapeutic biomolecules do not have to mimic natural Abs. However, it is often assumed that libraries that better mimic natural Abs and natural diversity are more likely to yield better binders with better profile. Some novel approaches for library design attempt to introduce diversity that will better imitate natural diversity while also yielding Abs with improved biophysical properties. For example, the human combinatorial antibody library (HuCAL) was created to represent the most frequently used germline families and was optimized to obtain high expression and low aggregation in *E. coli*. The CDRs cassettes were designed to mimic the length and amino acid composition of naturally occurring Abs (Knappik A, et al., *J Mol Biol* 296:57-86 (2000); Rothe C, et al., *J Mol Biol* 376:1182-200 (2008)) (herein incorporated by reference in its entirety). Sidhu et al. (Sidhu S S, et al. *J Mol Biol* 338:299-310 (2004) (herein incorporated by reference in its entirety)) used a single stable framework scaffold to introduce diversity to the heavy chain, based on the observed propensities of amino acids in CDRs of natural Abs. Another strategy was to amplify only the CDR sequences from naïve B cells and randomly combine these CDRs into a selected Ab framework that can be highly expressed in bacterial system (Soderlind E, et al. *Nat Biotechnol* 18:852-6 (2000) (herein incorporated by reference in its entirety)). Further understanding of key properties of naturally existing Abs will help Ab engineering technologies to obtain more promising therapeutic Abs candidate.

Here, we compare synthetic Abs to natural Abs to assess to what extent synthetic Abs indeed mimic natural ones. This comparison allowed us to review and revise common assumptions about Ab-Ag interaction. We employ a novel computational tool we developed, "CDRs analyzer" to explore biophysical characteristics of Abs. In this analysis, natural Abs are Abs that originated from hybridoma or from immunized or naïve libraries, and synthetic Abs are Abs that were selected from a synthetic library (i.e., a library that is not naïve or immunized). We found that synthetic Abs rely on CDRH3 significantly more than natural Abs. The binding contribution of CDRH1 and CDRH2 of synthetic Abs is smaller than their contribution in natural Abs. When analyzing the binding mode, we found that epitopes of natural Abs contain many epitope residues that contact multiple CDRs, while epitopes of synthetic Abs have more residues that contact only one CDR. These results show that the current way in which synthetic libraries are designed often yields Abs that do not mimic the way in which natural Abs bind their Ags. Our analysis suggests a set of considerations for library design that will take better advantage of the binding possibilities offered by the structure of the Ab. We discuss how this can yield libraries with more effective binders and with greater diversity of paratopes.

B. Methods

B.1 Construction of Natural Ab-Ag Complexes Datasets

To build a large non-redundant set of natural Abs, a previously published non-redundant dataset of 196 Ab-Ag complexes (Burkovitz, A. et al., *FEBS J* 281:306-19 (2014) (herein incorporated by reference in its entirety)) was further filtered to create the current study dataset of natural Ab-Ag complex. The "CDRs Analyzer" cannot analyze scFv Abs, Abs that contain disorder residues in the CDRs or non-standard amino acids, complexes that were solved by NMR and complexes composed of more than 25000 atoms. Complexes that met these conditions were deleted from the original dataset. In addition, complexes that included synthetic Abs were moved to the synthetic Ab-Ag dataset. Finally, complexes that contain Ag with length of ≤30 amino acids were also removed. The resulting dataset contained 101 natural Ab-Ag complexes (Table S1).

B.2 Construction of Synthetic Ab-Ag Complexes Datasets

A synthetic Ab-Ag complexes dataset was constructed using both the PDB[32] and sAbDab. (Dunbar, J. et al. *Nucleic Acids Res* 42:D1140-6 (2014) (herein incorporated by reference in its entirety). The PDB query search was used to curate manually synthetic Ab-Ag complexes. The PDB query type was set to "PubMed abstract" and search words were "phage display antibody" and "library antibody". In addition, the sequences of the light chain, the heavy chain or the full variable domain of a representative synthetic Ab (PDBID:2H9G) was used to search the sAbDab database using the framework region only option. The retrieved PDB entries were considered synthetic Ab-Ag complexes if the library from which it was isolated included variable domains sequences that were not obtained from a natural repertoire. Two Ab-Ag complexes were considered redundant in case the two Abs bound the same Ag at a similar epitope. Redundancy was removed according to this criterion. We removed from the dataset complexes that contain scFvs, Ag length ≤30 amino acids, Abs that contains disordered residues in the CDRs or non-standard amino acids, complexes with resolution ≤3.6 A° and complexes that are composed of more than 25000 atoms. The final synthetic Ab-Ag complexes dataset contained 36 non-redundant PDB entries.

B.3 Analyzing Ab-Ag Complexes Using "CDRs Analyzer"

CDRs analyzer takes as an input an X-ray structure of Ab-Ag complex in a PDB file format. It automatically identifies the CDRs residues and calculates a set of parameters for all six CDRs. The output is an HTML page presenting the calculated parameters (described below) for each of the CDRs, a list of contacting residues and list of specific interactions. "CDRs Analyzer" was implemented in Perl and Python. The front end of the server is designed in HTML and XML.

Description of CDRs Analyzer:

B.3.1 CDRs Identification

The CDRs are identified using Paratome. (Kunik, V. et al., *Nucleic Acids Res* 40:W521-4 (2012); Kunik, V. et al. *PLoS Comput Biol* 8:e1002388 (2012) (herein incorporated by reference in their entirety) An Ag-contacting residue within ±15 residues from the Ag binding region boundaries as defined by Paratome is added to the nearest DR. An Ag-contacting residue is a residue on the Ab that has at least one non-hydrogen atom within 5 Å from a non-hydrogen atom in the Ag.

B.3.2 Number of Contacting Residues

The number of "contacting residues" is the number of residues in a CDR that are in contact with the Ag and the number of residues in the Ag that are in contact with the CDR.

B.3.3 Number of Specific Interactions

The number of "specific interactions" is the sum of the number of salt-bridges, pi-pi, cation-pi and possible H-bonds (McDonald, I. K. et al., *J Mol Biol* 238:777-93 (1994) (herein incorporated by reference in its entirety)) between the CDR and the Ag. A salt bridge is defined as one Asp or Glu side-chain carboxyl oxygen atom and one side-chain nitrogen atom of Arg, Lys or His that are within 4.0 Å of each other. H-bonds were identified by first adding polar hydrogens atoms to the complex using Discovery Studio Visualizer and then by submitting the output file to HBPLUS program with default parameters. (McDonald, I. K. et al., *J Mol Biol* 238:777-93 (1994) (herein incorporated by reference in its entirety)) Pi-pi interactions are identified according to McGaughey et al. (McGaughey, G. B. et al. *J Biol Chem* 273:15458-63 (1998) (herein incorporated by reference in its entirety)

Briefly, the distance between the centroid of each pair of pi rings should be 8 Å or less, at least one atom from each ring should be within 4.5 Å. In addition, the angle theta between the normal of one or both rings and the centroid-centroid vector must fall between 0 and ±60 degrees. The angle lambda between the normal of each ring must fall between 0 and ±30 degrees. A cation-pi interaction is defined if: Lys or Arg side chains cations are within 7 Å from a centroid of a pi ring. The perpendicular distance between the cation and the plane of the ring is within 6 Å and the angle between the cation-centroid vector and the ring plane is more than 45 degrees.

B.3.4 Energy Calculations ($\Delta\Delta G$)

The effect of in-silico mutation of each CDR residue to ALA is calculated using FoldX. (Guerois, R. et al., *Journal of Molecular Biology* 320:369-87 (2002) (herein incorporated by reference in its entirety)) FoldX's calculations have been previously shown to be correlated to experimentally measured results of 1030 mutants (R=0.83). (Guerois, R. et al. *Journal of Molecular Biology* 320:369-87 (2002)) A recently published study curated 1100 mutations in Ab-Ag complexes and examined the performance of different energy scoring methods. (Sirin, S. et al. *Protein Sci* 2015 (herein incorporated by reference in its entirety).

FoldX was one of the top performers in that study, on both destabilizing ($\Delta\Delta G>1.0$ kcal/mol) and stabilizing ($\Delta\Delta G<-1.0$ kcal/mol) mutations.

Each PDB structure is first optimized using the FoldX RepairPDB function. Then, residues in the CDR are mutated to Ala using the BuildModel function that generated mutants and their corresponding wild-type structure models. The heavy chain and the light chain of the Ab are grouped together to calculated the energy values of the assembled Ab, and the AnalyzeComplex function is used to calculate the binding $\Delta G$ of each model. The calculated $\Delta\Delta G$ for each mutant is then computed by subtracting the wild-type calculated $\Delta G$ value from the mutant calculated $\Delta G$ value. The "$\Delta\Delta G$" of a CDR is considered as the sum over its residues. The "CDRs Analyzer" outputs the ranking of the six CDRs according to the $\Delta\Delta G$ values.

B.3.5 Delta Relative Surface Accessibility (ARSA)

RSA is given by dividing the solvent accessibility value by the surface area of the given amino acid. (Chothia, C., *J Mol Biol* 105:1-12 (1976) (herein incorporated by reference in its entirety)). The solvent accessibility of the Ab residues are calculated using DSSP program. (Kabsch, W. et al., *Biopolymers* 22:2577-637 (1983) (herein incorporated by reference in its entirety). RSA is computed for each of the residues in the CDR, once with Ag presence (RSAbound) and once without Ag presence (RSAunbound). The ARSA is given by subtracting the $RSAQ_{bound}$ from the $RSA_{unbound}$. The ARSA of a CDR is considered as the sum over its residues.

B.3.6 Binding Contribution Score

To evaluate the involvement of each CDR in Ag recognition we used an estimated calculation, which sums the four parameters values into a single "binding contribution score". For each of the four binding parameters above, values are normalized and scored according to their quartiles: 4 points for values within the top 25% of the scores, 1 for the values within the lowest 25%. The "binding contribution score" of a given CDR is the sum of the scores over its criteria varies from 4 (no contribution to Ag binding) to 16 (highest contribution to Ag binding). The binding contribution calculation gives an equal weight for the four binding parameters. When more structural data becomes available, these weights should be assessed and optimized. To verify that the score is not sensitive for arbitrary cutoffs, we checked different binding contribution scores by dividing the parameters values into bins of thirds and fifths (instead of quarters). This did not change the results.

B.3.7 Independent and Integrated Ag Residues

An "independent residue" is an Ag residue that is in contact with residues that belong to only one CDR. An "integrated residue" is an Ag residue that is in contact with at least three CDRs. These parameters are used by the "CDRs Analyzer" to calculate the "Independent binding score", which measure the potential of a given CDR to bind the Ag as peptide. (Burkovitz, A. et al., *J Immunol* 190: 2327-34 (2013) (herein incorporated by reference in its entirety)). For that purpose, the percentage of independent or integrated residues for a given CDR was calculated out of Ag residues contacting that CDR. Here, we aimed to evaluate the complexity of the Ab-Ag interaction. Thus, the percentage of independent or integrated residues were calculated out of the total number of the epitope residues.

B.3.8 Independent Binding Score

The six parameters above (contacting residues, specific interactions, $\Delta\Delta G$, ARSA, percentage of Independent and integrated Ag residues) are used to evaluate the potential of a CDR to bind the Ag as peptide. (Burkovitz, A. et al., *J Immunol* 190:2327-34 (2013) (herein incorporated by reference in its entirety)) The values of each of the parameters are normalized and scored according to their quartiles: 4 points for values within the top 25% of the scores, 1 for the values within the lowest 25%. The "Independent binding score" of a given CDR is the sum of the scores over its six criteria.

C. Results

C.1 Data Sets of Natural and Synthetic Abs

Analyzing the Protein Data Bank (PDB) (Berman H M, et al., *Nucleic Acids Research* 28:235-42 (2000) (herein incorporated by reference in its entirety)) in search of a non-redundant set of natural or synthetic Abs (Methods) yielded a total of 137 Ab-Ag complexes. Of these, 101 are natural (Table S1) and 36 are synthetic (Table S2).

C.2 "CDRs Analyzer"—A Computational Framework for Exploring Ab-Ag Interactions.

The analysis utilized "CDRs Analyzer", a computational tool we introduce for analyzing Ab-Ag interfaces. It is designed to assist Ab engineering by providing quantitative assessment of the biophysical properties of each residue and each CDR in the paratope. "CDRs Analyzer" takes as input a 3D structure of an Ab-Ag complex in a PDB format and the chain IDs of the Ab and Ag chains to be analyzed. The server provides output both at the residue and at the CDRs levels. The output includes a list of H-bonds (calculated by HBPLUS (McDonald I K, and Thornton J M, *J Mol Biol* 238:777-93 (1994) (herein incorporated by reference in its entirety)), salt-bridges, pi-pi and cation-pi interactions, and a list of contacting residues (see Methods). Additionally, "CDRs Analyzer" calculates, for each CDR, four parameters to evaluate its contribution to Ag binding: (1) "Contacting residues" is the sum of the number of residues in the CDR that are in contact with the Ag and the number of residues in the Ag that are in contact with the CDR; (2) "Specific interactions" is the number of salt-bridges, pi-pi and cation-pi interaction and the number of possible H-bonds between the CDR residues and the Ag; (3) "Calculated $\Delta\Delta G$" is the predicted effect on binding of mutating each CDR residue to ALA calculated using FoldX (Guerois, R. et al., *Journal of*

*Molecular Biology* 320:369-87 (2002) (herein incorporated by reference in its entirety)) and (4) "delta relative accessible surface area (ARSA)" is the sum of the changes in the relative solvent accessibility of each CDR residue upon dissociation of the Ab-Ag complex calculated using DSSP (Kabsch, W. and Sander, C., *Biopolymers* 22:2577-637 (1983) (herein incorporated by reference in its entirety)). These four binding parameters were combined to give a score that assesses the contribution to Ag binding of a given CDR. This score varies from 4 (no contribution to Ag binding) to 16 (highest contribution to Ag binding; see Methods). It is a unified score that gives an equal weight for the four binding parameters. Ideally, as more structural data become available, the weight that each parameter should have in the final score can be explored and optimized. The binding contribution score is a combined measurement of the Ag binding portion of a given CDR relative to other CDRs of the Ab.

Additionally, "CDRs analyzer" provides the potential of a CDR to bind the Ag as peptide, based on a computational approach that was described previously (Burkovitz A, et al., *J Immunol* 190:2327-34 (2013) (herein incorporated by reference in its entirety)). "CDRs Analyzer" is available online in http://www.ofranlab.org/CDRs_Analyzer.

C.3 Synthetic Abs Rely Heavily on CDRH3 at the expense of CDRH2 and CDRH1.

Figure 18:
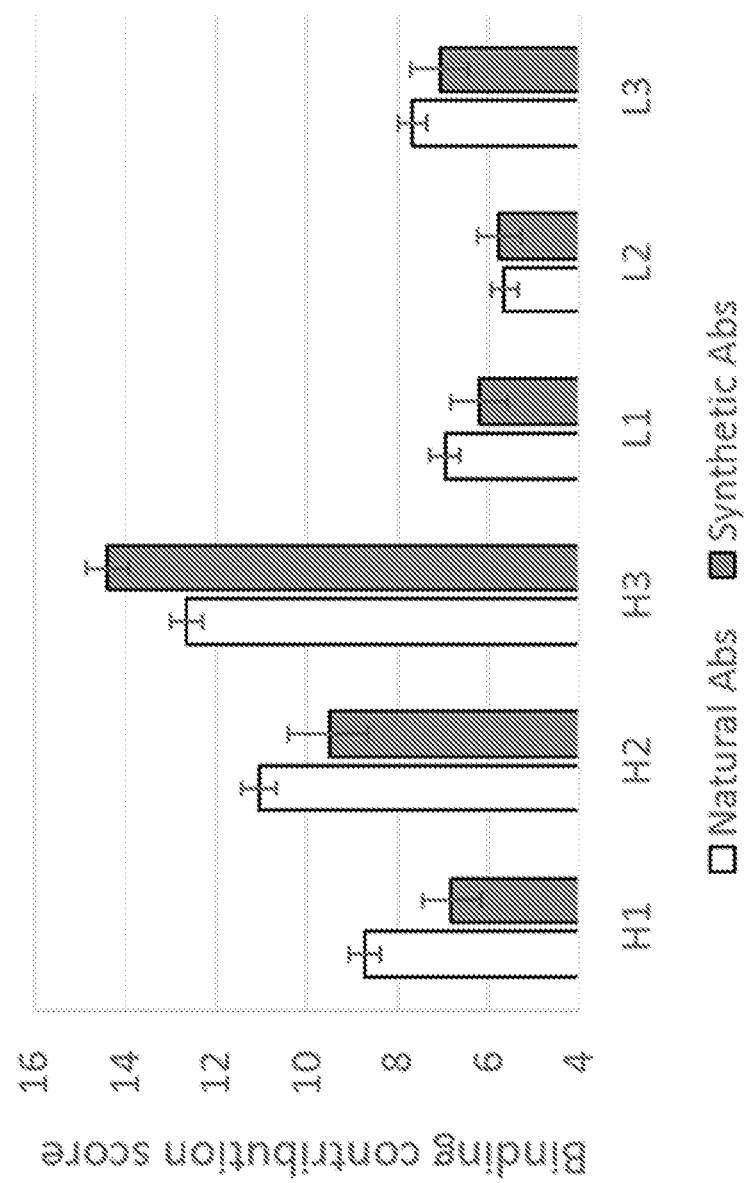

CDRH3, which encompasses the V-D-J recombination site, is the most diverse component of natural Abs. As shown in Table A1, in natural Abs CDRH3 has, on average, higher values than any other CDR, for all of the four parameters that were assessed. FIG. 18, shows how this is translated into the binding contribution score, which is, overall, the highest for CDRH3. Notwithstanding, in natural Abs CDRH2 is a very close second, and has only slightly lower binding contribution than CDRH3. Overall, CDRH3 has an average binding contribution score of 12.69 (±0.35), while CDRH2 has a score of 11.04 (±0.39) (FIG. 18). CDRH1 then follows with 8.66 (±0.36). However, the binding contribution of these three heavy chain CDRs is remarkably different in synthetic Ab-Ag complexes. The contribution of CDRH3 increases from 12.69 (±0.35) to 14.31 (±0.44), while the contribution of CDRH1 and CDRH2 drops from 8.66 (±0.36) to 7.19 (±0.56) and from 11.04 (±0.39) to 9.83 (±0.73), respectively. In addition, in the synthetic Abs, there is a small decrease in the binding contribution score of the three CDRs on the light chain in comparison to their contribution in natural Abs.

Figure 19:
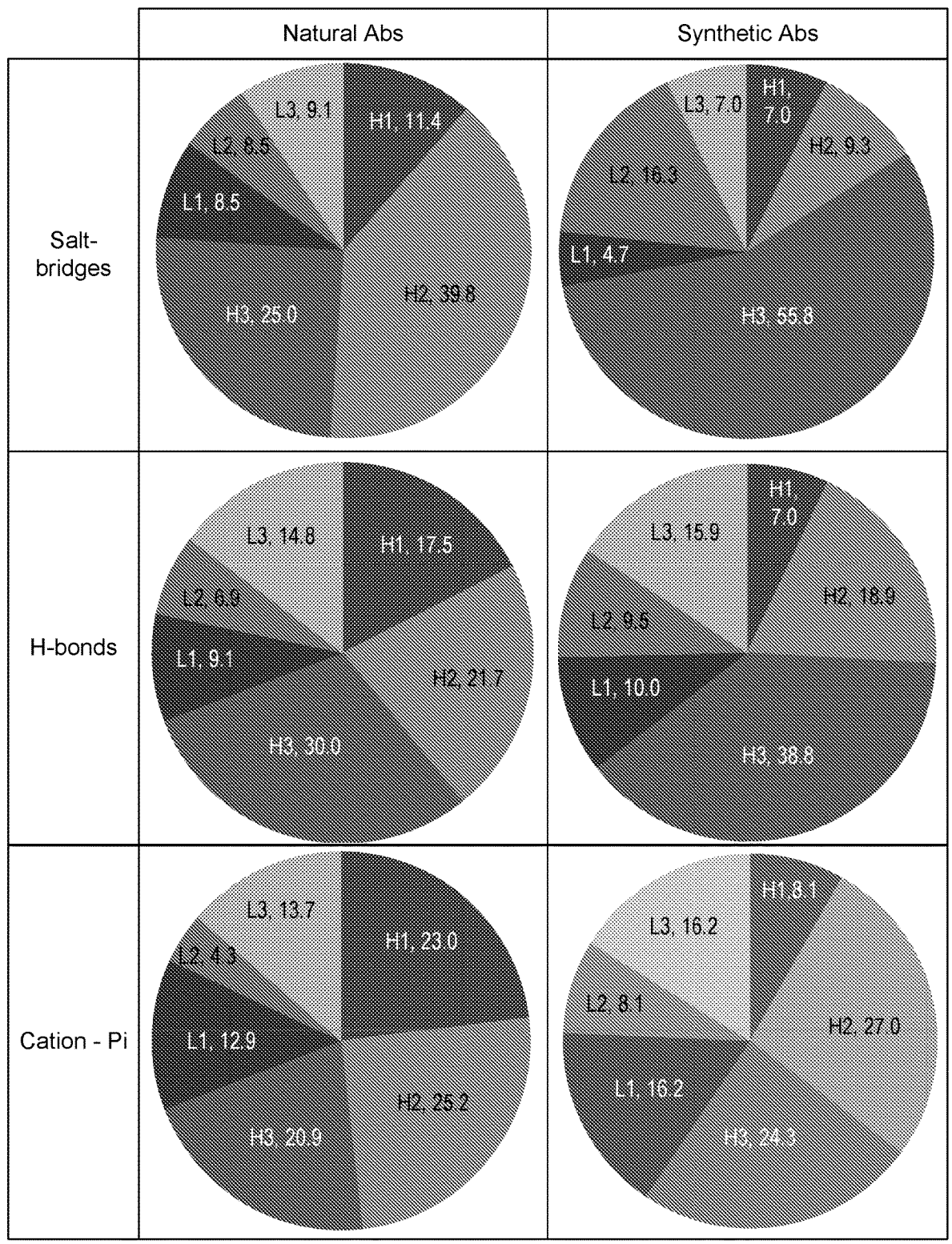
Figure 22:
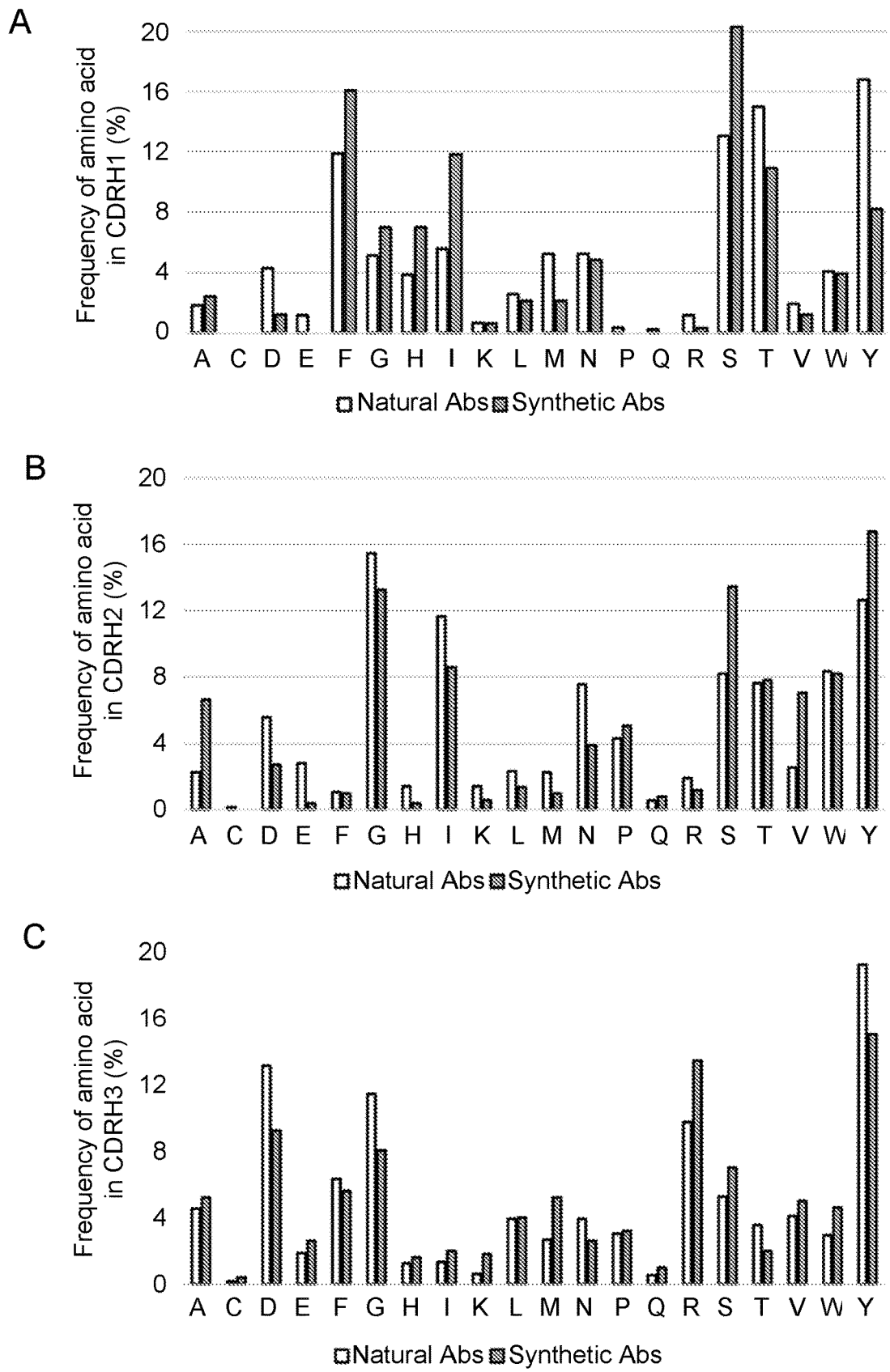

C.4 Unlike Synthetic Abs, CDRs in Natural Abs Specialize in Specific Types of Contacts "CDRs Analyzer" also provides a list of specific contacts (H-bonds, salt bridges, cation-pi or pi-pi). The distribution of each type of interaction across the six CDRs is shown in FIG. 19 (Pi-pi interactions were excluded from the analysis due to their low occurrence, ten interaction in synthetic Abs and eighteen in natural Abs). The extreme dominance of CDRH3 in synthetic Abs emerges also from this analysis. For all types of contacts we analyzed, CDRH3 takes a larger fraction in synthetic Abs than it does in natural Abs. The most extreme is the case of the salt-bridges: In natural Ab-Ag complexes, 39.66% of the salt bridges are formed with CDRH2 and only 25.7% are with CDRH3. However, for synthetic Abs CDRH2 accounts for only 16.13% of the salt-bridges, while CDRH3 share increases to 61.29%. We also analyzed the amino acid composition of the heavy chain CDRs of synthetic and natural Abs. We found the decrease in salt-bridges from CDRH2 is accompanied with substantial decreased frequency of charged amino acids (E,D,H,K and R), from 13.13% in natural CDRsH2 to only 5.26% in synthetic CDRsH2, these results are shown in FIG. 22 and FIG. 23. The percentage of salt-bridges formed by CDRH1 is also greatly affected. In natural Abs 11.17% of the salt bridges are from CDRH1 compared to only 1.61% of the salt bridges in synthetic Abs. The cation-pi and Hbond interaction are also accumulated more in CDRH3 of synthetic Abs compared to natural ones. For these contacts we also observe a dramatic change in CDRH1, which accounts for 17.35% of the Hbonds and 22.7% of the cation-pi interactions in natural Abs. These percentages diminish to 9.96% of the Hbonds and to 10.87% of the cation-pi interactions in synthetic Abs. We also found a decreased frequency of polar amino acids in CDRH1 of synthetic Abs in comparison to that of natural ones (FIG. 23), which is consistent with the decreased share of synthetic CDRH1 in H-bonds.

In natural Abs, each CDR on the heavy chain specializes in different types of interactions (Kunik, V. and Ofran, Y. *Protein Eng Des Sel* 2013 (herein incorporated by reference in its entirety)). As shown above, CDRH2 is responsible the largest share of salt-bridges (39.66%). CDRH3 is the main source for H-bonds (30.14%) and all heavy chain CDRs take similar parts of the cation-pi interactions (20.57%, 22.7% and 26.24% of cation-pi interactions from CDRH3, CDRH1 and CDRH2, respectively). This differentiation and specialization is lost for synthetic Abs. For the Abs that emerge from synthetic libraries, CDRH3 takes the central role in all analyzed interactions. CDRH2 has an equal share as CDRH3 only in cation-pi contacts.

C.5 The Focus of Synthetic Abs on CDRH3 Creates Interfaces that are Less Complex and More Modular.

Figure 20:
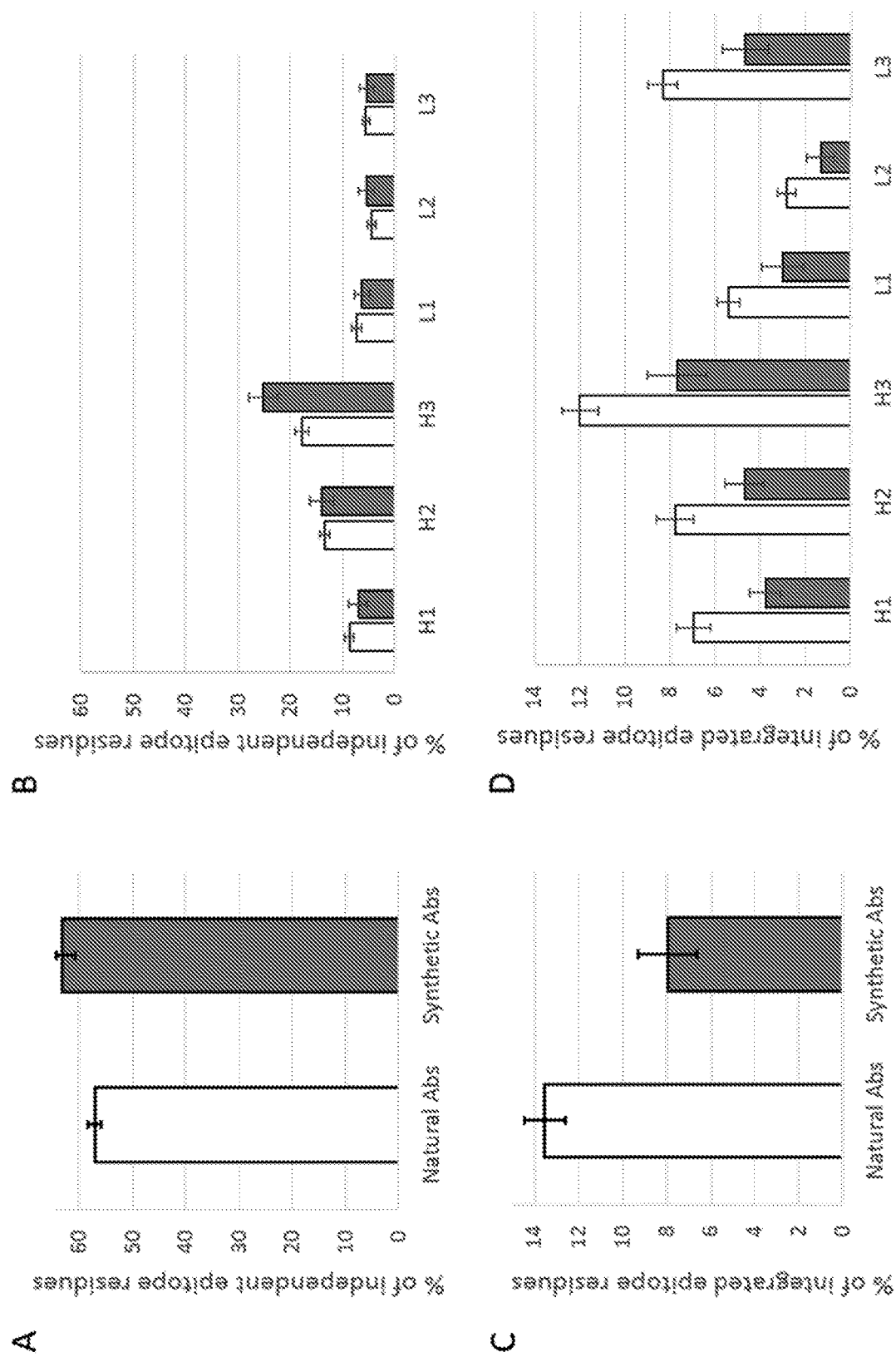

We evaluate the complexity of Ab-Ag interaction using two parameters: independent epitope residue and integrated epitope residues. These parameters reflect the extent to which the six CDRs create an integral interface. An epitope residue on the Ag is considered an "independent residue" if it contacts only one CDR. An epitope residue that contacts three or more different CDRs is considered as an "integrated residue". To assess the complexity of Ab-Ag interaction, the percentage of integrated and independent residues out of all residues that contact the paratope are calculated (note, however, that the raw output of the "CDRs Analyzer" provides this calculations as a percentage of the residues that contact a given CDR and not as a percentage of the residues that contact the entire paratope, see methods). On average, 57.49% of the epitope residues of natural Abs are independent (that is contact only one CDR). Whereas epitope of synthetic Abs are composed of 63.09% independent residues (FIG. 20A). This difference is almost exclusively accounted for an increase in independent interactions with CDRH3 of synthetic Abs (FIG. 20B). We didn't find significant differences for the other CDRs. As for epitope residues that are integrated, their propensity drops from 12.93% for natural Abs to 8.81% for synthetic Abs (FIG. 20C). Unlike independent residues, the integrated residues are significantly decreased across all CDRs of synthetic Abs, except for CDRH1, which shows the same trend, although to lesser extent (FIG. 20D).

C.6 Demonstrating the Differences Between Synthetic and Natural Abs

Figure 21A:
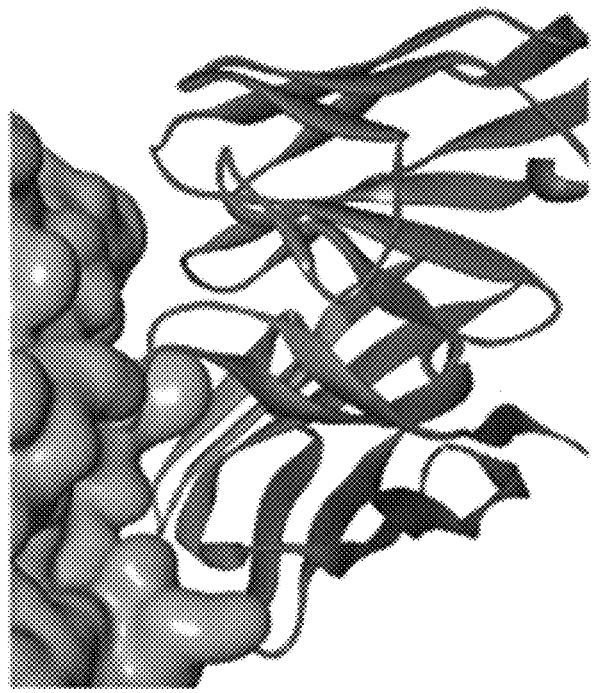
Figure 21A:
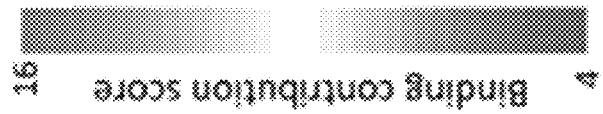
Figure 21B:
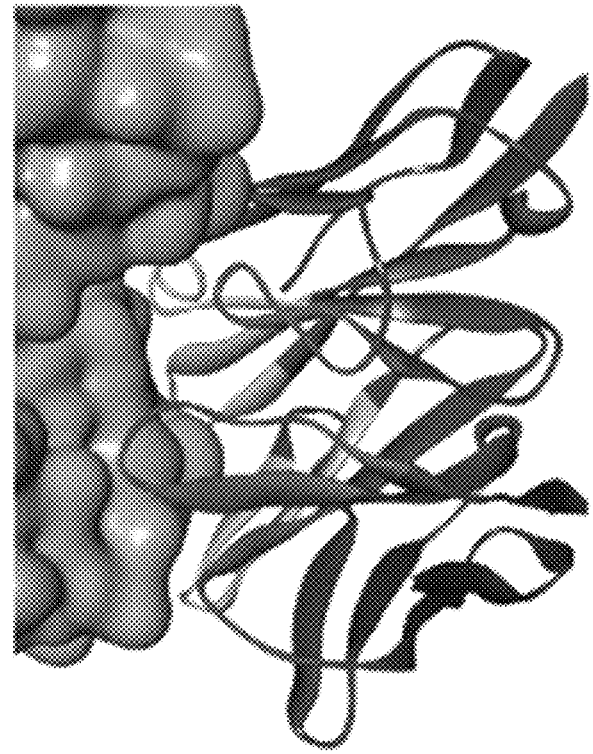

FIG. 21 demonstrates structurally the differences between synthetic and natural Abs. The residues in the figure are according to their binding contribution score from high contribution to no contribution. FIG. 21A shows the structure of the 1918 influenza virus hemagglutinin (HA) bound to the 2D1 Ab, which was isolated from a survivor of the 1918 Spanish flu (Xu, R., et al. *Science* 328:357-60 (2010)

(herein incorporated by reference in its entirety)). In this natural Ab, CDRH3 and CDRL3 both show high or higher contributions reflecting their high contribution to binding, while CDRL1 and CDRH2 show low contributions indicating moderate role in HA recognition. CDRH1 and CDRL2 show low to no contributions reflecting low or no involvement in the interaction. In this complex, 59.25% of the epitope residues are independent residues and 11.1% are integrated residues, which is very similar to the average of all natural Abs. This Ab represents typical features of natural Abs: residues in different CDRs have a major role in Ag recognition, creating a complex, integral interaction. In contrast, the E2 Ab against membrane-type serine protease 1 (MT-SP1) selected from an engineered synthetic library, (Farady. C. J. et al., *J Mol Biol* 380:351-60 (2008) (herein incorporated by reference in its entirety)) shown in FIG. 21B, displays a different recognition pattern. Four of the CDRs, H1, L1, L2 and L3, show low to no contributions. This indicates a low or no influence of these CDRs on binding. Most of the contacts in this case are by CDRH3, which shows high or higher contributions and which is the key player of this Ab-Ag interaction. In addition, only 5.55% of the epitope residues are integrated residues and 83.33% independent residues. Notably, 61.11% of the MT-SP1 epitope residues contact residues only from CDRH3 in comparison to 46.66% of HA epitope residues. This Illustrates the way in which engineered Abs may become a mere scaffold for CDRH3, whereas natural Abs often rely on integral participation of specialized CDRs.

D. Analysis of Results

Synthetic libraries are clearly successful in yielding specific binders that often become successful drug leads. Here, we ask to what extent the products of these libraries mimic natural Abs. One may argue that, as long as the leads are successful, there is no need for the libraries to mimic natural Abs. However, our analysis can be important in two ways: first, as a basic science endeavor, it helps reveal the principles that guide natural Ab-Ag interaction. Second, revealing these principles suggests new avenues that may make synthetic libraries even more potent. While the dataset of synthetic Abs is smaller than that of the natural Abs, the dataset represent a diverse collection of synthetic Abs isolated from a variety of generic (e.g. HuCAL (Knappik, A. et al., *J Mol Biol* 296:57-86 (2000) or Lee et al. (Lee, C. V. et al., *J Mol Riot* 340:1073-93 (2004)) (herein incorporated by reference in their entirety)) or custom made libraries. The synthetic Abs in the dataset bind 30 different Ags, which are varied in their size from 51 to 915 residues. We validate that the Ag recognition occurred in different epitope in case two Abs bind the same Ags. Thus the synthetic Abs dataset represents the current strategies for library design. Obviously, as more synthetic Abs become available this analysis should be repeated to refine the insights and establish their significance further.

Large-scale analysis of Ab-Ag complexes can help reveal the principles that allow Igs to accommodate an exquisitely matching paratope for virtually any surface, while strictly maintaining its overall fold. (Novotn, J. et al., *Proc Natl Acad Sci USA* 83:226-30 (1986); Sela-Culang, I. et al., *Front Immunol* 4:302 (2013); Sela-Culang, I. et al., *Curr Opin Virol* 11:98-102. (herein incorporated by reference in their entirety)) The great challenge of Ab design is to make synthetic libraries that will yield Abs against a wide range of targets and epitopes. Indeed, in vivo Ab development relies on a more complex process, and hence may yield Abs with improved properties. This complex process includes gene rearrangement, somatic hyper mutations, clonal selection, both through positive selection for Ag recognition and negative selection for self-binding. We aimed to identify the differences between the Ag binding mechanism of synthetic Abs and natural Abs, which may help improve library design to yield more natural-line Abs. It also allowed us to revisit common assumptions about the role of CDRH3 in Ag recognition.

Obviously, some individual natural Abs and some individual synthetic Abs may be exceptions to the rule. Yet, our results reveal consistent differences between natural and synthetic Abs. The focus of synthetic libraries on engineering CDRH3 creates CDRH3 loops that participate in Ag recognition above the average of CDRH3 in natural Abs. As a result, CDRs H1 and H2 of synthetic Abs contribute less to Ag binding. CDRH3 loops encompass the V-D-J junction, hence this region displays the largest diversity among the six CDRs of the Abs in terms of length, sequence, and structure (Chothia, C. et al., *Nature* 342:877-83 (1989); Kuroda, D. et al., *Proteins* 73:608-20 (2008); Morea, V. et al., *J Mol Biol* 275:269-94 (1998) (herein incorporated by reference in their entirety)). CDRH3 is also located at the center of the binding site and is the CDR loop that undergoes the most significant conformational changes upon binding (Sela-Culang, I. et al., *J Immunol* 189:4890-9 (2012) (herein incorporated by reference in its entirety)) Thus, it is commonly assumed that CDRH3 accounts for the ability of Abs to recognize and bind specific epitopes. Understandably, Ab engineering methods often focus on CDRH3. For example, Fellouse et al. designed phage display libraries with diversity of $10^4$ to $10^{22}$ in CDRH3 and diversity of 32 to 896 in other CDRs. (Fellouse, F. A. et al., *J Mol Biol* 373:924-40 (2007) (herein incorporated by reference in its entirety)) In the initial HuCAL libraries, (Knappik, A. et al., *J Mol Biol* 296:57-86 (2000) (herein incorporated by reference in its entirety)) diversity beyond the 49 chosen frameworks was introduced only to CDRH3 and CDRL3. In other studies, specific Abs were obtained from libraries with introduced diversity only to CDRH3. (Mahon, C. M. et al. *J Mol Biol* 425:1712-30 (2013); Braunagel, M. and Little, M. *Nucleic Acids Res* 25:4690-1 (1997); der Maur, A A et al., J Biol Chem 277:45075-85 (2002) (herein incorporated by reference in their entirety).

However, the relative importance of CDRH3 compared to other CDRs has been recently revisited in numerous studies. Large scale analyses (Kunik, V. and Ofran, Y., *Protein Eng Des Sel* 2013; Robin, G. et al, *J Mol Biol* 426:3729-43(2014) (herein incorporated by reference in their entirety)) of Abs have assessed the role of CDRH3. It has been demonstrated that CDRH2 may be as important as CDRH3 (Robin, G. et al. *J Mol Biol* 426:3729-43(2014 (herein incorporated by reference in its entirety))) in its contribution to the binding free energy of the Ab-Ag complex. In addition, in 93% of the Ab-Ag complexes, CDRH2 contained at least one residue with high energetic contribution ($\Delta\Delta G > 0.8$ kcal/mol) in comparison to 90% of the complexes with such residues from CDRH3. In another study, CDRH3 was found to be responsible for 30.6% of the energetically important Ag-binding residues. (Kunik, V. and Ofran, Y., *Protein Eng Des Sel* 2013. (herein incorporated by reference in its entirety)) That is, most of the energetically important Ag-binding residues come from other CDRs. This has been shown also for specific examples like the interaction between HyHEL-10 and lysozyme, in which CDRH2 and CDRL1 display a dominant role, while CDRH3 shows very low binding contribution. (Burkovitz, A. et al., *J Immunol* 190:2327-34 (2013) (herein incorporated by reference in its entirety)) The fact that CDRH3 is not necessary for the versatility of Abs was ultimately demonstrated by a study that has shown that synthetic libraries can yield specific Abs against different Ags with diverse CDRL3 and fixed CDRH3. (Persson, H. et al., *J Mol Biol* 425:803-11(2013) (herein incorporated by reference in its entirety)) In another study, the introduction of diversity into the sequence of anti ErbB2 Ab only at CDRH3 did not result in affinity enhanced variant, while beneficial mutants could be obtained by engineering one of the other contacting CDRs (CDRH1,H2,L1 or L3). (Hu, D. et al., *PLoS One* 10:e0129125 (2015) (herein incorporated by reference in its entirety)) This emphasizes that the importance of CDRH3 differ between Abs.

The reliance of synthetic Abs on CDRH3 may take a toll on the diversity of the epitopes that the library can bind, which may be referred to as the effective diversity of the library (as opposed to its actual diversity, represented by the number of unique sequences). Existing synthetic libraries tend to yield Abs with CDRH3 dominance. The typically fixed length and sequence of the other loops does not allow for paratopes with other binding topologies. It is therefore possible that, while the number of variants in the library may be higher than the number of variants in natural repertoires, these synthetic Abs represent only a small subset of the possible Abs that would be represented in a much smaller natural set of Ab sequences.

The effective diversity of a library is not the number of unique Ab sequences it has, but the number of different epitopes they can bind. This is defined by how many of the variants are expressed and fold into Abs with paratopes that are very different from each other. Our results suggest that tampering only with CDRH3 may not be a good way to obtain diverse paratopes. Based on the results presented here, one can propose approaches for improving Ab engineering. Building libraries that allow for higher diversity in all CDRs may result in Abs that have binding modes that are more similar to those of natural Abs, which might increase the effective diversity of the library and culminate in higher success rates. Of note is the degeneration of CDRH2 and CDRH1 in synthetic Abs, most remarkably in the percentage of salt-bridges coming from these CDRs and H-bonds and cation-pi interactions from CDRH1. To correct for this and create better libraries, the amino acid composition in these CDRs should be corrected to favor these types of interactions. This could be achieved by elevating the propensity of charged amino acids in CDRH2 and CDRH1 to produce more salt bridges or elevating the propensity of aromatic, positively charges or polar amino acids in CDRH1 to produce more cation-pi and H-bonds. It is also possible that the frameworks that are commonly used in synthetic libraries are suitable for producing interactions that rely on CDRH3. Considering additional frameworks may, therefore, be beneficial.

A novel approach for the design of synthetic libraries is based on the diversity of natural Ig repertoire (naïve, memory and plasma B-cells), which can be characterized using next generation sequencing (NGS). (Glanville, J. et al., *J Proc Natl Acad Sci USA* 106:20216-21 (2009); Zhai, W. et al., *J Mol Biol* 412:55-71(2011)

Glanville et al. (Zhai, W. et al., *J Mol Biol* 412:55-71 (2011) (herein incorporated by reference in their entirety)) analyzed ~$10^5$ sequences of Ab variable fragments from 654 healthy human donors and, consistent with our finding, reported a substantial contribution to total diversity from somatically mutated residues in CDRs 1 and 2. Based on these results, a synthetic Ab library was constructed by introducing a diversity at positions across the six CDRs while the amino acid usage in each position was design to mimic the natural repertoires usage. (Zhai, W. et al., *J Mol Biol* 412:55-71 (2011) (herein incorporated by reference in its entirety)) The 3D structure of the Ab-Ag complexes that were selected by these modern libraries are still not available. We expect that the relative binding contribution of the different CDRs in these synthetic Abs will better mimic the natural Ab binding mechanism than the synthetic Abs analyzed in the current study.

Although there are many available tools for the automated analysis of Abs sequences, (Kaas, Q. et al., *Nucleic Acids Res* 32:D208-10 (2004); Ehrenmann, F. et al., *Nucleic Acids Res* 38:D301-7 (2010); Kunik, V. et al., *Nucleic Acids Res* 40:W521-4 (2012); Abhinandan, K. R. et al., *J Mol Biol* 369:852-62 (2007); Ye, J. et al. *Nucleic Acids Res* 41:W34-40 (2013); Retter, I. et al *Nucleic Acids Res* 33:D671-4 (2005) (herein incorporated by reference in their entirety)) the development of tools for the structural analysis of Ab-Ag complexes is still in its infancy. Two existing tools that provide comprehensive structural analysis of Abs are ABangle, for calculating the orientation between the VH and the VL, (Dunbar, J. et al., *Protein Eng Des Sel* 26:611-20 (2013) (herein incorporated by reference in its entirety)) and the "AbAgDb dataset", which contains interaction profiles of ~500 Ab-Ag complexes in the PDB. (Kulkarni-Kale, U. et al., *Methods Mol Biol* 1184:149-64 (2014) (herein incorporated by reference in its entirety)). In the "AbAgDb", the data is available only for the curated PDBs and most of the output is at the atoms or residues level and not at CDRs level, similarly to tools analyzing general protein-protein interactions. (Tina, K. G. et al., *Nucleic Acids Res* 35:W473-6 (2007); Laskowski, R. A. et al. *Trends Biochem Sci* 22:488-90 (1997)) (herein incorporated by reference in their entirety).

"CDRs Analyzer" is designed to assist Ab engineering protocols by providing quantitative assessment of the biophysical properties both at the loop level—by assessing the contribution of each CDR—and at the residue level by identifying specific positions of interest within interface. Here, we used "CDRs Analyzer" to explore the differences between natural and synthetic interactions. This tool can be used to analyze Abs against pathogenic Ags or human-self Ags, to explore the theory that V-genes are evolutionarily pre-configured to recognize common motifs in Ags from pathogenic source. "CDRs Analyzer" can also be applied to characterize other sets of immunological interactions. For example, it allows evaluation of the differences in binding properties of peptide-binding Abs and protein-binding Abs, or the differences between different families of Abs or even differences between Abs against different Ags. However, the most straightforward way to use "CDRs Analyzer" is for the analysis of individual Abs. It is applicable for experimentally solved Ab-Ag complexes as well as to computational models of such complexes. The output of "CDRs Analyzer" can assist different Ab engineering protocols. The contacting residues list and the specific interactions list can guide choosing specific positions for Ab affinity enhancement, decreasing aggregation or for deimmunization. The CDRs binding contribution may be an important consideration for CDR grafting, Ab humanization, design of two-in-one Abs and for identifying CDR-derived peptides. (Burkovitz, A. et al. *J Immunol* 190:2327-34 (2013) (herein incorporated by reference in its entirety)).

TABLE A1

Binding parameters of CDRs from natural and synthetic Abs- Average values (standard error) of the four binding parameters calculated by "CDRs Analyzer" for all CDRs in natural and synthetic Abs

| CDR | Abs | Contacting residues | Specific interactions | ΔΔG | ΔRSA |
|---|---|---|---|---|---|
| H1 | natural | 9.39 (±0.45) | 1.64 (±0.16) | 2.28 (±0.25) | 0.81 (±0.05) |
|  | synthetic | 9.17 (±1.05) | 0.94 (±0.18) | 2.19 (±0.41) | 0.84 (±0.12) |
| H2 | natural | 11.76 (±0.54) | 2.5 (±0.21) | 3.7 (±0.29) | 1.1 (±0.06) |
|  | synthetic | 11.94 (±1.08) | 1.97 (±0.33) | 3.34 (±0.43) | 1.25 (±0.13) |
| H3 | natural | 14.25 (±0.48) | 2.79 (±0.22) | 5.77 (±0.36) | 1.31 (±0.06) |
|  | synthetic | 18.97 (±1.23) | 4.39 (±0.56) | 8.2 (±0.68) | 1.83 (±0.16) |
| L1 | natural | 6.62 (±0.43) | 0.93 (±0.13) | 1.78 (±0.19) | 0.59 (±0.05) |
|  | synthetic | 6.03 (±0.78) | 0.92 (±0.28) | 1.4 (±0.34) | 0.59 (±0.08) |
| L2 | natural | 4.58 (±0.51) | 0.64 (±0.11) | 1.24 (±0.17) | 0.41 (±0.05) |
|  | synthetic | 4.75 (±0.85) | 0.83 (±0.27) | 1.3 (±0.33) | 0.45 (±0.09) |
| L3 | natural | 7.74 (±0.43) | 1.35 (±0.14) | 1.76 (±0.17) | 0.62 (±0.04) |
|  | synthetic | 7.06 (±0.71) | 1.47 (±0.28) | 1.93 (±0.32) | 0.59 (±0.07) |

TABLE S1

Non-redundant dataset of natural Ab-Ag complexes:

|  | PDB ID | Heavy chain | Light chain | Antigen chains | origin of Ab | Origin of Ag |
|---|---|---|---|---|---|---|
| 1 | 1A14 | H | L | N | Hybridoma | Pathogenic |
| 2 | 1AFV | H | L | A | Hybridoma | Pathogenic |
| 3 | 1AHW | B | A | C | Hybridoma | Human - self |
| 4 | 1AR1 | C | D | B | Hybridoma | Non pathogenic |
| 5 | 1DQJ | B | A | C | Hybridoma | Non pathogenic |
| 6 | 1E6J | H | L | P | Hybridoma | Pathogenic |
| 7 | 1EGJ | H | L | A | Hybridoma | Human - self |
| 8 | 1EO8 | H | L | A | Hybridoma | Pathogenic |
| 9 | 1EZV | X | Y | E | Hybridoma | Non pathogenic |
| 10 | 1FBI | H | L | X | Hybridoma | Non pathogenic |
| 11 | 1FE8 | H | L | A | Hybridoma | Human - self |
| 12 | 1FJ1 | B | A | F | Hybridoma | Pathogenic |
| 13 | 1FSK | C | B | A | Hybridoma | Pathogenic |
| 14 | 1H0D | B | A | C | Hybridoma | Human - self |
| 15 | 1IQD | B | A | C | Immunized | Human - self |
| 16 | 1JHL | H | L | A | Hybridoma | Non pathogenic |
| 17 | 1JPS | H | L | T | Hybridoma (Humanized) | Human - self |
| 18 | 1JRH | H | L | I | Hybridoma | Human - self |
| 19 | 1K4C | A | B | C | Hybridoma | Non pathogenic |
| 20 | 1KB5 | H | L | AB | Hybridoma | Non pathogenic |
| 21 | 1KEN | H | L | AC | Hybridoma | Pathogenic |
| 22 | 1MLC | B | A | E | Hybridoma | Non pathogenic |
| 23 | 1NCA | H | L | N | Hybridoma | Pathogenic |
| 24 | 1NDG | A | B | C | Hybridoma | Non pathogenic |
| 25 | 1NMB | H | L | N | Hybridoma | Pathogenic |
| 26 | 1NSN | H | L | S | Hybridoma | Pathogenic |
| 27 | 1OAK | H | L | A | Hybridoma | Human - self |
| 28 | 1OB1 | B | A | C | Hybridoma | Pathogenic |
| 29 | 1ORQ | B | A | C | Hybridoma | Non pathogenic |
| 30 | 1ORS | B | A | C | Hybridoma | Non pathogenic |
| 31 | 1OSP | H | L | O | Hybridoma | Pathogenic |
| 32 | 1OTS | C | D | AB | Hybridoma | Pathogenic |
| 33 | 1P2C | B | A | C | Hybridoma | Non pathogenic |
| 34 | 1PKQ | B | A | E | Hybridoma | Non pathogenic |
| 35 | 1QFU | H | L | A | Hybridoma | Pathogenic |
| 36 | 1RJL | B | A | C | Hybridoma | Pathogenic |
| 37 | 1RVF | H | L | 123 | Hybridoma | Pathogenic |
| 38 | 1RZJ | H | L | G | Immunized | Pathogenic |
| 39 | 1SY6 | H | L | A | Hybridoma | Human - self |
| 40 | 1TPX | B | C | A | Hybridoma | Pathogenic |
| 41 | 1V7M | H | L | V | Hybridoma | Human - self |
| 42 | 1VFB | B | A | C | Hybridoma | Non pathogenic |
| 43 | 1WEJ | H | L | F | Hybridoma | Non pathogenic |
| 44 | 1YJD | H | L | C | Hybridoma | Human - self |
| 45 | 1YNT | B | A | F | Hybridoma | Pathogenic |
| 46 | 1YQV | H | L | Y | Hybridoma | Non pathogenic |
| 47 | 1YY9 | D | C | A | Hybridoma | Human - self |
| 48 | 1Z3G | H | L | A | Hybridoma | Pathogenic |
| 49 | 1ZTX | H | L | E | Hybridoma | Pathogenic |
| 50 | 2ADF | H | L | A | Hybridoma | Human - self |
| 51 | 2AEP | H | L | A | Hybridoma | Pathogenic |
| 52 | 2BDN | H | L | A | Hybridoma | Human - self |
| 53 | 2DD8 | H | L | S | Naïve | Pathogenic |
| 54 | 2DTG | A | B | E | Hybridoma | Human - self |
| 55 | 2DTG | C | D | E | Hybridoma | Human - self |
| 56 | 2FD6 | H | L | U | Hybridoma | Human - self |
| 57 | 2HMI | D | C | B | Hybridoma | Pathogenic |
| 58 | 2J4W | H | L | D | Hybridoma | Pathogenic |
| 59 | 2JEL | H | L | P | Hybridoma | Pathogenic |
| 60 | 2NY7 | H | L | G | Immunized | Pathogenic |
| 61 | 2VIR | B | A | C | Hybridoma | Pathogenic |
| 62 | 2VWE | E | C | AB | Hybridoma | Human - self |
| 63 | 2VXQ | H | L | A | Immunized | Pathogenic |
| 64 | 2VXS | K | O | DC | Naïve | Human - self |
| 65 | 2VXT | H | L | I | Hybridoma | Human - self |
| 66 | 2W9E | H | L | A | Hybridoma | Human - self |
| 67 | 2XQY | G | L | A | Hybridoma | Pathogenic |
| 68 | 2XRA | H | L | A | Immunized | Pathogenic |
| 69 | 2XWT | A | B | C | Immunized | Human - self |
| 70 | 2YC1 | A | B | C | Naïve | Toxin |
| 71 | 2ZJS | H | L | Y | Hybridoma | Non pathogenic |
| 72 | 3AB0 | B | C | A | Hybridoma | Pathogenic |
| 73 | 3BGF | B | C | A | Hybridoma | Pathogenic |
| 74 | 3BSZ | H | L | F | Hybridoma | Human - self |
| 75 | 3CVH | H | L | AC | Hybridoma | Non pathogenic |
| 76 | 3D85 | B | A | C | Hybridoma | Human - self |
| 77 | 3D9A | H | L | C | Hybridoma | Non pathogenic |
| 78 | 3EOA | H | L | I | Hybridoma (Humanized) | Human - self |
| 79 | 3FFD | A | B | P | Hybridoma | Human - self |
| 80 | 3FMG | H | L | A | Hybridoma | Pathogenic |
| 81 | 3G04 | B | A | C | Immunized | Human - self |
| 82 | 3GI8 | H | L | C | Hybridoma | Non pathogenic |
| 83 | 3GJF | H | L | AC | Naïve | Human - self |
| 84 | 3I50 | H | L | E | Hybridoma | Pathogenic |
| 85 | 3IDX | H | L | G | Immunized | Pathogenic |
| 86 | 3IU3 | A | B | K | Hybridoma | Human - self |
| 87 | 3IYW | H | L | ABC | Immunized | Pathogenic |
| 88 | 3JWD | H | L | A | Immunized | Pathogenic |
| 89 | 3KJ4 | H | L | A | Hybridoma | Non pathogenic |
| 90 | 3KJ6 | H | L | A | Hybridoma | Human - self |
| 91 | 3KS0 | K | J | A | Hybridoma | Non pathogenic |
| 92 | 3L5W | H | L | I | Hybridoma | Human - self |
| 93 | 3LIZ | H | L | A | Hybridoma | Non pathogenic |
| 94 | 3LQA | H | L | GC | Immunized | Pathogenic |
| 95 | 3LZF | H | L | A | Immunized | Pathogenic |
| 96 | 3MXW | H | L | A | Hybridoma | Non pathogenic |
| 97 | 3NCY | P | S | AB | Hybridoma | Pathogenic |

TABLE S1-continued

Non-redundant dataset of natural Ab-Ag complexes:

| PDB ID | Heavy chain | Light chain | Antigen chains | origin of Ab | Origin of Ag |
|---|---|---|---|---|---|
| 98 | 3NIG | H | L | A | Hybridoma | Human - self |
| 99 | 3O0R | H | L | BC | Hybridoma | Pathogenic |
| 100 | 3P30 | H | L | A | Immunized | Pathogenic |
| 101 | 3RAJ | H | L | A | Hybridoma | Human - self |

TABLE S2

Non-redundant dataset of synthetic Ab-Ag complexes:

| | PDB ID | Heavy chain | Light chain | Antigen chains | Origin of Ab | Origin of Ag |
|---|---|---|---|---|---|---|
| 1 | 1ZA3 | B | A | S | YS binary code[1] | Human - self |
| 2 | 2FJG | H | L | VW | Lee et al.[2] 2004a | Human - self |
| 3 | 2FJH | H | L | VW | Lee et al.[2] 2004a | Human - self |
| 4 | 2H9G | B | A | R | Lee et al.[2] 2004a | Human - self |
| 5 | 2HFG | H | L | R | Lee et al.[2] 2004a | Human - self |
| 6 | 2QQK | H | L | A | VH/VL library[3] | Human - self |
| 7 | 2QQN | H | L | A | VH/VL library[3] | Human - self |
| 8 | 2R0K | H | L | A | Lee et al.[2] 2004a | Human - self |
| 9 | 2XTJ | D | B | A | HuCAL GOLD[4] | Human - self |
| 10 | 3BN9 | D | C | B | HuCAL[5] | Human - self |
| 11 | 3DVG | B | A | XY | Fellouse et al.[6] | Human - self |
| 12 | 3G6D | H | L | A | HuCAL GOLD[4] | Human - self |
| 13 | 3G6J | F | E | AB | Lee et al.[2] 2004a | Human - self |
| 14 | 3GRW | H | L | A | Lee et al.[2] 2004a | Human - self |
| 15 | 3HI6 | X | Y | B | Hoet et al.[7] | Human - self |
| 16 | 3K2U | H | L | A | Lee et al.[2] 2004a | Human - self |
| 17 | 3KR3 | H | L | D | Hoet et al.[7] | Human - self |
| 18 | 3L95 | H | L | Y | | Human - self |
| 19 | 3MA9 | H | L | A | HuCAL GOLD[4] | Pathogenic |
| 20 | 3N85 | H | L | A | WS binary code[8] | Human - self |
| 21 | 3NH7 | H | L | A | HuCAL GOLD[4] | Human - self |
| 22 | 3NPS | B | C | A | HuCAL[5] | Human - self |
| 23 | 3P0Y | H | L | A | Lee et al.[2] 2004a and Bostrom et al.[9] | Human - self |
| 24 | 3P11 | H | L | A | Lee et al.[2] 2004a and Bostrom et al.[9] | Human - self |
| 25 | 3PGF | H | L | A | Fellouse et al.[6] | Pathogenic |
| 26 | 3PNW | B | A | C | Persson et al.[10] | Human - self |
| 27 | 3R1G | H | L | B | VH/VL library[3] | Human - self |
| 28 | 3SOB | H | L | B | Lee et al.[2] 2004a | Human - self |
| 29 | 3U30 | C | B | A | Lee et al.[2] 2004a | Human - self |
| 30 | 4DKE | H | L | AB | Lee et al 2004b[11] and VH/VL library[3] | Human - self |
| 31 | 4DKF | H | L | AB | Lee et al 2004b[11] and VH/VL library[3] | Human - self |
| 32 | 4DN4 | H | L | M | HuCAL GOLD[4] | Human - self |
| 33 | 4JQI | H | L | AV | Fellouse et al.[6] | Non-pathogenic |
| 34 | 4OGY | H | L | A | Hoet et al.[7] | Human - self |
| 35 | 4XTR | E | F | AB | | Non-pathogenic |
| 36 | 4ZFG | H | L | A | Lee et al.[2] 2004a and Bostrom et al.[9] | Human - self |

[1] Fellouse F A, Li B, Compaan D M, Peden A A, Hymowitz S G, Sidhu S S. Molecular recognition by a binary code. J Mol Biol 2005; 348: 1153-62.
[2] Lee C V, Liang W C, Dennis M S, Eigenbrot C, Sidhu S S, Fuh G. High-affinity human antibodies from phage-displayed synthetic Fab libraries with a single framework scaffold. J Mol Biol 2004; 340: 1073-93.
[3] Liang W C, Dennis M S, Stawicki S, Chanthery Y, Pan Q, Chen Y, et al. Function blocking antibodies to neuropilin-1 generated from a designed human synthetic antibody phage library. J Mol Biol 2007; 366: 815-29.
[4] Rothe C, Urlinger S, Löhning C, Prassler J, Stark Y, Jäger U, et al. The human combinatorial antibody library HuCAL GOLD combines diversification of all six CDRs according to the natural immune system with a novel display method for efficient selection of high-affinity antibodies. J Mol Biol 2008; 376: 1182-200.
[5] Knappik A, Ge L, Honegger A, Pack P, Fischer M, Wellnhofer G, et al. Fully synthetic human combinatorial antibody libraries (HuCAL) based on modular consensus frameworks and CDRs randomized with trinucleotides. J Mol Biol 2000; 296: 57-86.
[6] Fellouse F A, Esaki K, Birtalan S, Raptis D, Cancasci V J, Koide A, et al. High-throughput generation of synthetic antibodies from highly functional minimalist phage-displayed libraries. J Mol Biol 2007; 373: 924-40.
[7] Hoet R M, Cohen E H, Kent R B, Rookey K, Schoonbroodt S, Hogan S, et al. Generation of high-affinity human antibodies by combining donor-derived and synthetic complementarity-determining-region diversity. Nat Biotechnol 2005; 23: 344-8.
[8] Birtalan S, Fisher R D, Sidhu S S. The functional capacity of the natural amino acids for molecular recognition. Mol Biosyst 2010; 6: 1186-94.
[9] Bostrom J, Yu SF, Kan D, Appleton B A, Lee C V, Billeci K, et al. Variants of the antibody herceptin that interact with HER2 and VEGF at the antigen binding site. Science 2009; 323: 1610-4.
[10] Persson H, Ye W, Wernimont A, Adams J J, Koide A, Koide S, et al. CDR-H3 diversity is not required for antigen recognition by synthetic antibodies. J Mol Biol 2013; 425: 803-11.
[11] Lee C V, Sidhu S S, Fuh G. Bivalent antibody phage display mimics natural immunoglobulin. J Immunol Methods 2004; 284: 119-32.

Example 6

Methods for Re-Epitoping Antibody

The antibody in this example binds to the human P2X4. Methods to re-epitope the antibody to introduce improved binding were developed. Strategies based on sequence, structural, and biological data were implemented to generate libraries that yielded improved Abs.

The first strategy for library design was based on sequence analyses of the antibody of this example in order to identify positions that play a key role in the native paratope as well as positions and specific variants that may contribute to a re-epitoped interface. Positions were selected for variation if they were in the CDRs, as defined by Paratome and/or Kabat, and if they were not conserved based on sequence alignments of homologs obtained by a Blast search of the pdb database. A total of 50 positions spanning CDRs in both the H and L chains were selected. Each position that was selected was varied independently, using an NNK codon (When N denotes any of the four standard nucleotides and K denotes Guanine or Thyamine), such that the library was made up of clones with single mutations. In addition, a library of clones with double mutations, one in the H chain and one in the L chain was constructed and cloned into a phage display plasmid.

Following three rounds of selection against P2X4 lipoparticles, as well as 'null' lipoparticles (i.e., lipoparticles that do not present the receptor), the libraries underwent deep sequencing to identify positions and variants that were variable or conserved under the different selection positions.

Standard sequencing identified a variant with increased affinity towards P2X4, which contained two mutations (one in each chain). This variant was expressed as soluble scFv and as IgG and the binding affinity was measured using standard techniques.

A second strategy for library design was to select positions for variation based on a combination of sequence, structure, and biological data, which are predicted to form surface patches on the Ab. Variation at each of these patches, or clusters of residues, may yield insight into the native paratope, as well as specific variants that contribute to binding and/or are relevant for re-epitoping. As this strategy includes prediction of surface patches, a three-dimensional model of the antibody is required.

Alternatively, one of the P2X4 library designs (based on P2X4 binder) is based on SHM data (Burkovitz, A. et al. *FEBS J, v.* 281, p. 306-19 (2014); Kunik, V. et al., *Nucleic Acids Res, v.* 40: England, p. W521-4 (2012a)(hereby incorporated by reference in their entirety). SHM data is used to choose positions to vary, and the data that describes the frequencies of the observed Ag-binding amino acid per CDR is used to choose variation at each position. This design does not depend on a 3D model of the antibody, and can be useful for designing a general library that can be used for different targets. Any germline sequence or an antibody with known favorable experimental properties can be used.

Several models of the antibody of this example were generated. Modeling was performed with the Antibody Modeling Protocols in Discovery Studio and in MOE. One of the models underwent further refinement by energy minimization.

Positions for variation were selected if they met the following criteria: 1) High probability of mutation from germline based on data in Burkovitz et al (greater than 0.2 frequency); 2) defined as a CDR by Paratome; 3) Are >10% solvent accessible in the antibody model. As H3 isn't represented fully in the data from Burkovitz et al, all positions in H3 were included. Residues that were predicted to be structurally important, for example, forming a salt-bridge within the antibody in the model, or contributing to hydrophobic core packing, even though they have >10% solvent accessibility, were excluded.

Positions that met the above requirements were visually inspected in the models. Groups of 5 of these positions that had spatial proximity were selected for variation with an NNS codon at each position (S denotes Guanine or Cytosine). Five such libraries were constructed, each spanning a distinct cluster of residues, although with some overlap in positions between some of the libraries. The libraries were cloned into phage display system and underwent selection against P2X4 by employing an iterative process of depletion on HEK cells and panning on P2X4 overexpressing HEK cells.

Enriched clones were sequenced and individually tested for binding. Purified scFV-phage fusion of enriched clones were mixed with a negative control scFv-phage particle at a ratio of 1:1000 and underwent one round of panning on P2X4 expressing HEK cells or on negative control HEK cells. Phages were eluted from the cells and the ratio of the tested clone scFv-phage over the negative control scFv-phage was determined. The enrichment of the tested scFv-phage in the course of panning is proportional to binding. This way a re-epitoped clone, displaying improved binding was identified. The next steps will be to purify a soluble scFv and then IgG determine affinity and test for biological activity.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A method for generating a library of variant antigen binding molecules for screening for binding to an epitope of interest, said method comprising:
    (a) analyzing binding affinities of a set of possible template antigen binding molecules for the epitope of interest and selecting sequence data of a template antigen-binding molecule from said set of possible template antigen binding molecules, wherein said selected template does not bind the epitope of interest and wherein said set of possible template antigen-binding molecules consists of a plurality of known antibodies that do not bind the epitope of interest, wherein said selecting sequence data comprises screening three-dimensional structures or structural models of the set of possible template antigen-binding molecules based on one or more of the following criteria: shape complementarity to the epitope of interest, physicochemical complementarity to the epitope of interest and the predicted free energy of the interaction with the epitope of interest;
    (b) selecting at least one residue position in said selected sequence data of the template antigen-binding molecule of (a) for mutation, wherein said selecting said at least one position comprises (i) screening the three dimensional structure and/or a three-dimensional model of the template antigen-binding molecule sequence data selected in (a) to identify residues that contribute to binding to the epitope of interest; or (ii) conducting multiple sequence alignments of the nucleic acid or the amino acid sequence of the template antigen-binding molecule selected in (a) to identify substitutable positions;
    (c) selecting at least one variant residue to substitute at the at least one residue position selected in the sequence date selected in (b), wherein said selecting the at least one variant residue comprises for each residue identified in step (b), identifying one or more amino acid substitutions that are preferred, allowed or neutral at that residue position;
    (d) substituting at least one variant residue at the at least one residue position selected in (c) in said sequence data;
    (e) generating sequence data of one or more variant antigen binding molecules and synthesizing one or more variant antigen binding molecules of said template antigen-binding molecule, wherein said sequence data of the variant antigen binding molecules comprises at least one substitution identified and substituted in the sequence data of (d); and
    (f) screening said variant antigen binding molecules synthesized, said molecules comprising antibodies or antigen-binding fragments thereof, for binding to the epitope of interest, and selecting variant antigen binding molecules that bind the epitope of interest;
    wherein said method generates a library of variant antigen-binding molecules comprising said substituted sequence data of said template antigen-binding molecule for screening for binding to the epitope of interest.

2. The method of claim 1, wherein said preferred, allowed and/or neutral substitutions in the sequence data are determined by analyzing the amino acid sequences of a plurality of known antibodies compared with the sequence data of the template antigen-binding molecule, wherein analyzing comprises comparison of said amino acid sequences, analysis of composition of said amino acid sequences, analysis of $\Delta\Delta G$ of binding energy, probability of mutation from said germline sequence, or sequence-similarity search algorithms, or any combination thereof.

3. The method of claim 2, wherein said substitutions in the sequence data comprise
    a position prone to somatic hypermutation;
    a position selected based on sequence analysis using multi-sequence alignment to the template, wherein said analysis is by machine learning; or
    a position based on structural analysis, wherein said analysis is by machine learning; or
    a combination thereof.

4. The method of claim 1, wherein said at least one residue selected for mutation is in a CDR region of the sequence data of the template.

5. The method of claim 1, wherein the at least one variant residue selected for mutation comprises residues that is in less than all of the CDRs.

6. The method of claim 1 wherein said method is computer implemented.

* * * * *